(12) United States Patent
Shuhendler et al.

(10) Patent No.: US 10,196,412 B2
(45) Date of Patent: Feb. 5, 2019

(54) PROBE FOR IMAGING PARP-1 ACTIVITY

(71) Applicant: The Board of Trustees of the Leland Stanford Junior University, Palo Alto, CA (US)

(72) Inventors: Adam Shuhendler, Palo Alto, CA (US); Lina Cui, Mountain View, CA (US); Jianghong Rao, Sunnyvale, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 424 days.

(21) Appl. No.: 14/974,447

(22) Filed: Dec. 18, 2015

(65) Prior Publication Data

US 2016/0185805 A1    Jun. 30, 2016

Related U.S. Application Data

(60) Provisional application No. 62/096,583, filed on Dec. 24, 2014.

(51) Int. Cl.
| | |
|---|---|
| *A61K 51/00* | (2006.01) |
| *A61M 36/14* | (2006.01) |
| *C07F 9/6561* | (2006.01) |
| *A61K 51/04* | (2006.01) |

(52) U.S. Cl.
CPC ...... *C07F 9/65616* (2013.01); *A61K 51/0489* (2013.01); *A61K 51/04* (2013.01)

(58) Field of Classification Search
None
See application file for complete search history.

(56) References Cited

PUBLICATIONS

Du et al. (Biochem. 2009, 48, 2878-2890).*
Aboagye E.O. (2010) The future of imaging: developing the tools for monitoring response to therapy in oncology: the 2009 Sir James MacKenzie Davidson Memorial lecture. Br. J. Radiol. 83: 814-822.
Bohndiek S et al (2015) Photoacoustic tomography detects early vessel regression and normalization during ovarian tumor response to the anti-angiogenic therapy Trebananib. J. Nuc. Med.
Burkle, A. (2001) PARP-1: A Regulator of Genomic Stability Linked with Mammalian Longevity. Chembiochem. 2: 725-728.
Choi et al., (2010) Efficiency of fluorodeoxyglucose positron emission tomography/computed tomography to predict prognosis in breast cancer patients received neoadjuvant chemotherapy. J. Surg. Oncol. 102: 392-397.
Dent & Bristow (2011) In Situ DNA Repair Assays As Guides to Personalized Breast Cancer Chemotherapeutics: Ready for Prime Time? J. Clin. Oncol. 29: 2130-2132.
Ganesan S. (2011) MYC, PARP1, and Chemoresistance: BIN There, Done That? Sci. Signal 4: pe15.
Heldahl et al., (2011) Monitoring Neoadjuvant Chemotherapy in Breast Cancer Patients: Improved MR Assessment at 3 T? J. Magn. Reson. Imaging 34: 547-556.
Keliher et al., (2011) High-Yielding, Two-Step 18F Labeling Strategy for 18F-PARP1 Inhibitors. Chem. Med. Chem. 6: 424-427.
Loo et al., (2011) Magnetic Resonance Imaging Response Monitoring of Breast Cancer During Neoadjuvant Chemotherapy: Relevance of Breast Cancer Subtype.J. Clin. Oncol. 29: 660-666.
Querol & Bogdanov (2008) Environment-sensitive and Enzyme-sensitive MR Contrast Agents. Handbook Exp. Pharmacol. 37-57 (2008).
Reiner et al., (2011) Synthesis and in Vivo Imaging of a 18F-Labeled PARP1 Inhibitor Using a Chemically Orthogonal Scavenger-Assisted High-Performance Method. Angew Chem. Int. Ed. Engl. 50: 1922-1925.
Sharma et al., (2011) In vivo 1H MRS in the assessment of the therapeutic response of breast cancer patient. NMR Biomed. 24: 700-711.
Ullal et al., (2011) Nanoparticle-Mediated Measurement of Target-Drug Binding in Cancer Cells. ACS Nano. 5: 9216-9224.
Zong et al., (2004) Alkylating DNA damage stimulates a regulated form of necrotic cell death. Genes Dev. 18: 1272-1282.

* cited by examiner

*Primary Examiner* — Michael G. Hartley
*Assistant Examiner* — Melissa J Perreira
(74) *Attorney, Agent, or Firm* — Thomas|Horstemeyer, LLP

(57) ABSTRACT

Provided are embodiments of a small molecule tracer for positron emission tomography (PET) imaging of the enzyme activity of PARP-1 that is responsible for DNA-damage sensing and critically involved in radiation therapy and some chemotherapy response mechanisms. These PARP-1 tracers are derivatives of nicotinamide adenine dinucleotide (NAD), which is the natural substrate for PARP-1. Provided are NAD derivatives that include a linker moiety to which may be attached a label moiety such as a PET detectable fluorine to generate a 6N-(triazo-PEG2-$^{18}$F)-NAD. Especially advantageous for use in PET and MRI scanning detection systems is the attachment of a chelating agent that allows for the formation of a chelator-metal ion complex.

9 Claims, 32 Drawing Sheets

*t=15 min after 18F-SuPAR Administration

PROBE FOR IMAGING PARP-1 ACTIVITY

CROSS-REFERENCE TO RELATED APPLICATION

This application claims priority to U.S. Provisional Application No. 62/096,583, entitled "PROBE FOR IMAGING PARP-1 ACTIVITY" filed on Dec. 24, 2014, the entirety of which is herein incorporated by reference.

FIELD OF THE DISCLOSURE

The present disclosure relates to Positron Emission Tomography and Magnetic Resonance-detectable probes that specifically detect poly(ADP ribose) polymerase-1 (PARP-1) activity in an animal or human. The present disclosure further relates to methods of detecting and imaging cells and tissues that express active PARP-1.

BACKGROUND

Given the heterogeneity of breast cancer and the range of sensitivity to different therapies, successful management of cancer necessitates personalized therapy (Loo et al., (2011) *J. Clin. Oncol.* 29: 660-666; Ouerol & Bogdanov (2008) *Handbook Exp. Pharmacol.* 37-57 (2008). This entails both optimizing therapy to treat each individual patient and monitoring the response to therapy in near real time. Early response monitoring would allow effective treatments to be continued, and for the cessation of ineffective treatments prior to significant disease progression. However, the ability to accurately determine tumor response to therapy on a short time scale (e.g. within a day) has yet to be achieved, even though it is widely accepted that therapeutic-response monitoring at early stages is crucial for effective cancer treatment.

One predominant subcellular response associated with both radiation therapy and the most common chemotherapeutic agents applied to cancers is severe DNA damage. This severe DNA damage is sensed by the enzyme poly(ADP ribose) polymerase-1 (PARP-1), the activity of which becomes significantly elevated in cancer upon positive response to chemo and radiation therapy. In addition, it has been shown that some cancers have increased PARP-1 basal activity levels that may be responsible for a portion of the resistance of these cancers to certain conventional chemotherapeutic agents (Ganesan S. (2011) *Sci. Signal* 4: pe15). Therefore, PARP-1 sensitive probes could have two-fold utility: (1) a criterion for cancer therapy individualization, and (2) a biochemical marker of early therapeutic response.

Current clinical methods of monitoring therapeutic efficacy involve measures of tumor size either through palpation, ultrasound, MRI, or mammography. However, all of these techniques are limited by poor accuracy and reproducibility, false results, poor correlation with histopathological response, and the inability to detect therapeutic response earlier than after two rounds of therapy, or at least weeks after treatment initiation (Loo et al., (2011) *J. Clin. Oncol.* 29: 660-666; Aboagye E. O. (2010) *Br. J. Radiol.* 83: 814-822; Choi et al., (2010) *J. Surg. Oncol.* 102: 392-397; Dent & Bristow (2011) *J. Clin. Oncol.* 29: 2130-2132; Heldahl et al., (2011) *J. Magn. Reson. Imaging* 34: 547-556; Sharma et al., (2011) *NMR Biomed.* 24: 700-711).

Weissleder et al. reported an inhibitor-based molecular probe for PARP-1, but they bind PARP-1 independent of enzyme activity and only report on the amount of enzyme present in the cell (Keliher et al., (2011) *Chem. Med. Chem.* 6: 424-427; Reiner et al., (2011) *Angew Chem. Int. Ed. Engl.* 50: 1922-1925; Ullal et al., (2011) *ACS Nano.* 5: 9216-9224). These probes therefore cannot differentiate active from inactive PARP-1.

SUMMARY

The disclosure provides embodiments of a PET-detectable probe for imaging PAPR-1 activity in live subjects. PARP-1 is inactive until DNA damage occurs, so enzyme activity but not enzyme expression levels determine the outcome of PARP-1 biochemistry. PARP-1 is a fundamental keeper of DNA integrity in the cell and is thus an important clinical target for a range of diseases, including cancer, arthritis, and neurological diseases. The tracer probes of the disclosure can be used to image PARP-1 biology for basic research applications.

One aspect of the disclosure, therefore, encompasses embodiments of a composition comprising a compound having the formula:

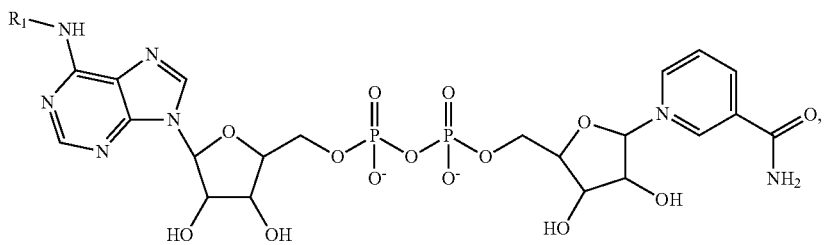

wherein: $R_1$ is

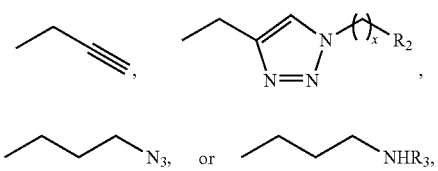

wherein x is 1 or 2; $R_2$ is a detectable label, a halogen, —(O—$(CH_2))_b$-halogen, —$NH_2$, or —NH—CO—($CH_2)_a$—(O—$(CH_2))_b$—$R_4$, wherein a is any of 1-5 and b is any of 0-6; $R_4$ is —$NH_2$,

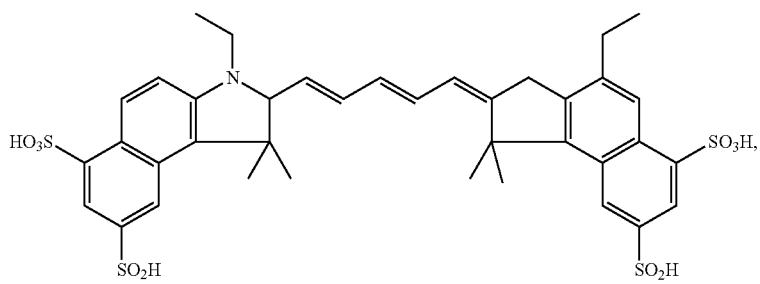

a chelator, or a chelator-metal ion complex; $R_3$ is H or —CO—$(CH_2)_5$—$R_5$; $R_5$ is —$N_3$, —$NH_2$, or —NH—CO—$(CH_2)_5$—$R_6$; $R_6$ is —$N_3$, —$NH_2$,

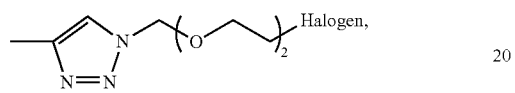

or —NH—CO—$(CH_2)_y$—$R_7$, wherein y is 1 or 2; and $R_7$ is

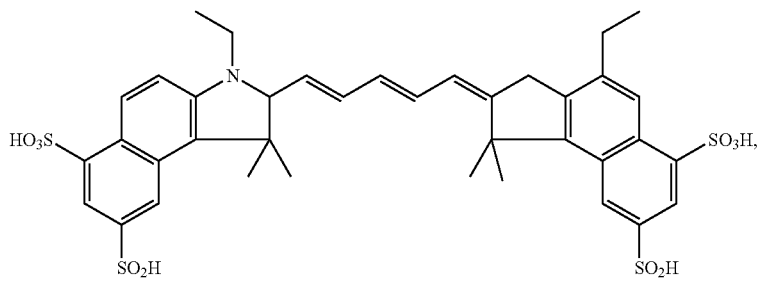

a chelator, or a chelator-metal complex.

In embodiments of this aspect of the disclosure, the detectable label may be selected from the group consisting of $^{18}F$, $^{123}I$, $^{131}I$, $^{125}I$, and $^{11}C$.

In some embodiments of this aspect of the disclosure, the chelator may be ethylaminediaminetetracetate (EDTA), diethylene triamine pentaacetic acid (DPTA), or 1,4,7,10-tetraazacyclododecane-1,4,7,10-tetraacetate (DOTA) and the chelator may have a detectable metal ion bound thereto.

In one embodiment of this aspect of the disclosure, the compound can have the formula:

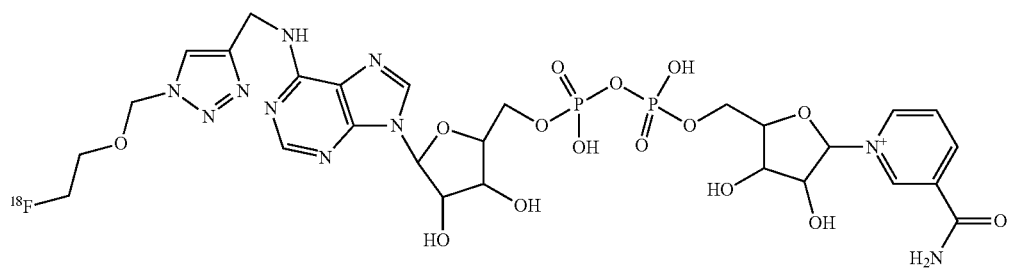 [SMILES: NC(=O)c1ccc[n+](C2OC(COP(=O)(O)OP(=O)(O)OCC3OC(n4cnc5c(NCc6cn(COCC[18F])nn6)ncnc54)C(O)C3O)C(O)C2O)c1]

Another aspect of the disclosure encompasses embodiments of a method of detecting a poly[ADP-ribose] polymerase-1(PARP-1) activity in an animal or human subject, said method comprising the steps of: (i) administering to an animal or human subject a PARP-1-specific probe composition comprising a compound having the formula:

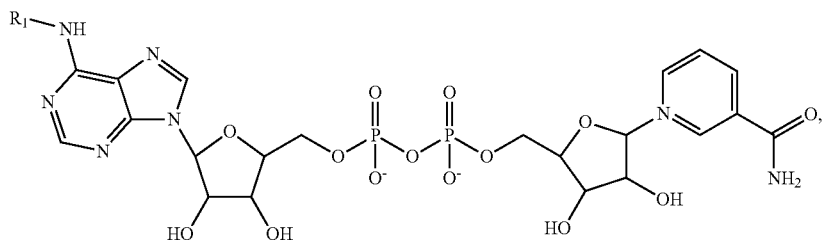

wherein: $R_1$ is

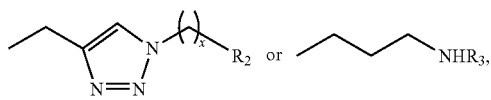

wherein x is 1 or 2; $R_2$ is a detectable label, a halogen, —O—$(CH_2)_b$-halogen, or —NH—CO—$(CH_2)_a$—(O—$(CH_2))_b$—$R_4$, wherein a is any of 1-5 and b is any of 0-6; $R_4$ is a chelator, or a chelator-metal ion complex; $R_3$ is H or —CO—$(CH_2)_5$—$R_5$; $R_5$ is —NH—CO—$(CH_2)_5$—$R_6$; $R_6$ is

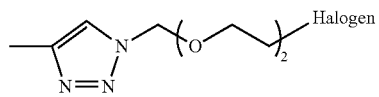

or —NH—CO—$(CH_2)_y$—$R_7$, wherein y=1 or 2; and $R_7$ is, a chelator, or a chelator-metal complex, and the PARP-1-specific probe composition further comprises a pharmaceutically acceptable carrier; (ii) generating a Positron Emission Tomography (PET) signal emitted by the administered probe composition in the animal or human subject; and (iii) generating an image of a localized concentration of the PET signal relative to the body of the animal or human subject, said concentration indicating a site of PARP-1 activity in the subject.

BRIEF DESCRIPTION OF THE DRAWINGS

Many aspects of the disclosure can be better understood with reference to the following drawings.

FIG. 2A illustrates a gel showing that luminol inhibits PARP-1 and allows PARG-mediated degradation of PAR, the product of PARP-1 reaction.

FIG. 2B illustrates a gel demonstrating the kinetics of PAR degradation by PARG.

FIG. 2C is a graph illustrating the quantification of a gel showing that luminol inhibits PARP-1 and allows PARG-mediated degradation of PAR, the product of PARP-1 reaction.

FIG. 2D is a graph illustrating the quantification of a gel demonstrating the kinetics of PAR degradation by PARG.

FIG. 3A illustrates the structures of fluorescent and biotin-labelled NAD.

FIG. 3B illustrates (top) a gel shift assay showing poor substrate potential of the probes shown in FIG. 3A and (bottom) a fluorescent image of the gel showing limited incorporation of fluorophore into PAR product.

FIG. 7A illustrates a synthetic scheme and associated radiochemical yields.

FIG. 7B illustrates UV (top) and radiation-sensitive (bottom) HPLC traces showing purity of product.

FIG. 7C illustrates a gel showing activity of low concentrations of radiolabelled probe, with brightfield (top) and autoradiograph (bottom) of the same gel.

FIG. 7D illustrates a gel showing incorporation of radiolabelled probe at varying ratios to NAD, with brightfield (top) and autoradiograph (bottom) of the same gel.

FIG. 9A shows representative images showing axial (top), coronal (middle), or sagittal (bottom) views of mice 24 h (column 1) or 8 h (column 2) following 10 Gy irradiation, 8 h following 5 Gy irradiation (column 3), or untreated mice (column 4). Tumors are indicated by arrow heads.

FIG. 9B is a graph illustrating time activity curves for tumor uptake of $^{18}$F-SuPAR (n=4 mice/group).

FIG. 9C is a graph illustrating a boxplot of area under the time activity curve showing mean (horizontal line), range (box), and standard deviation (whiskers) (n=4 mice/group). * p<0.05 by ANOVA.

FIG. 10A shows representative images showing axial (top), coronal (middle), or sagittal (bottom) views of mice 24 h (column 1) or 8 h (column 2) following 10 Gy irradiation, 8 h following 5 Gy irradiation (column 3), or untreated mice (column 4). Tumors are indicated by arrow heads.

FIG. 10B is a graph illustrating time activity curves for tumor uptake of $^{18}$F-SuPAR (n=4 mice/group).

FIG. 10C is a graph illustrating a boxplot of area under the time activity curve showing mean (horizontal line), range (box), and standard deviation (whiskers) (n=4 mice/group). * p<0.05 by ANOVA.

FIG. 11A is a graph illustrating time activity curves for tumor uptake of $^{18}$F-SuPAR for HeLa tumor-bearing mice (n=4 mice/group).

FIG. 11B is a graph illustrating a boxplot of area under the time activity curve showing mean (horizontal line), range (box), and standard deviation (whiskers) for HeLa tumor-bearing mice (n=4 mice/group). *p<0.05 by ANOVA.

FIG. 11C is a graph illustrating time activity curves for tumor uptake of $^{18}$F-SuPAR for MDA-MB-231 tumor-bearing mice (n=4 mice/group).

FIG. 11D is a graph illustrating a boxplot of area under the time activity curve showing mean (horizontal line), range (box), and standard deviation (whiskers) for MDA-MB-231 tumor-bearing mice (n=4 mice/group). *p<0.05 by ANOVA.

FIG. 15A illustrates autoradiography (left) and PAR localization by immunofluorescence (right) for serial sections through tumors treated with 10 Gy irradiation 8 h prior to resection (top), treated tumors also given BMN673 (middle), or untreated tumors (bottom).

FIG. 15B is a graph showing the quantitation of tumor:muscle ratios for the autoradiography shown in FIG. 15A. *p<0.05 by ANOVA.

FIG. 15C is a graph showing the quantitation of tumor:muscle ratios for the immunofluorescence sections in shown in FIG. 15A. *p<0.05 by ANOVA.

FIG. 16A illustrates autoradiography (left) and PAR localization by immunofluorescence (right) for serial sections through tumors treated with 10 Gy irradiation 8 hr prior to resection (top), treated tumors also given BMN673 (middle), or untreated tumors (bottom).

FIG. 16B is a graph showing the quantitation of tumor:muscle ratios for the autoradiography shown in FIG. 16A. *p<0.05 by ANOVA.

FIG. 16C is a graph showing the quantitation of tumor:muscle ratios for the immunofluorescence sections in shown in FIG. 16A. *p<0.05 by ANOVA.

Figure 1A:
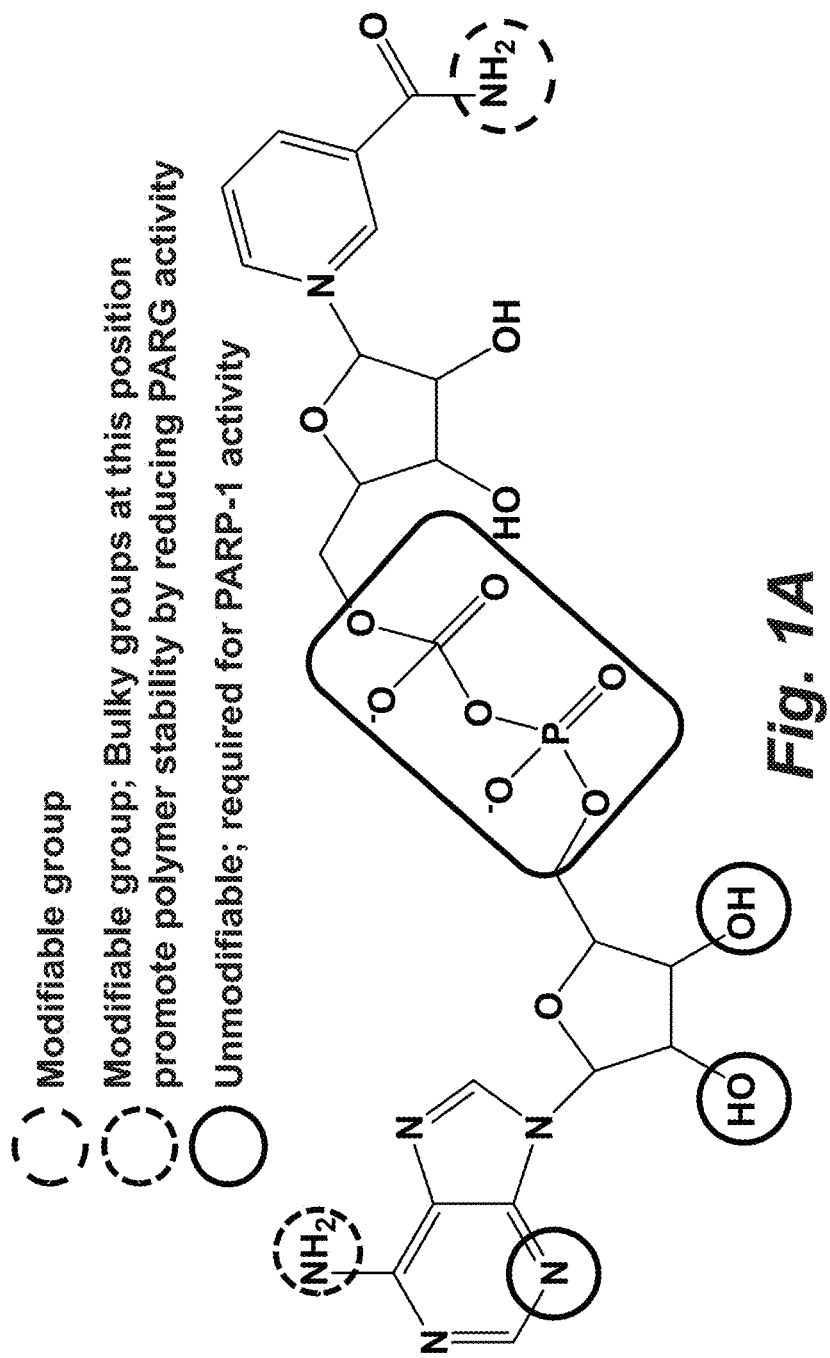
FIG. 1A illustrates a structure of NAD, the endogenous substrate for PARP-1, indicating sites required for polymerization.

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, toxicology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein.

Prior to describing the various embodiments, the following definitions are provided and should be used unless otherwise indicated.

Abbreviations

PARP-1, poly(ADP ribose) polymerase-1; PARG, poly (ADP-ribose) glycohydrolase; PAR, polyADP-ribose.

Definitions

The term "ADP-ribosylation" as used herein refers to the addition of one or more ADP-ribose moieties to a protein (Belenky et al., (2007) *Trends Biochem. Sci.* 32: 12-19; Ziegler M. (2000). *Eur. J. Biochem.* 267: 1550-1564). These reactions are involved in cell signalling and the control of many cell processes, including DNA repair and apoptosis (Berger et al., (2004) *Trends Biochem. Sci.* 29: 111-118; Corda & Di Girolamo (2003) *EMBO J.* 22: 1953-1958).

This protein modification can be produced by $NAD^+$: diphthamide ADP-ribosyltransferase enzymes that transfer the ADP-ribose group from nicotinamide adenine dinucleotide ($NAD^+$) onto acceptors such as arginine, glutamic acid, or aspartic acid. In humans, one type of ADP-ribosyltransferases is the NAD:arginine ADP-ribosyltransferases that modify amino acid residues in proteins such as histones by adding a single ADP-ribose group (Okazaki et al., (1999) *Annual Review of Nutrition* 19: 485-509) These reactions are reversible; for example, when arginine is modified, the ADP-ribosylarginine produced can be removed by ADP-ribosylarginine hydrolases (Takada et al., (1994) *Mol. Cell. Biochem.* 138: 119-122).

Multiple ADP-ribose moieties can also be transferred to proteins to form long branched chains, in a reaction called polyADP-ribosylation (Diefenbach et al., (2005) *Cell. Mol. Life Sci.* 62: 721-730). This protein modification is carried out by the polyADP-ribose polymerases (PARPs) that are found in most eukaryotes (Diefenbach et al., (2005) *Cell. Mol. Life Sci.* 62: 721-730; Burkle A. (2005) *FEBS J.* 272: 4576-4589). The resulting poly(ADP-ribose) structures are involved in the regulation of various cellular events and is most important in the cell nucleus, in processes such as DNA repair and telomere maintenance (Burkle A. (2005) *FEBS J.* 272: 4576-4589).

The term "poly[ADP-ribose] polymerase 1 (PARP-1)" as used herein refers to $NAD^+$ ADP-ribosyltransferase 1 (EC number 2.4.2.30) (poly[ADP-ribose] synthase 1), and is an enzyme that in humans is encoded by the PARP1 gene. PARP1 acts by modifying nuclear proteins by polyADP-ribosylation. PARP1 is involved in differentiation, proliferation, and tumor transformation, normal or abnormal recovery from DNA damage, may be the site of mutation in Fanconi anemia, and may participate in the pathophysiology of type I diabetes.

PARP1 has a role in repair of single-stranded DNA (ssDNA) breaks. Reducing intracellular PARP1 levels with siRNA or inhibiting PARP1 activity with small molecules reduces the repair of ssDNA breaks. In the absence of PARP1, when these breaks are encountered during DNA replication, the replication fork stalls, and double-strand DNA (dsDNA) breaks accumulate. These dsDNA breaks are repaired via homologous recombination (HR) repair, a potentially error-free repair mechanism. For this reason, cells lacking PARP1 show a hyper-recombinagenic phenotype (e.g., an increased frequency of HR), which has also been observed in vivo in mice using the pun assay. Thus, if the HR pathway is functioning, PARP1 null mutants (cells without functioning PARP1) do not show an unhealthy phenotype, and in fact, PARP-1 knockout mice show no negative phenotype and no increased incidence of tumor formation.

Cells that are deficient in BRCA1 or BRCA2 have been shown to be highly sensitive to PARP1 inhibition or knockdown, resulting in cell death by apoptosis, in contrast to cells with at least one good copy of both BRCA1 and BRCA2. Many breast cancers have defects in the BRCA1/BRCA2 HR repair pathway due to mutations in either BRCA1 or BRCA2, or other essential genes in the pathway. Such tumors are hypothesized to be highly sensitive to PARP1 inhibitors, and it has been demonstrated in mice that these inhibitors can both prevent BRCA1/2-deficient xenografts from becoming tumors and eradicate tumors having previously formed from BRCA1/2-deficient xenografts.

PARP activity (which is mainly due to PARP1) measured in the permeabilized mononuclear leukocyte blood cells of thirteen mammalian species (rat, guinea pig, rabbit, marmoset, sheep, pig, cattle, pigmy chimpanzee, horse, donkey, gorilla elephant and man) correlates with the maximum lifespans of these species. Lymphoblastoid cell lines established from blood samples of humans who were centenarians (100 years old or older) have significantly higher PARP activity than cell lines from younger (20 to 70 years old) individuals. In addition, the Wm protein is deficient in persons with Werner syndrome, a human premature aging disorder. PARP1 and Wm proteins are part of a complex involved in the processing of DNA breaks. These findings indicate that there is a linkage between longevity and PARP-mediated DNA repair capability, and that PARP repair activity contributes to mammalian longevity consistent with the DNA damage theory of aging. PARP-2 is the only PARP besides PARP-1 whose catalytic activity is known to be stimulated by damaged DNA.

The term "polyADP-ribose glycohydrolase (PARG)" as used herein refers to an enzyme that catabolizes polyADP-ribose (PAR) mediated with both exo- and endoglycosidase activities to hydrolyze the glycosidic linkages between the ADP-ribose units of PAR and producing free ADP-ribose. In mammals, a single PARG gene encodes multiple PARG proteins with two predominant isoforms: a long nuclear/cytoplasmic isoform (approximately 110 kDa) and a short cytoplasmic isoform (approximately 65 kDa), both of which possess catalytic activity. The abundance of PARG in the cytoplasm contrasts with many of the PARP enzymes that are located in the nucleus, but may indicate that low levels of PARG are sufficient for the catabolism of nuclear PAR.

In vivo, the steady-state levels of PAR are regulated by the opposing actions of the PARPs and PARG. The degradation of PAR may begin immediately upon the initiation of PAR synthesis and can be completed within minutes after the cessation of PAR synthesis has occurred. This suggests that PAR and PAR-metabolizing enzymes are highly regulated. Although PARP-1 is present at a 5-fold to 20-fold molar excess over PARG in some cell types, a variety of regulatory mechanisms act to control the levels of PAR in the nucleus. For example, PARP-1 has a low basal enzymatic activity that is stimulated dramatically by PARP-1's binding partners, including various proteins and forms of DNA. PARG, on the other hand, has a higher specific activity than PARP-1, and its enzymatic activity increases with increased PAR length.

The term "Positron Emission Tomography" (PET) as used herein refers to a nuclear medicine imaging technique that produces a three-dimensional image or map of functional processes in the body. The system detects pairs of gamma rays emitted indirectly by a positron-emitting radioisotope, which is introduced into the body on a metabolically active molecule. Images of metabolic activity in space are then reconstructed by computer analysis. Using statistics collected from tens-of-thousands of coincidence events, a set of simultaneous equations for the total activity of each parcel of tissue can be solved by a number of techniques, and a map of radioactivities as a function of location for parcels or bits of tissue may be constructed and plotted. The resulting map shows the tissues in which the molecular probe has become concentrated. Radioisotopes used in PET scanning are typically isotopes with short half-lives such as carbon-11 ($^{11}C$) (about 20 min), nitrogen-13 ($^{13}N$) (about 10 min), oxygen-15 ($^{15}O$) (about 2 min), and fluorine-18 ($^{18}F$) (about 110 min). PET technology can be used to trace the biologic pathway of any compound in living humans (and many other species as well), provided it can be radiolabeled with a PET isotope. The half-life of fluorine-18 is long enough such that fluorine-18 labeled radiotracers can be manufactured commercially at an offsite location.

The term "Magnetic Resonance Imaging" (MRI) as used herein is a method to obtain an image representing the chemical and physical microscopic properties of materials, by utilizing a quantum mechanical phenomenon, named Nuclear Magnetic Resonance (NMR), in which a system of spins, placed in a magnetic field resonantly absorb energy, when applied with a certain frequency.

The term "activatable probe" as used herein refers to a probe monomer of the disclosure that by action of the targeted PARP-1 enzyme can form concatameric structures comprising multiple conjugated labelled molecules that have amplified detection properties.

The term "chelator" as used herein refers to a molecular moiety that may form ionic bonds to an anion and in particular to metallic ions that have at least two positive charges thereon. Chelating agents containing paramagnetic metals for use in magnetic resonance imaging can also be employed as ancillary agents.

The metal binding moieties useful for incorporation into the compositions of the disclosure may be any chemistry that binds a metal. In certain embodiments, the metal binding moiety can comprise an organic chelating ligand such as those known in the art using amine and carboxylate functionalities on the organic chelating ligand. By way of example, such an organic chelating ligand preferably coordinates a metal using the coordination chemistry of a compound such as, but not limited to, diethylenetriaminepentaacetic acid (DTPA), ethylenediamine tetraacetic acid (EDTA), N,N-bis(carboxymethyl)glycine (NTA), diethylenetriaminepentaacetate (DTPA), 1,4,7,10-tetraazacyclododecane-1,4,7,10-tetraacetic acid (DOTA), mercaptoacetylglycine (MAG3), 1,4,8,11-tetraazacyclotetradecane (CYCLAM), 1,4,7,10-tetraazacyclododecane, cyclen, 1,4,7-triazacyclononane (TACN), and hydrazinonicotinamide (HYNIC).

The term "alkynyl" as used herein refers to groups that include straight and branched chain alkyl groups, except that at least one triple bond exists between two carbon atoms.

The term "polyethylene glycol (PEG)" as used herein refers to the polymerized form of the monomeric structure —O—CH2-CH2-. In the embodiments of the disclosure, the polymer may comprise, but is not limited to, from 1 to about 6 polymerized monomers.

The term "pharmaceutically acceptable carrier" as used herein refers to a diluent, adjuvant, excipient, or vehicle with which a probe of the disclosure is administered and which is approved by a regulatory agency of the Federal or a state government or listed in the U.S. Pharmacopeia or other generally recognized pharmacopeia for use in animals, and more particularly in humans. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. When administered to a patient, the probe and pharmaceutically acceptable carriers can be sterile. Water is a useful carrier when the probe is administered intravenously. Saline solutions and aqueous dextrose and glycerol solutions can also be employed as liquid carriers, particularly for injectable solutions. Suitable pharmaceutical carriers also include excipients such as glucose, lactose, sucrose, glycerol monostearate, sodium chloride, glycerol, propylene, glycol, water, ethanol and the like. The present compositions, if desired, can also contain minor amounts of wetting or emulsifying agents, or pH buffering agents. The present compositions advantageously may take the form of solutions, emulsion, sustained-release formulations, or any other form suitable for use.

The term "detectable" refers to the ability to detect a signal over the background signal. The detectable signal is defined as an amount sufficient to yield an acceptable image using equipment that is available for pre-clinical use. A detectable signal may be generated by one or more administrations of the probes of the present disclosure. The amount administered can vary according to factors such as the degree of susceptibility of the individual, the age, sex, and weight of the individual, idiosyncratic responses of the individual, the dosimetry, and the like. The amount administered can also vary according to instrument and digital processing related factors.

The term "in vivo imaging" as used herein refers to methods or processes in which the structural, functional, or physiological state of a living being is examinable without the need for a life-ending sacrifice.

The term "non-invasive in vivo imaging" as used herein refers to methods or processes in which the structural, functional, or physiological state of a being is examinable by remote physical probing without the need for breaching the physical integrity of the outer (skin) or inner (accessible orifices) surfaces of the body.

The term "label" as used herein refers to an atom, or radioactive atom detectable by such methods as γ-radiation detection, positron emission transmission, and the like, or to an inorganic or organic molecule that may be detected by an optical method, for example by fluorescence detection, light absorbance and the like. It should be noted that reference to detecting a signal from a probe also includes detecting a signal from a plurality of probes. In some embodiments, a signal may only be detected that is produced by a plurality of probes. Additional details regarding detecting signals (e.g., acoustic signals) are described below.

The "imaging moiety" may be detected either externally to a subject human or non-human animal body or via use of detectors designed for use in vivo, such as intravascular radiation or optical detectors such as endoscopes, or radiation detectors designed for intra-operative use. The imaging moiety is preferably chosen from, but is not limited to a positron-emitting radioactive non-metal or a reporter suitable for in vivo optical imaging. It is contemplated, however, that other detectable labels may be incorporated into the probes of the disclosure including, but not limited to a radioactive nuclide. When the imaging moiety is a radioactive metal ion, i.e. a radiometal, suitable radiometals can be either positron emitters such as $^{64}$Cu, $^{48}$V, $^{52}$Fe, $^{55}$Co, $^{94}$mTc or $^{68}$Ga or γ-emitters such as 99mTc, $^{111}$In, $^{113}$In, $^{67}$Ga. When the imaging moiety is a positron-emitting radioactive non-metal, suitable such positron emitters can include, but are not limited to: $^{123}$I, $^{131}$I, $^{125}$I, $^{11}$C, $^{13}$N, $^{15}$O, $^{17}$F, $^{18}$F, $^{75}$Br, $^{76}$Br or $^{124}$I.

The term "contrast agent" as used herein refers to an agent that when delivered to an animal or human subject can improve the image obtained by a method such as magnetic resonance imaging (MRI). Such agents may include, but are not limited to gadolinium, iron oxide, manganese and magnesium salts, and the like that may be formulated into pharmaceutically acceptable compositions for administering in vivo with limited and acceptable degrees of undesirable side effects. One suitable MRI contrast agent for incorporation into the liposomal nanoparticle delivery vehicles of the disclosure is gadolinium (Gd), and derivatized variants thereof. A particularly useful such derivative, but not intended to be limiting, is Gadofluorine (GdF, Bayer Schering Pharma AG), a gadolinium analogue that is an amphiphilic, macrocyclic, gadolinium-containing complex. It is a derivative of Gd-DO3A containing a perfluorooctyl side chain and a mannose moiety. Other Gd derivatives for use as an MRI contrast agent are, but not limited to, Carbocyanine-labelled GdF (cc-GdF), Gd-DTPA (MAGNEVIST®, Bayer Schering Pharma, Berlin, Germany), Gd-DO3A and the like.

The term "dye" as used herein refers to any reporter group whose presence can be detected by its light absorbing or light emitting properties. For example, Cy5 is a reactive water-soluble fluorescent dye of the cyanine dye family. Cy5 is fluorescent in the red region (about 650 to about 670 nm). It may be synthesized with reactive groups on either one or both of the nitrogen side chains so that they can be chemically linked to either nucleic acids or protein molecules. Labeling is done for visualization and quantification purposes. Cy5 is excited maximally at about 649 nm and emits maximally at about 670 nm, in the far red part of the spectrum; quantum yield is 0.28. FW=792. Suitable fluorophores(chromes) for the probes of the disclosure may be selected from, but not intended to be limited to, fluorescein isothiocyanate (FITC, green), cyanine dyes Cy2, Cy3, Cy3.5, Cy5, Cy5.5, Cy7, Cy7.5 (ranging from green to near-infrared), Texas Red, and the like. Derivatives of these dyes for use in the embodiments of the disclosure may be, but are not limited to, Cy dyes (Amersham Bioscience), Alexa Fluors (Molecular Probes Inc.), HiLyte™ Fluors (AnaSpec), and DyLite™ Fluors (Pierce, Inc).

Where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

Further definitions are provided in context below. Unless otherwise defined, all technical and scientific terms used herein have the same meaning as commonly understood by one of ordinary skill in the art of molecular biology. Although methods and materials similar or equivalent to those described herein can be used in the practice or testing of the present disclosure, suitable methods and materials are described herein.

DESCRIPTION

It is desirable to provide imaging probes that are sensitive to subcellular markers indicative of a positive response to therapy. Advantageously, such responses should be detectable significantly earlier than changes in tumor size, for example, and would better reflect the histological response. Such a probe could also provide information regarding the drug-target status of a patient prior to therapy. This would allow a therapy to be specifically tailored to the disease of an individual. Accordingly, the present disclosure encompasses embodiments of a PARP-1-activatable PET tracer probe that can provide early information regarding the DNA repair status of a tumor in vivo that strongly correlates to a positive therapeutic response at the subcellular level.

PET is routinely used during the course of clinical management of cancer due to its high sensitivity ($10^{-15}$ M) and spatial resolution (2-4 mm$^3$), rapid whole body scan times (less than about 20 min), and its ability to provide both anatomical and molecular information when combined with computed tomography (PET/CT) (Bohndiek et al., (2010) *Expert Rev. Mol. Diagn.* 10: 417-434). Given the importance of monitoring tumor treatment response, the wide use of PET for cancer imaging, and the unique potential of PARP-1 as a marker for personalized therapy, the PARP-1-activatable PET tracers of the disclosure are advantageous for enhancing the practice of clinical oncology. Pre-clinical application of the probes of the disclosure can also significantly improve the search for more effective cancer therapies by enhancing the temporal resolution of pre-clinical therapeutic response monitoring (from days to hours) and provide useful biochemical data regarding the effect of novel therapies on tumor survival.

Figure 1B:
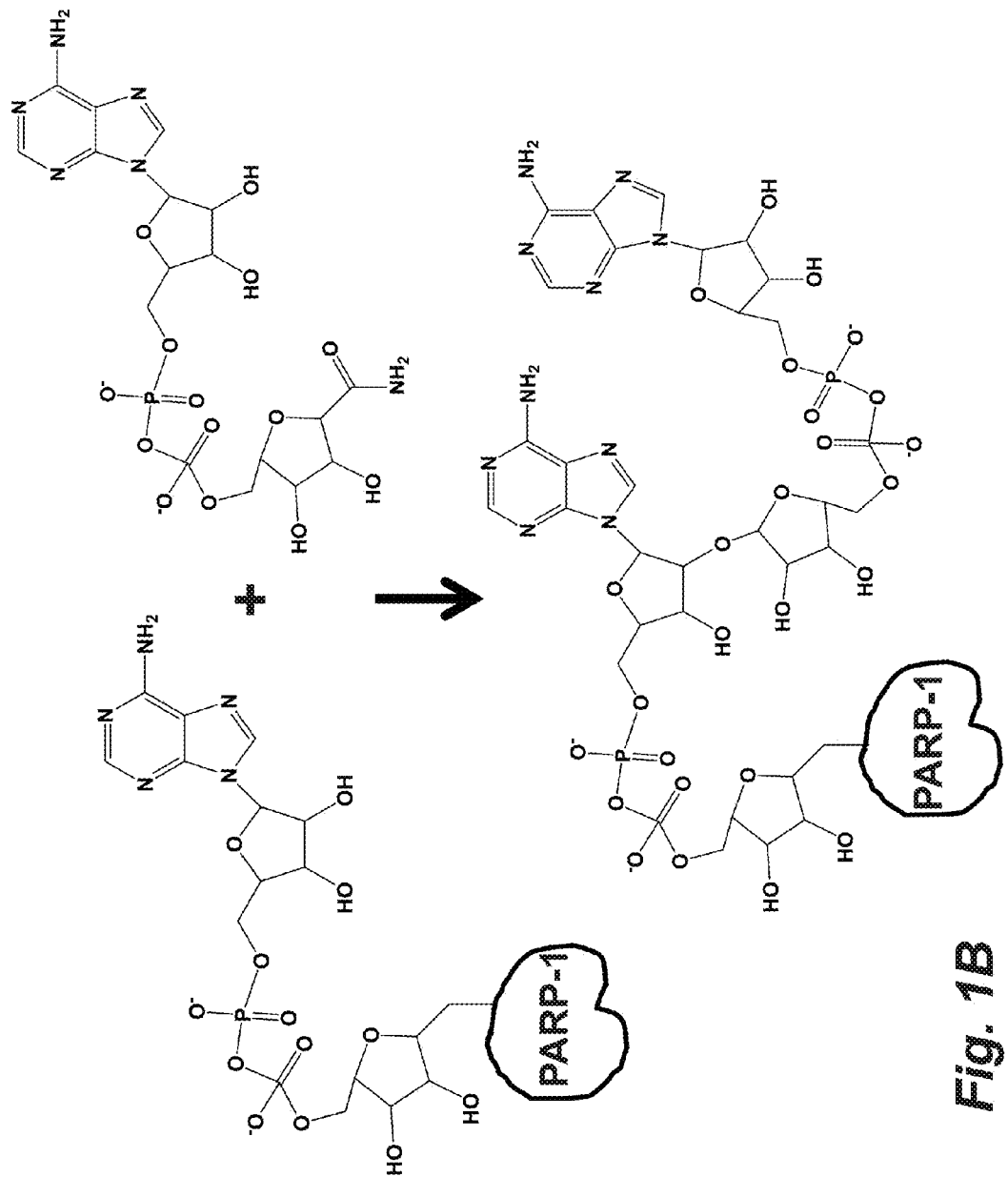
FIG. 1B illustrates a mechanism of the polymerization of NAD catalyzed by PARP-1.
Figure 2A:
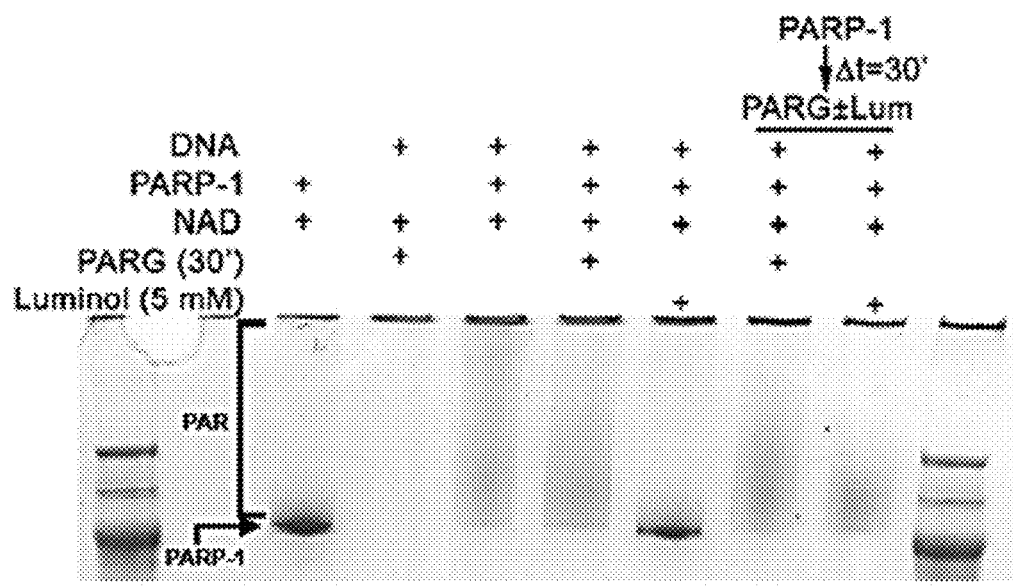
FIGS. 2A-2D illustrate the validation of the gel-shift assay for in vitro assessment of PARP-1 and PARG activity.
Figure 2B:
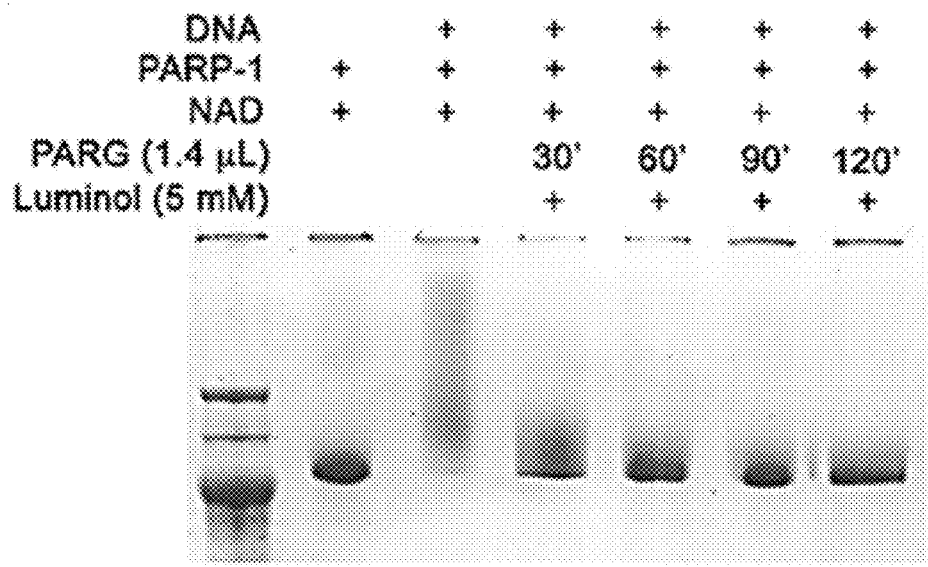
Figure 2C:
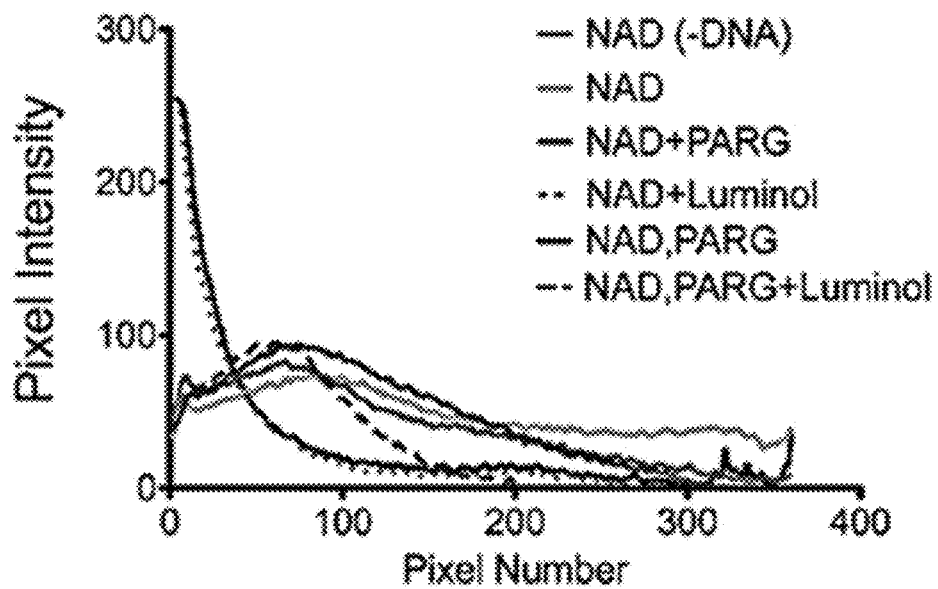
Figure 2D:
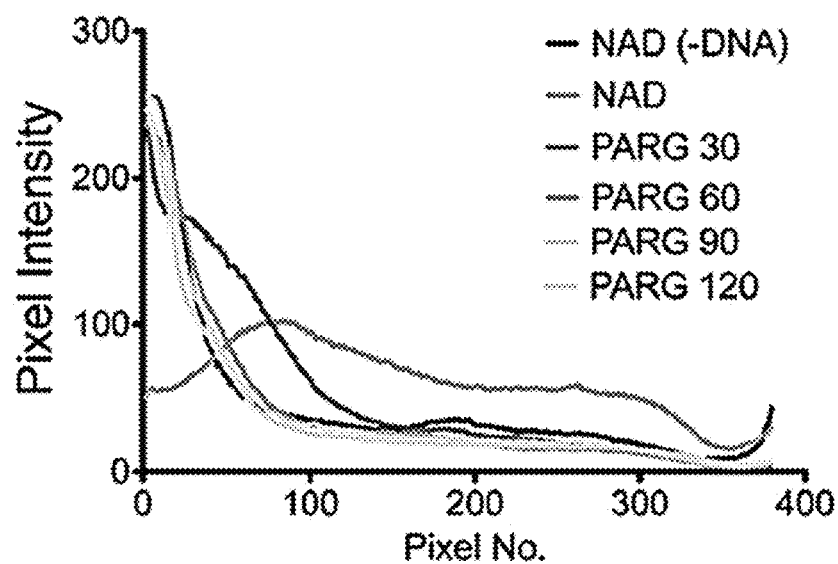
Figure 3A:
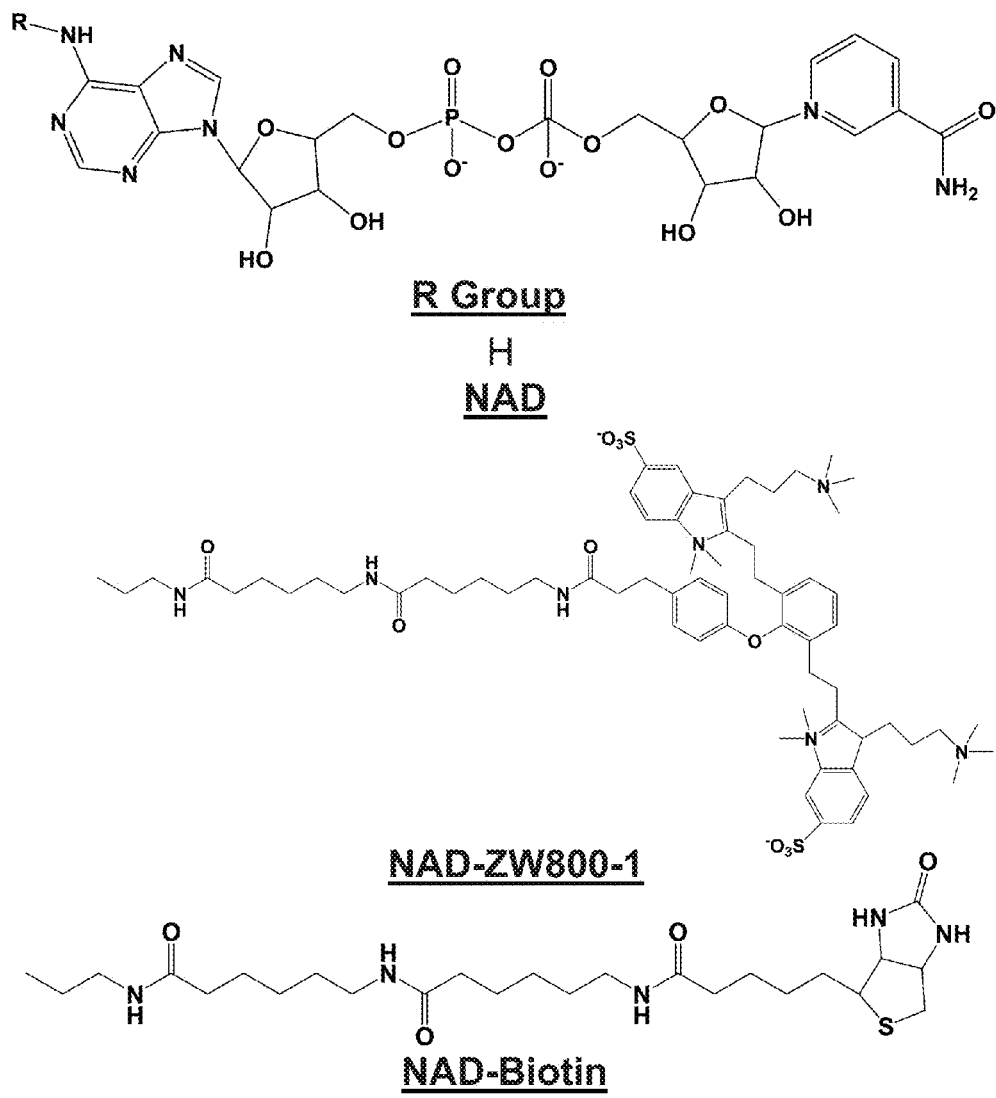
FIGS. 3A and 3B illustrate the assessment of PARP-1 substrate potential of commercially available probes.
Figure 3B:
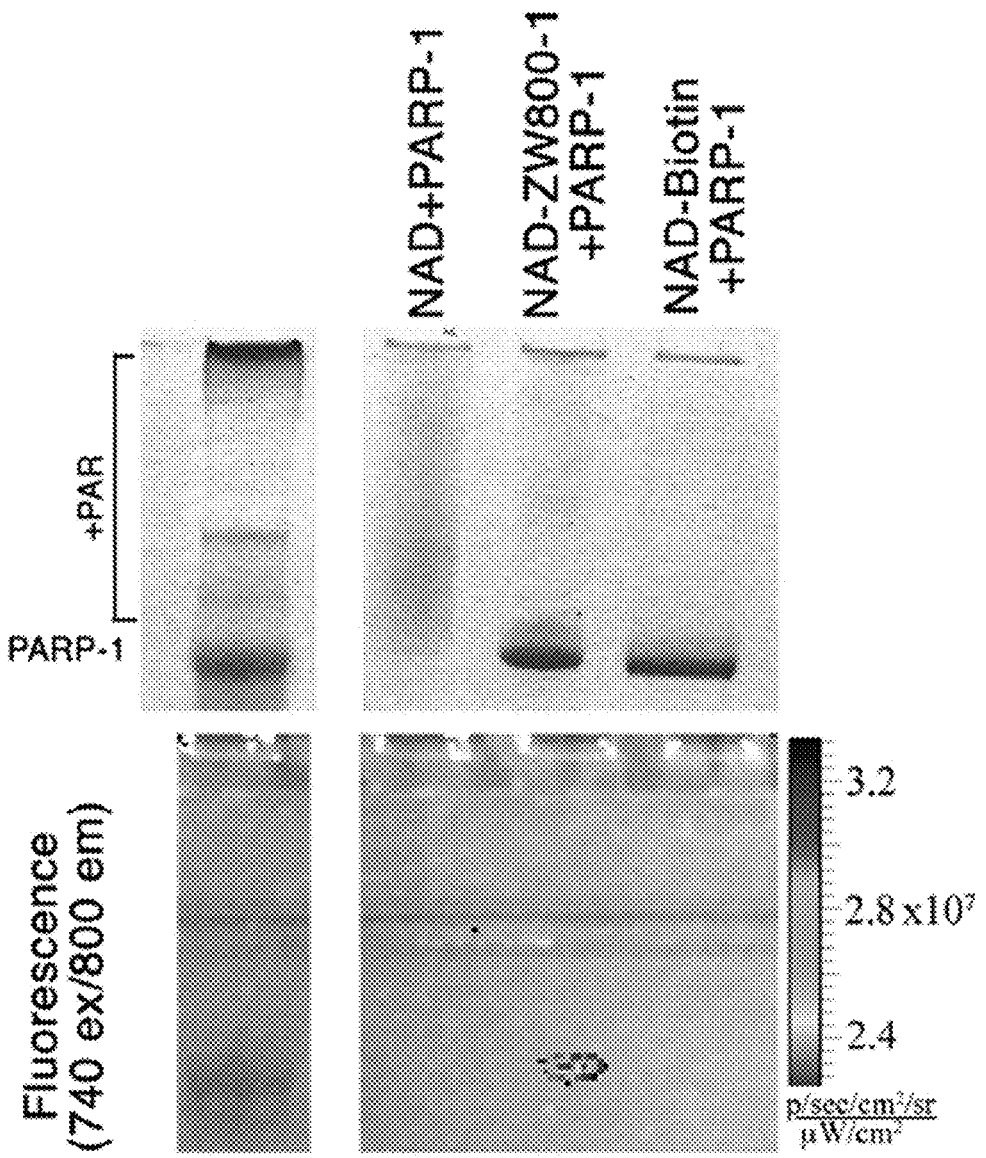
Figure 4A:
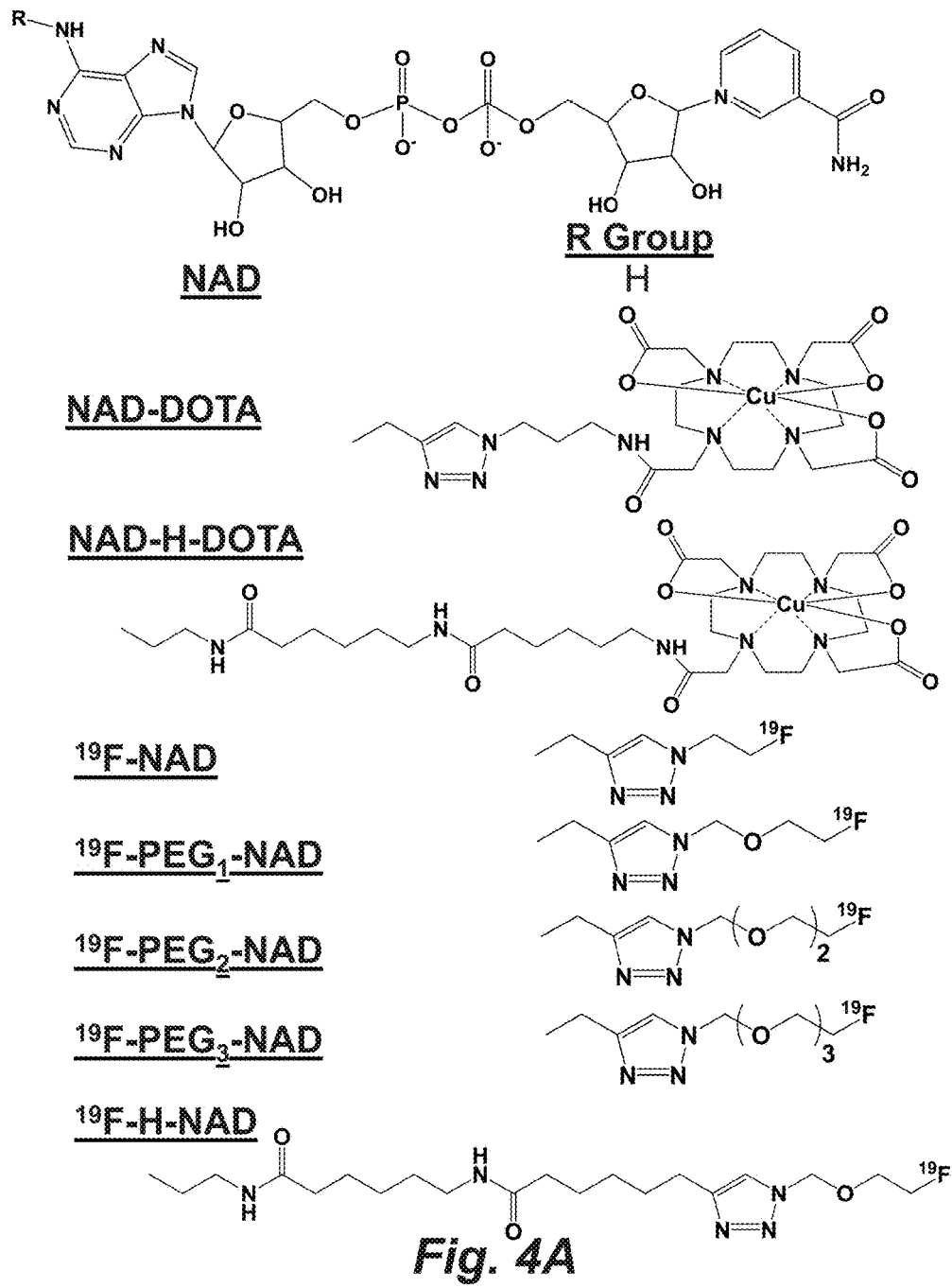
FIG. 4A illustrates novel substrate-based PARP-1 probes assessed for in vitro PARP-1 activity and PARG-mediated degradation of PAR.
Figure 4B:
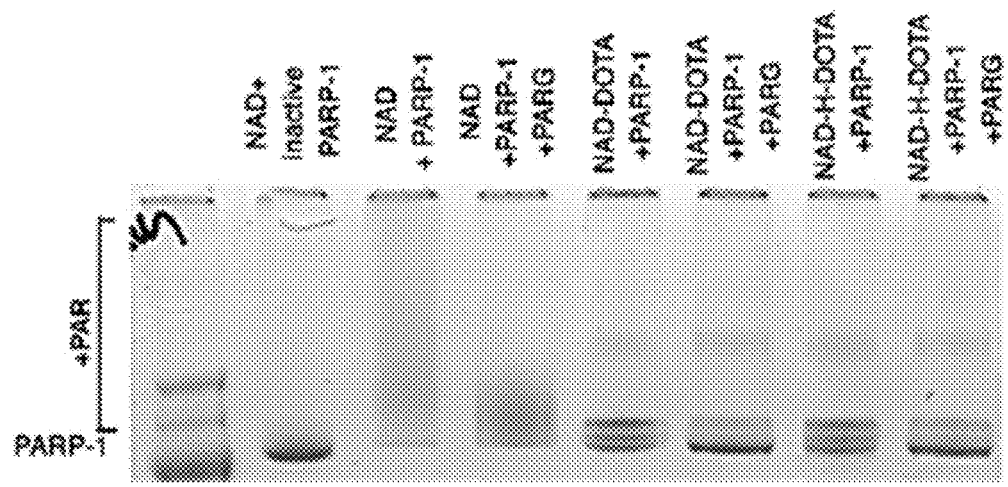
FIG. 4B illustrates a gel showing activities for DOTA (Cu)-containing probes with and without PARG.
Figure 4C:
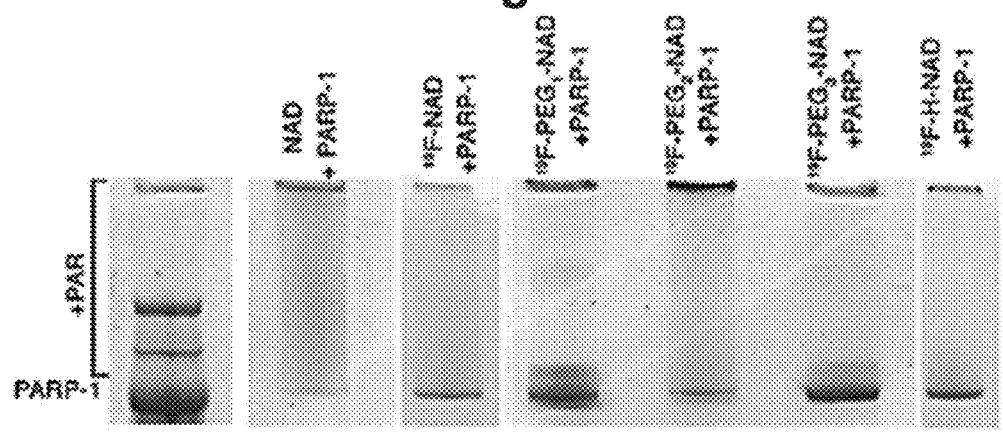
FIG. 4C illustrates a gel showing activities of $^{19}$F-labelled probes with and without PARG.
Figure 4D:
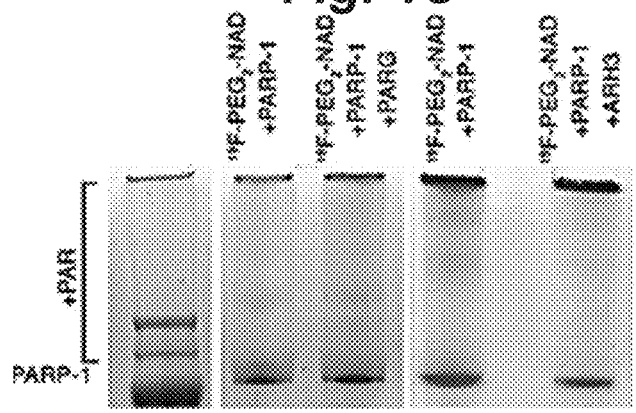
FIG. 4D illustrates a gel showing a pegylated $^{19}$F-labelled probe (PEG2) and resistance to degradation by PARG and ARH3 enzymes.
Figure 5:
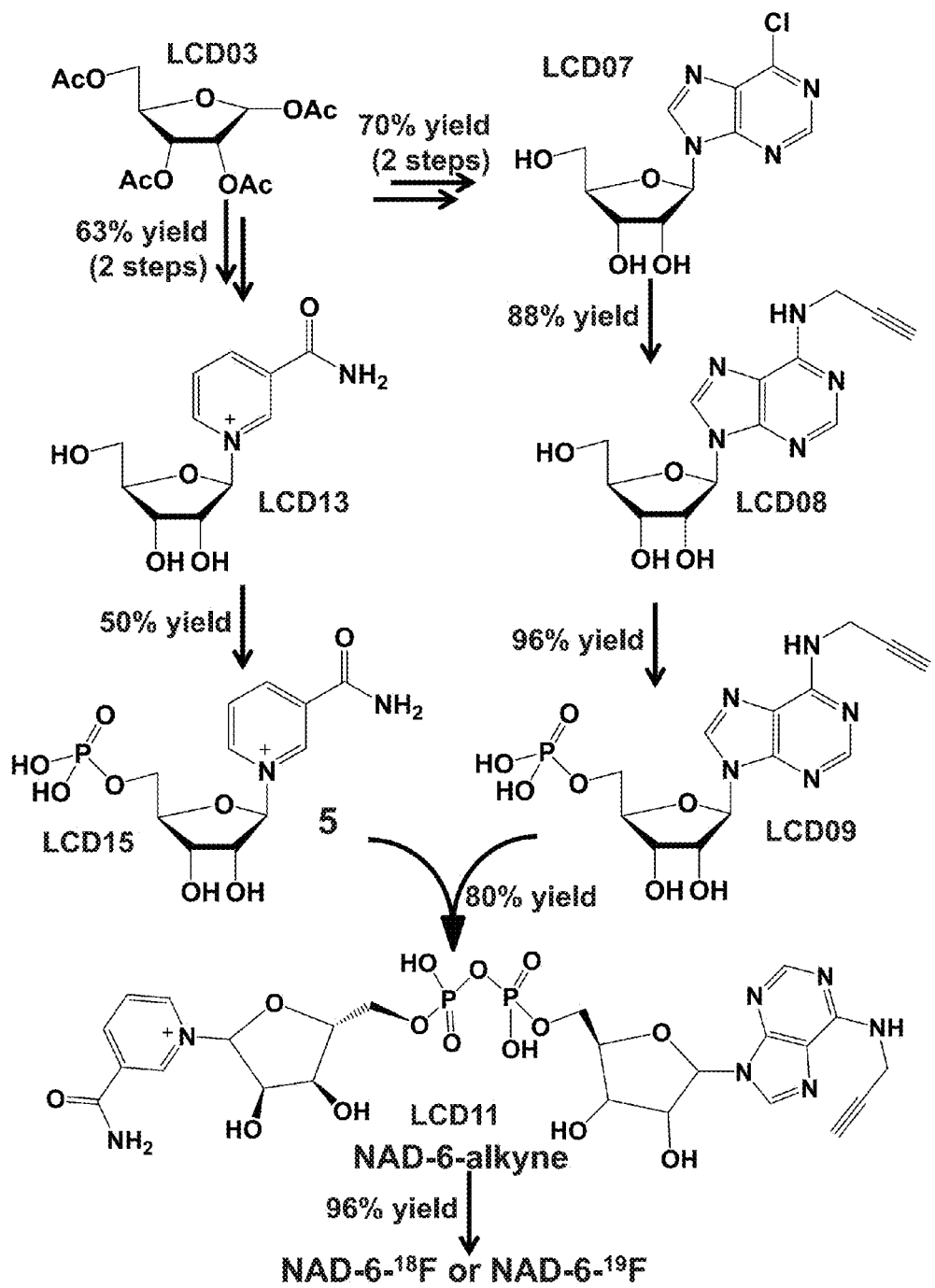
FIG. 5 illustrates a schematic for the synthesis of embodiments of the PARP-1 activity probes of the disclosure.
Figure 6A:
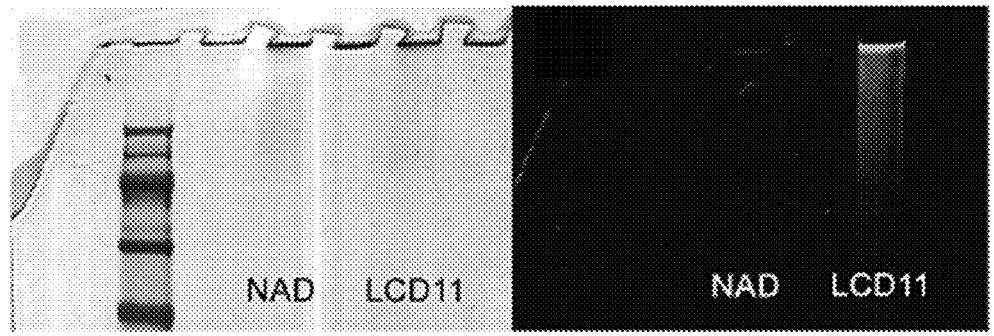
FIG. 6A illustrates the incorporation of an alkyne-modified NAD in PAR in vitro. Brightfield (left panel) and fluorescent (right panel) images of gel showing in vitro reaction of PARP-1 with NAD and LCD11 (alkyne-modified probe). Reactions were run, stopped, and azide-fluorescein was conjugated to both samples using copper-catalyzed click chemistry prior to running gel.
Figure 6B:
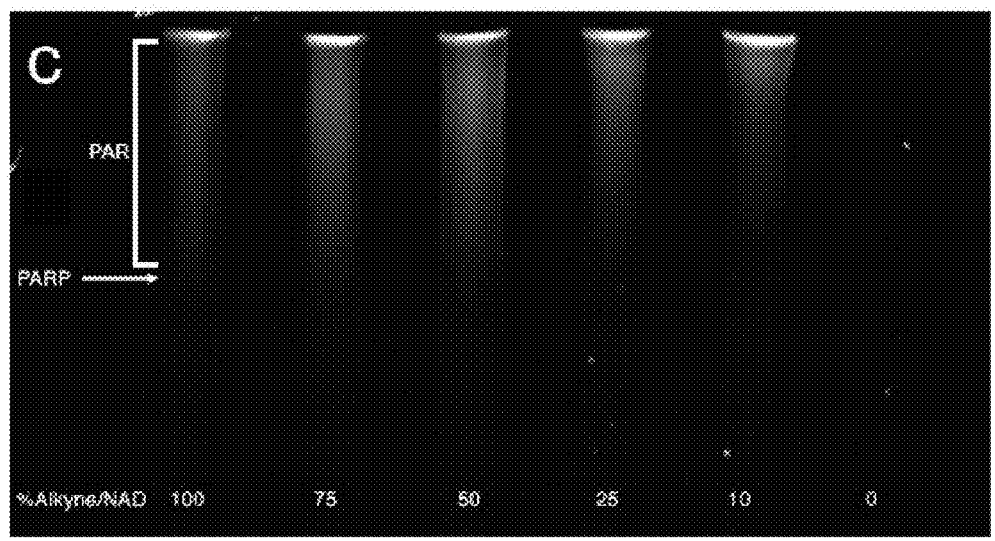
FIG. 6B illustrates a gel showing that at low percentage ratios of alkyne probe to NAD incorporation into high molecular weight PAR occurs.

The PET probes of the disclosure are sensitive to the activity of PARP-1. This is an important distinction since it is the active fraction of total PARP-1 protein that correlates with the extent of DNA damage and the positive response of these cells to therapy and not the total PARP-1 protein levels (Ossovskaya et al., (2010) *Genes Cancer* 1: 812-821). Accordingly, PARP-1 represents a unique target for the design of a substrate-based imaging probe due to its normal function as a polymerase (FIGS. 1A and 1B).

Upon activation, PARP-1 rapidly catalyzes protein ribosylation with the endogenous cellular energy molecule, nicotinamide adenine dinucleotide (NAD) (FIG. 1A) thereby forming poly(ADP ribose) (PAR) polymers as much as 200 units long (FIG. 1B) (Burkle, A. (2001) *Chembiochem.* 2: 725-728). Accordingly, the action of PARP-1 can be advantageously employed so that a substrate-based probe can be assembled into long polymers of reporter molecules, enhancing the local concentration of positron emitter at the site of polymerization and hence amplifying the detectable signal. The net effect is for the prolonged retention of the PARP-1 PET probe in tumor tissue responding to applied therapy, but clearance of otherwise unactivated tracer and enhancing the contrast between the PET signal derived from the active PARP-1 and that produced by tissues not having PARP-1 activity or lower levels. A second advantage of the PET probes of the disclosure stems from their design as substrates of PARP-1, permitting the detection of PARP-1 activity levels through enzyme-catalyzed polymerization that correlate to therapy-induced DNA damage.

It is further contemplated that monitoring a therapeutic response by PARP-1 activity imaging can be applied to a broad, clinically useful range of therapeutics, including, but not limited to, radiation therapy and commonly employed chemotherapies for cancer (e.g. anthracyclines, cyclophosphamide, etc.) (Zong et al., (2004) *Genes Dev.* 18: 1272-1282). PARP-1 is unique as an imaging target as it represents a point of convergence of cell signaling for multiple therapeutic response pathways, enhancing the resolution and sensitivity of therapeutic response monitoring (Aboagye E. O. (2010) *Br. J. Radiol.* 83: 814-822; Dent & Bristow (2011) *J. Clin. Oncol.* 29: 2130-2132). Additionally, this role of PARP-1 can also be exploited for the individualization of cancer treatment such as for, but not limited to, breast cancer by determining the DNA repair status of the tumor prior to the first round of therapy (Dent & Bristow (2011) *J. Clin. Oncol.* 29: 2130-2132). Thus, patients with DNA repair-deficient tumors are better suited to DNA-damaging therapies, while these same therapies would be less effective against tumors proficient in DNA repair. Accordingly, the PARP-1-sensitive PET probes of the disclosure can be usefully applied as a biochemical marker of early therapeutic response, as well as a criterion for patient stratification and cancer therapy individualization. With both pieces of information, the PARP-1-sensitive probes of the disclosure can allow a clinician to tailor the therapy of a patient to his or her specific disease.

The present disclosure, therefore, encompasses embodiments of a small molecule tracer for positron emission tomography (PET) imaging of the enzyme activity of PARP-1 that is responsible for DNA-damage sensing and critically involved in radiation therapy and some chemotherapy response mechanisms. Due to this central biological role, PARP-1 is a target for new chemical entities in clinical trial. The imaging agents of the disclosure are suitable to be applied to measure PARP-1 activity for the study of fundamental biological processes, for the monitoring of radiation therapy response at early time points after radiation (less than 24 h), as the first in vivo endpoint for the assessment of investigational PARP-1 inhibitor drugs, and as a means of selecting patients who may respond to PARP-1 inhibitor therapy.

Figure 7A:
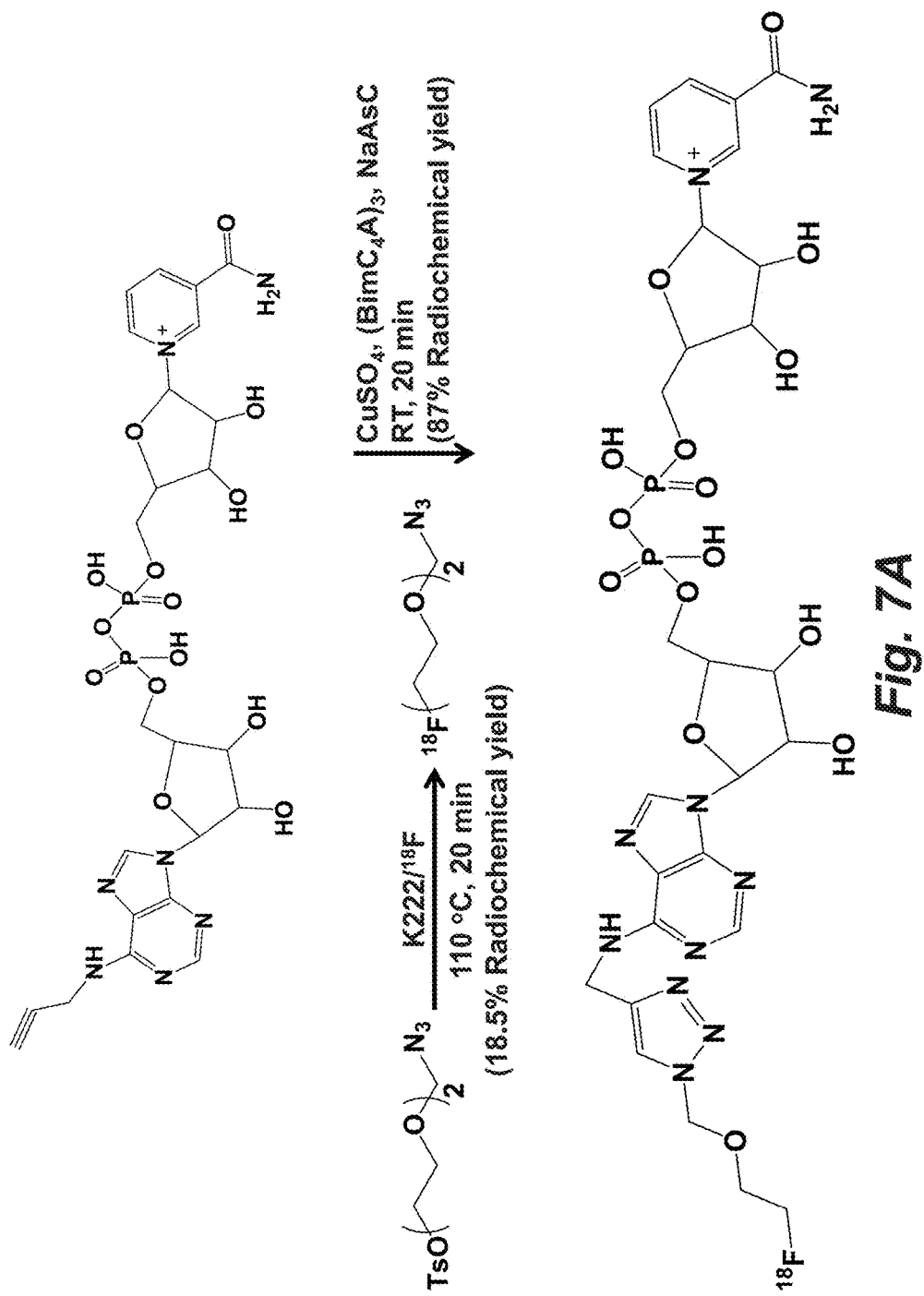
FIGS. 7A-7D illustrate the radiochemical synthesis and in vitro validation of $^{18}$F-PEG2-NAD.
Figure 7B:
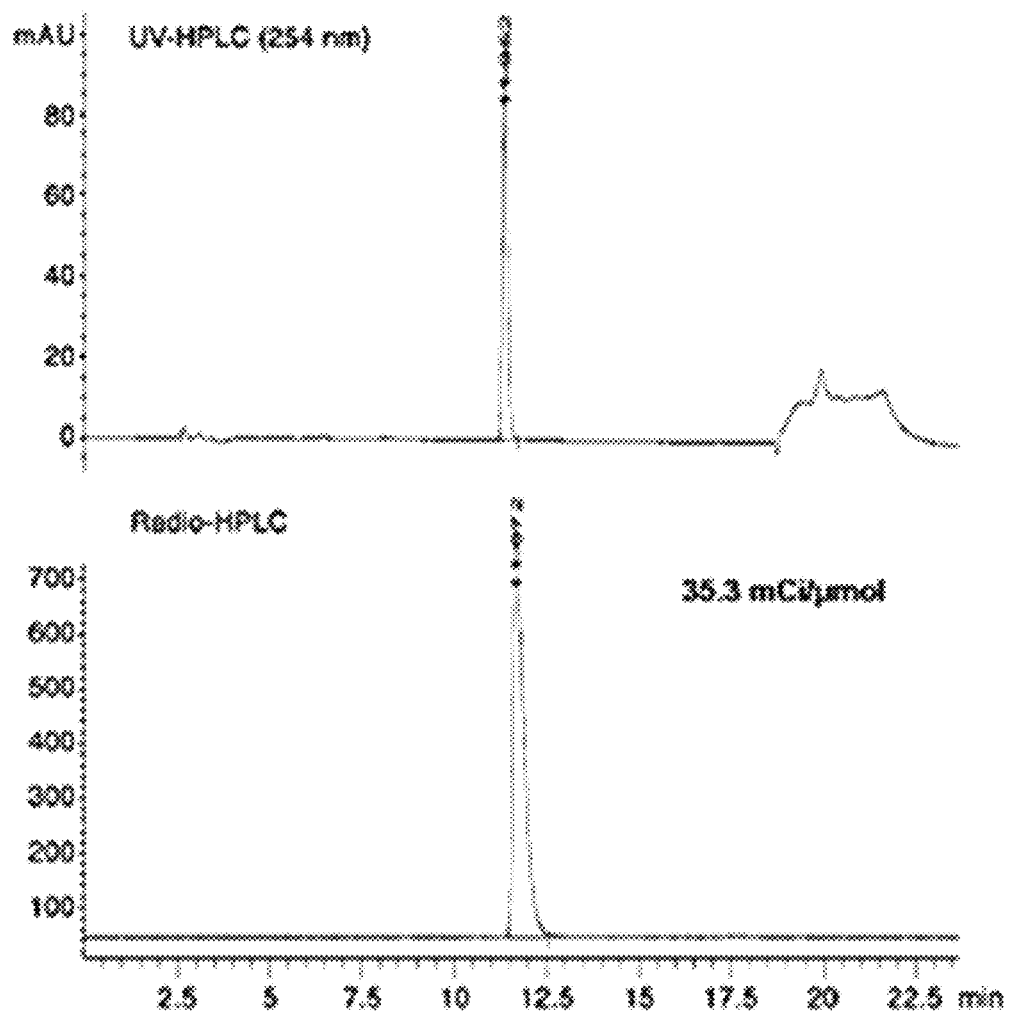
Figure 7C:
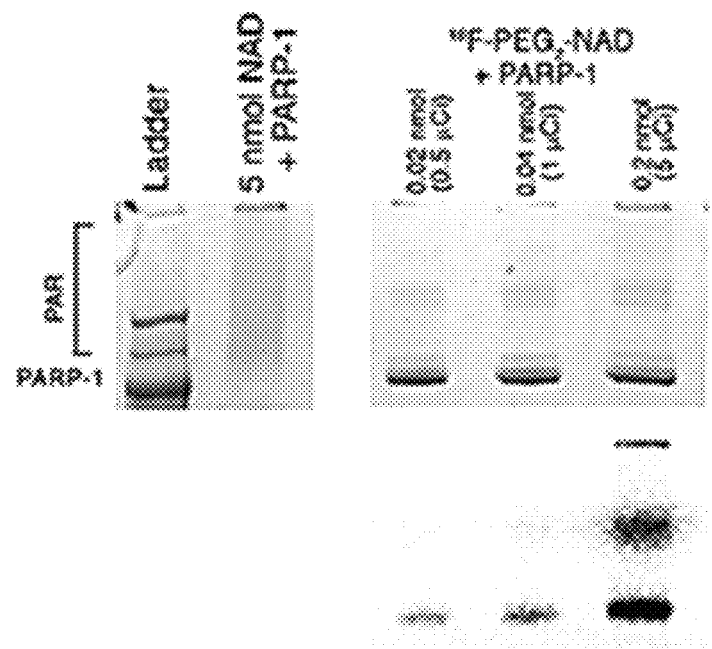
Figure 7D:
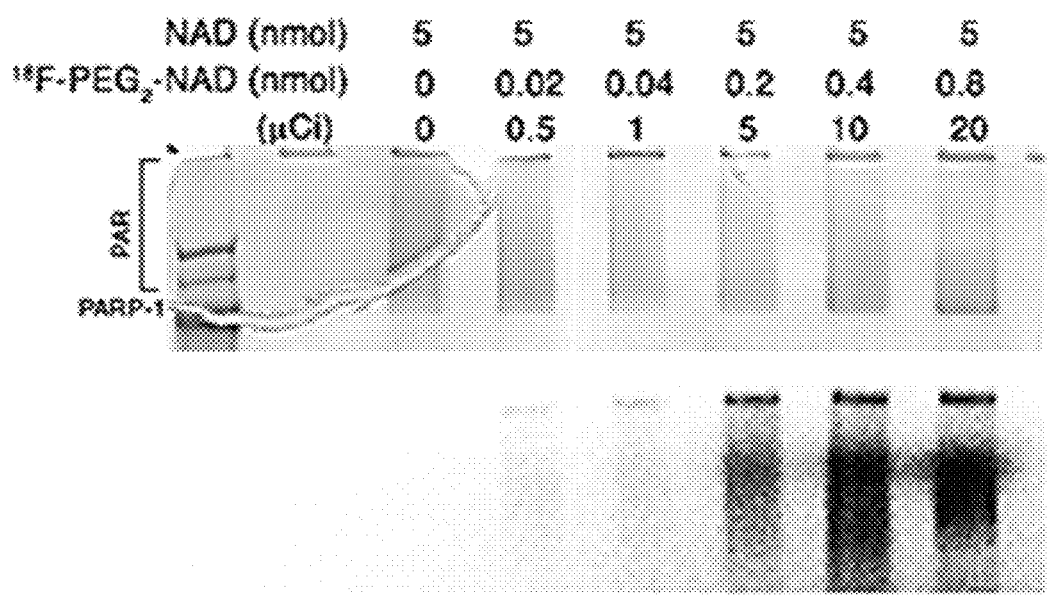
Figure 8:
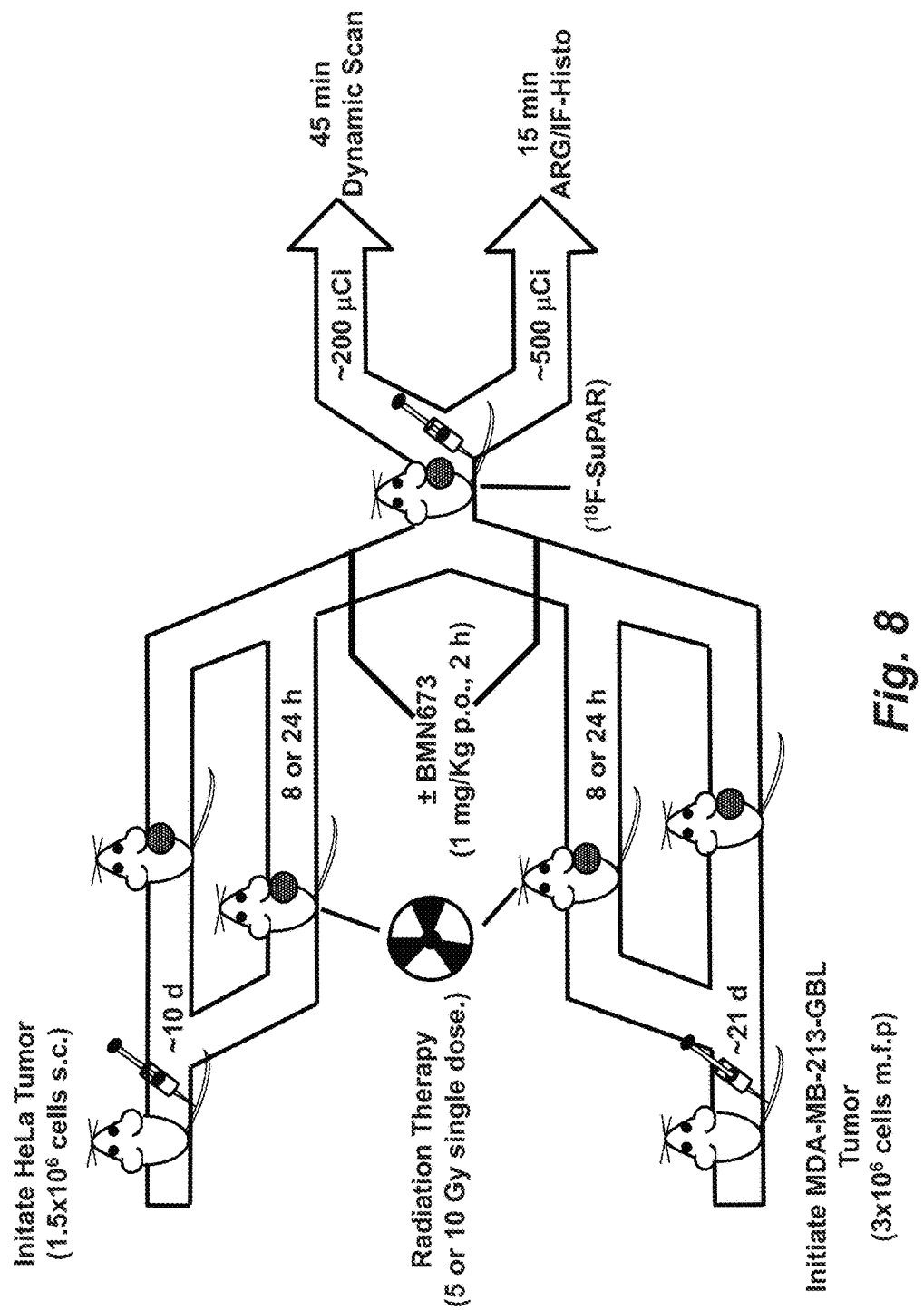
FIG. 8 illustrates a schematic showing animal studies performed with $^{18}$F-PEG2-NAD (Substrate-based PARP-1 Activity Reporter: $^{18}$F-SuPAR)
Figure 9A:
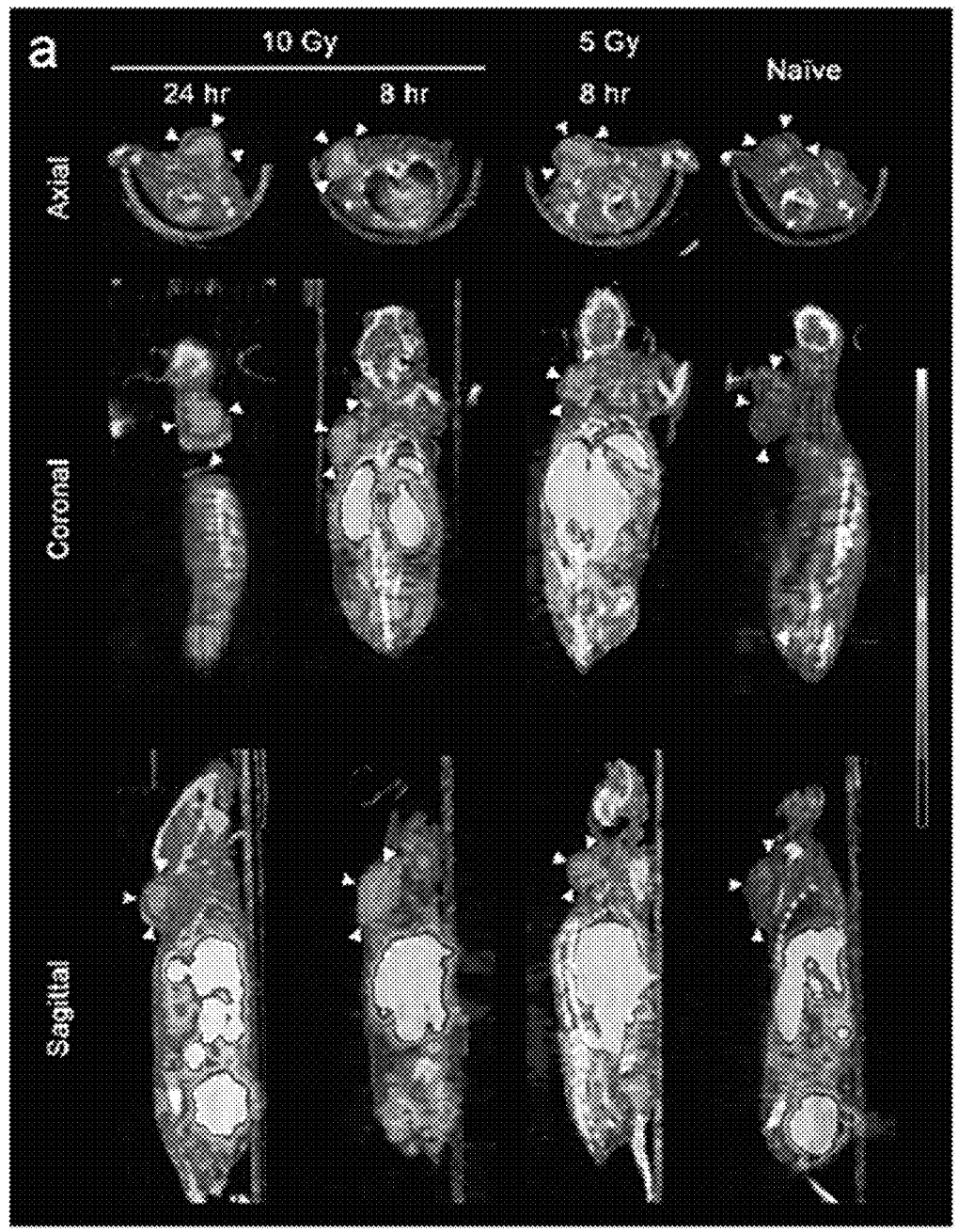
FIGS. 9A-9C illustrate the validation of $^{18}$F-SuPAR in mice bearing HeLa tumor xenografts following radiation therapy.
Figure 9B:
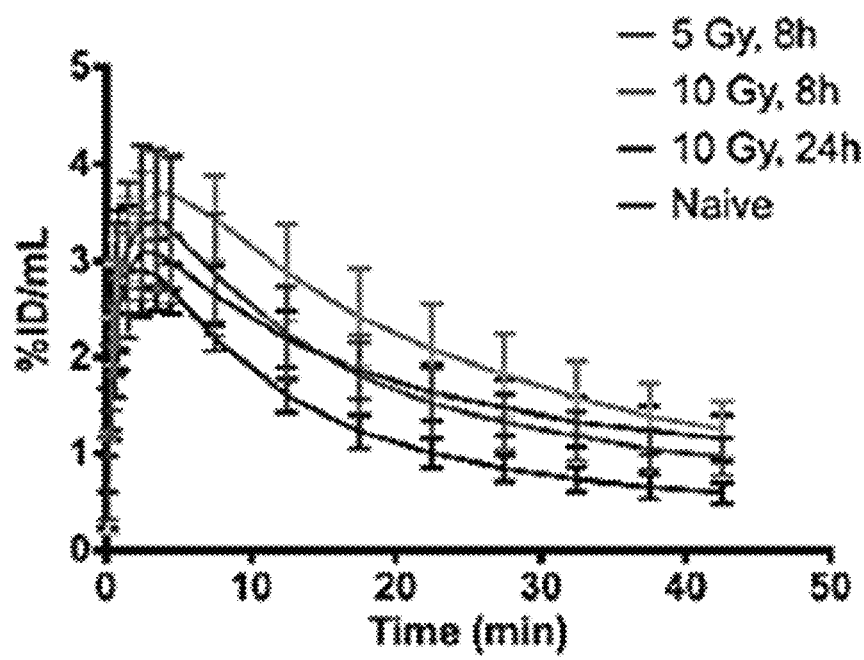
Figure 9C:
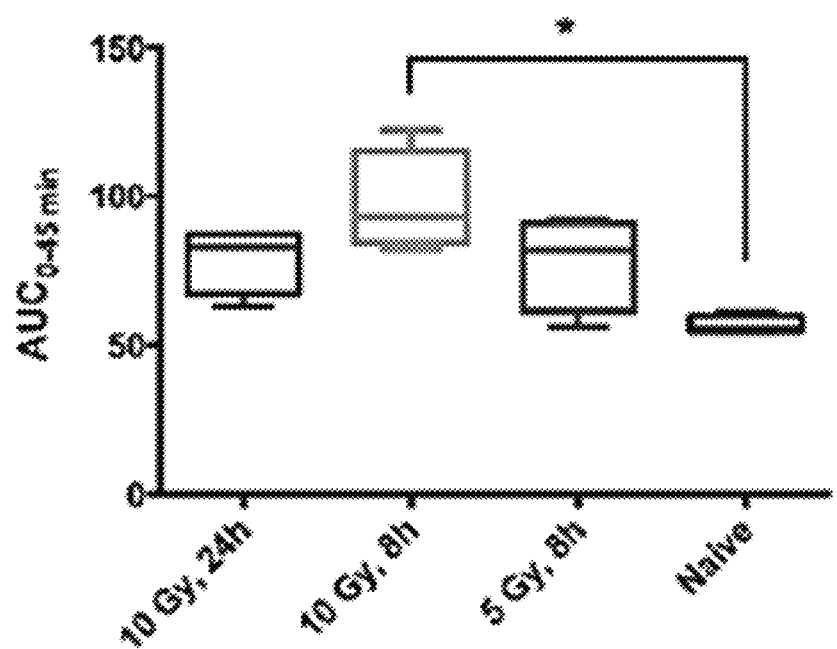
Figure 10A:
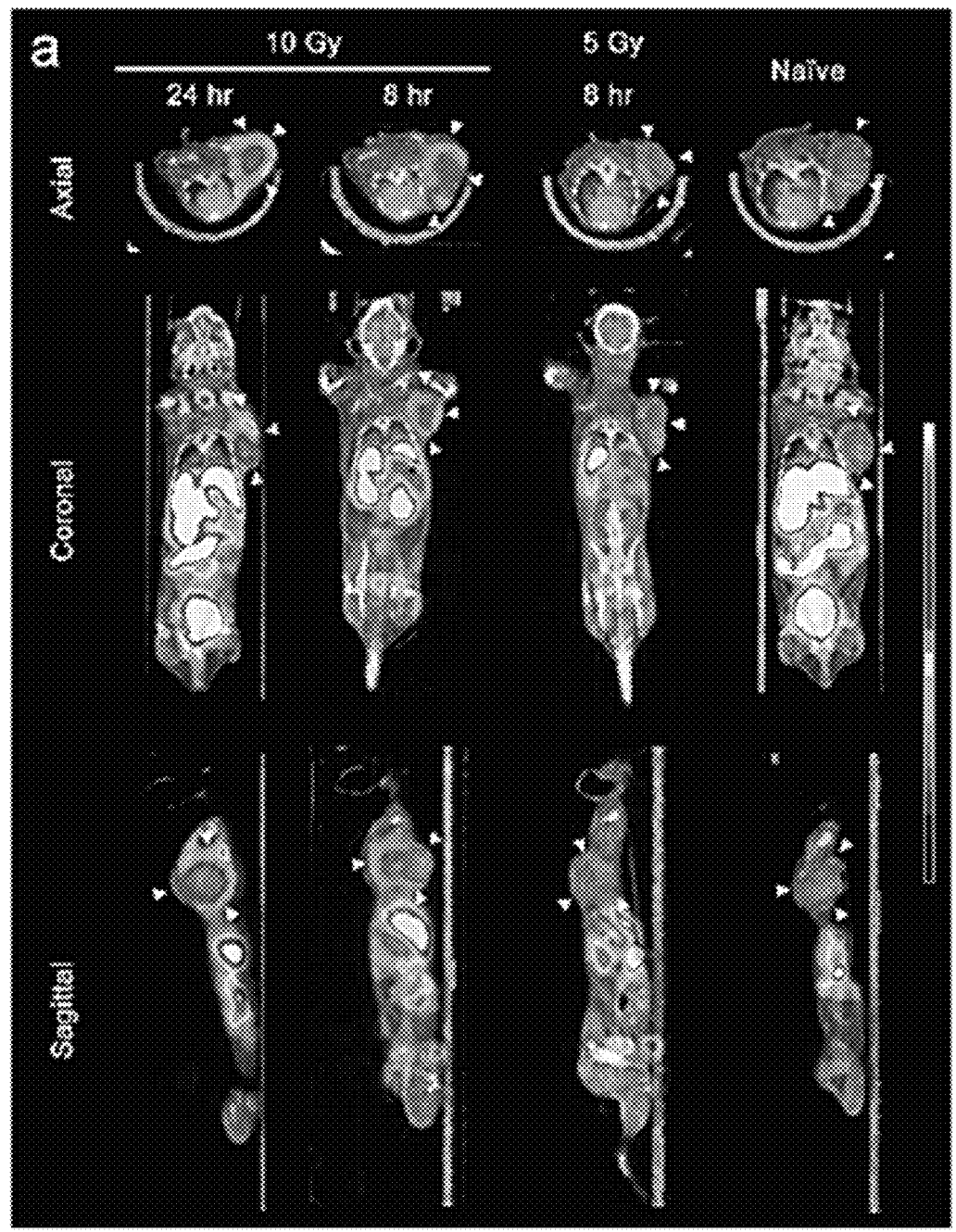
FIGS. 10A-10C illustrate the validation of $^{18}$F-SuPAR in mice bearing orthotopic MDA-MB-231 tumors following radiation therapy.
Figure 10B:
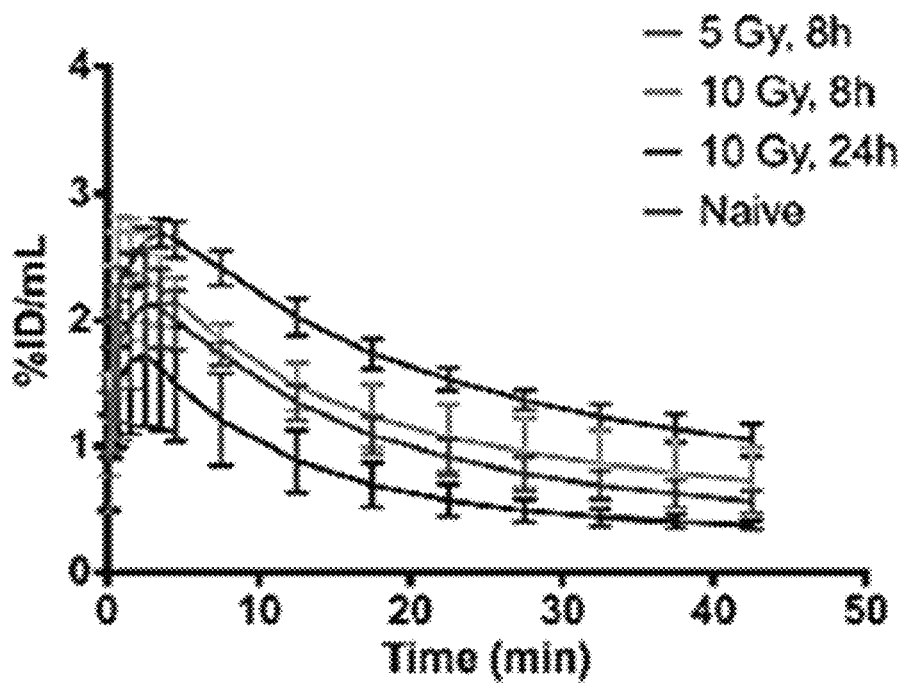
Figure 10C:
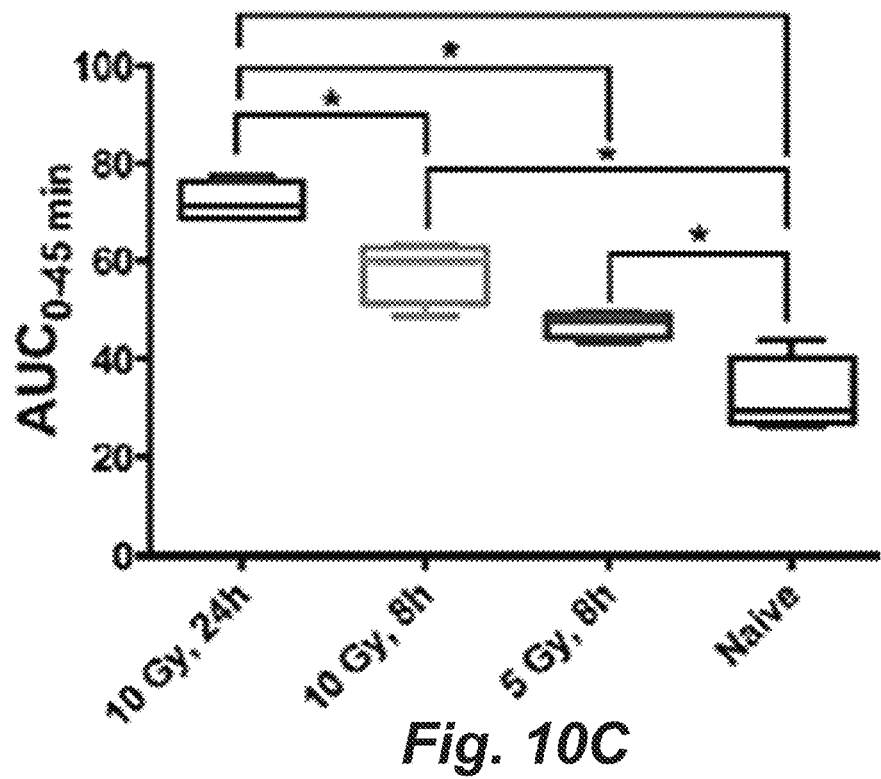
Figures 11A, 11B:
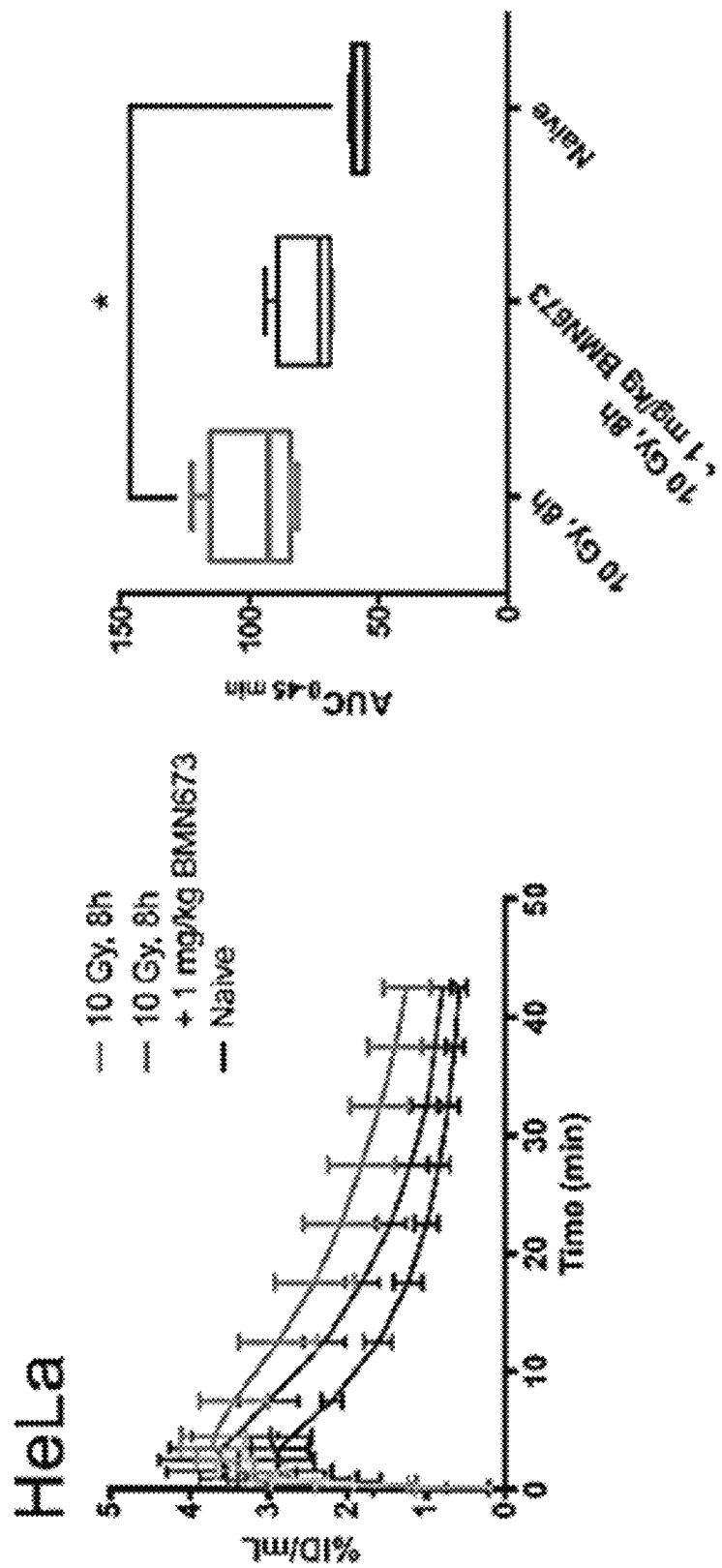
FIGS. 11A-11D illustrate the validation of PARP-1 as target of $^{18}$F-SuPAR following inhibition by BMN673.
Figure 11D:
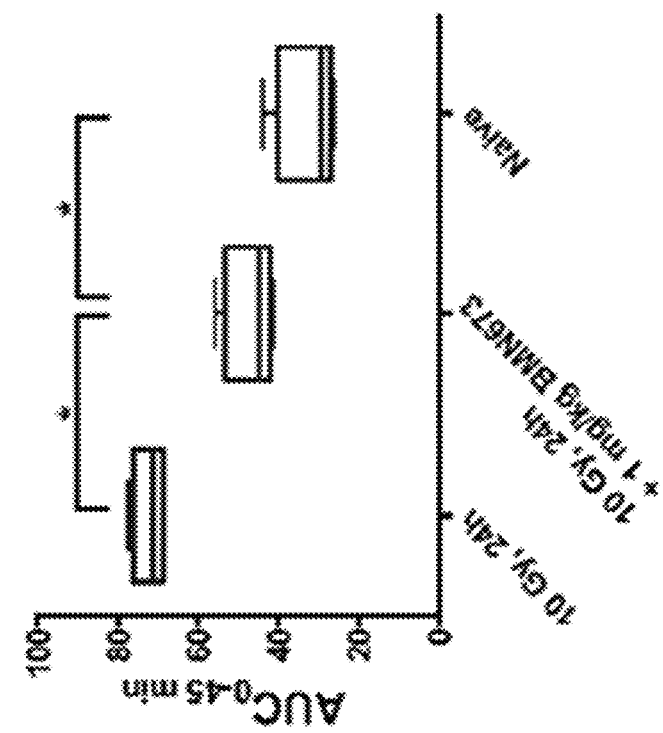
Figure 11C:
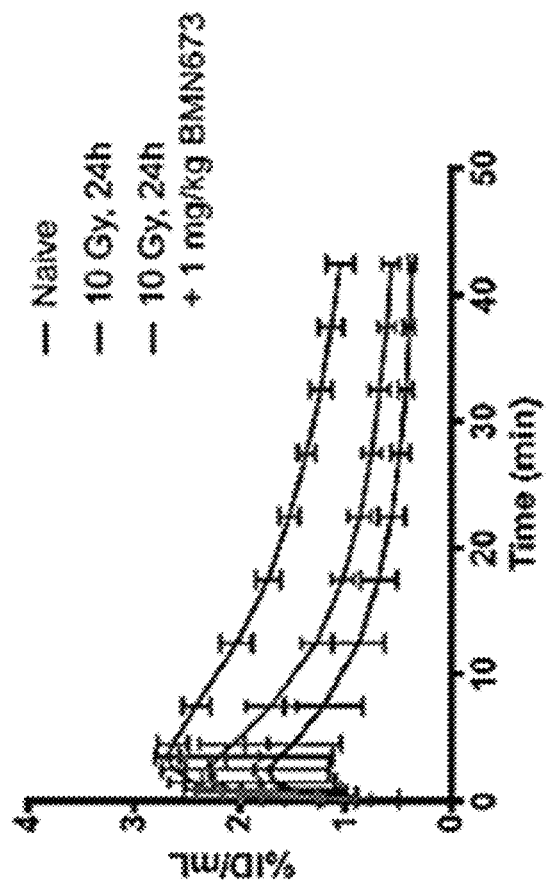
Figure 12:
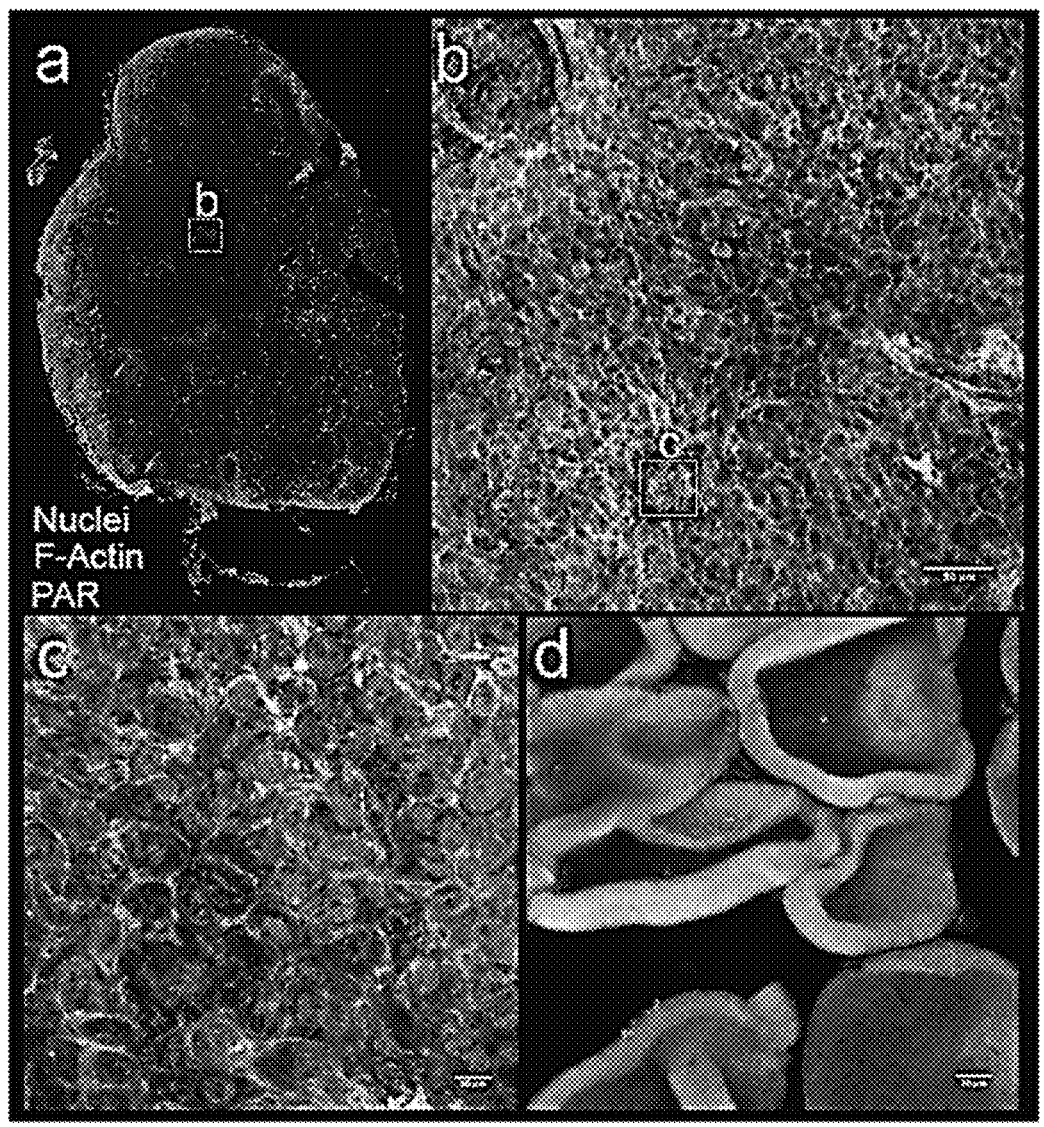
FIG. 12 illustrates digital images showing a microscopy analysis of the subcellular distribution of PAR. Panel a: Scanning epifluorescence imaging of treated MDA-MB-231 (10Gy, 8 hr) showing nuclei and PAR; Panel b: 20× confocal image of the same sample; Panel c: 60× confocal image of the same sample; Panel d: Muscle section from same mouse showing different PAR distribution. Dashed boxes show regions of enlargement.
Figure 13:
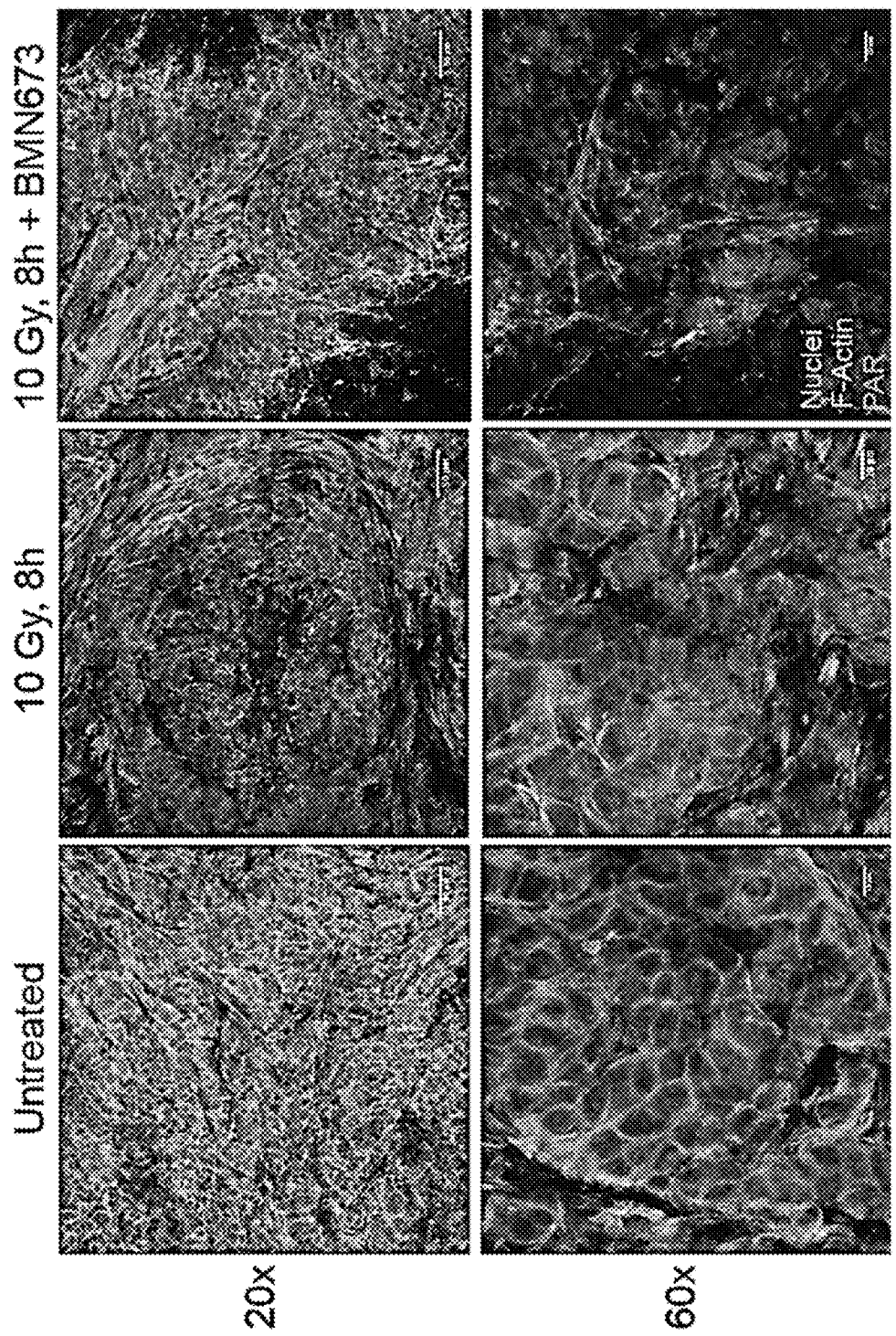
FIG. 13 illustrates digital confocal images of stained HeLa tumor sections with the indicated treatments showing nuclei, F-actin, and PAR.
Figure 14:
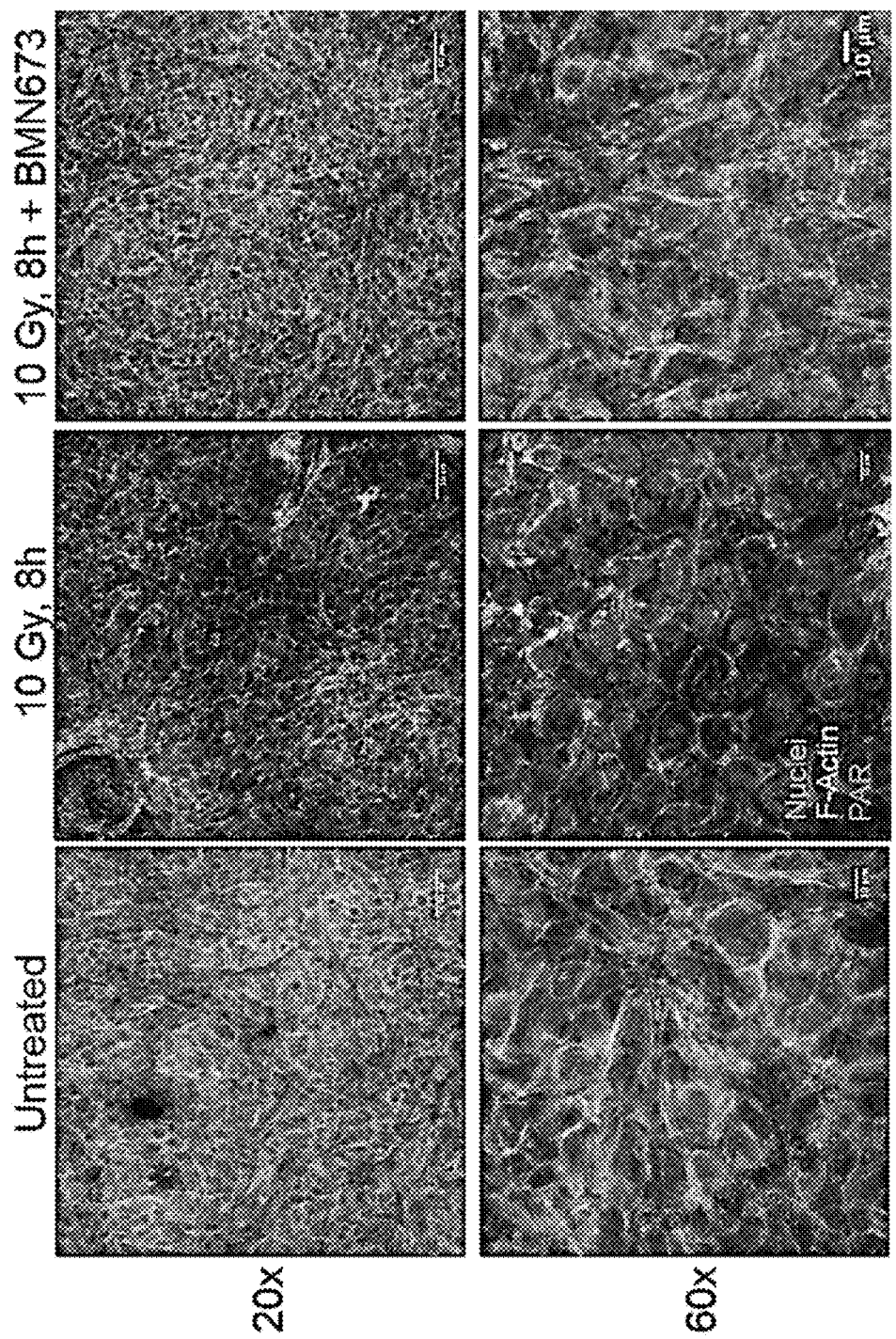
FIG. 14 illustrates digital confocal images of stained of stained MDA-MB-231 tumor sections with the indicated treatments, showing nuclei, F-actin, and PAR.
Figure 15A:
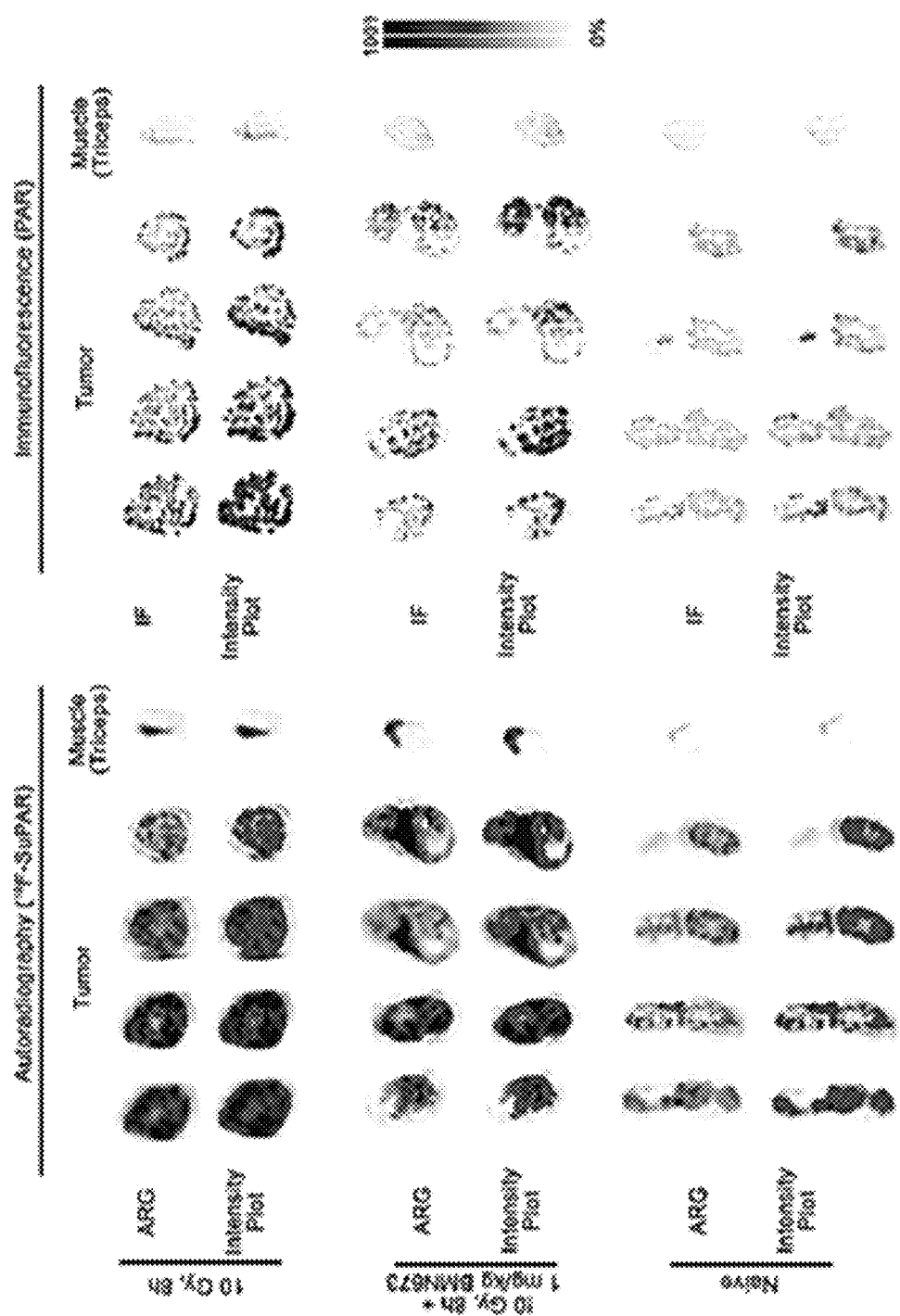
FIGS. 15A-15C illustrate autoradiographic and immunofluorescence imaging of retained $^{18}$F-SuPAR with PAR product of PARP-1 anabolism in HeLa tumors.
Figure 15B:
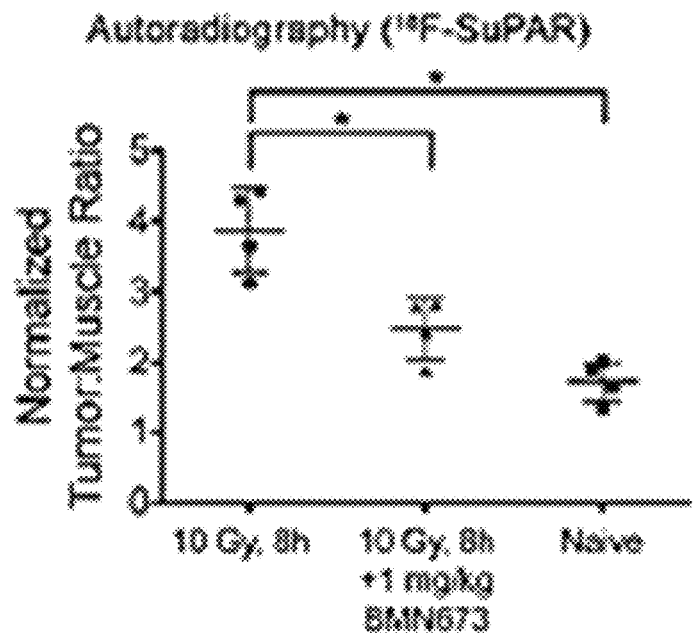
Figure 15C:
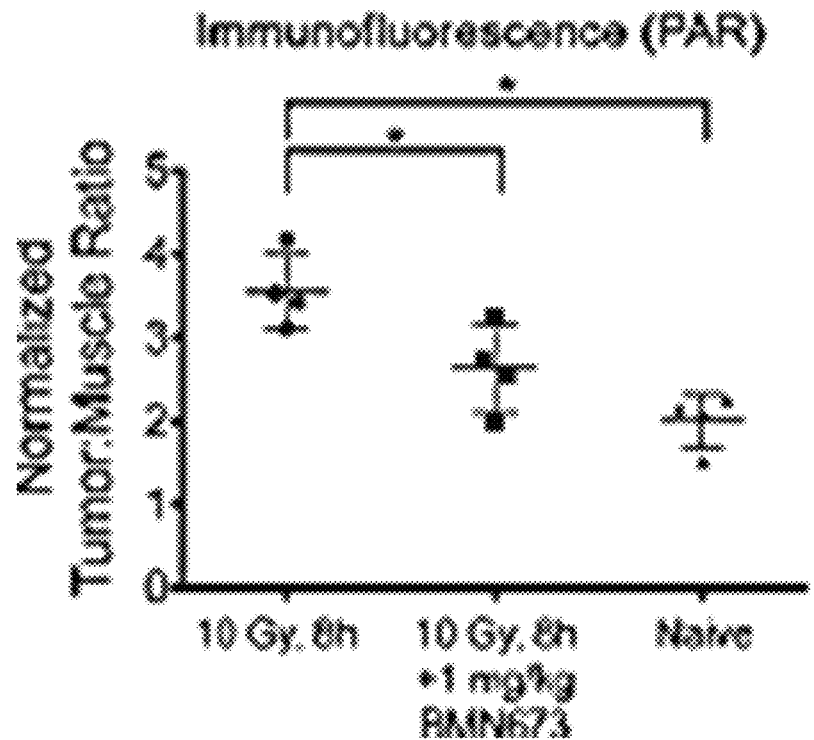
Figure 16A:
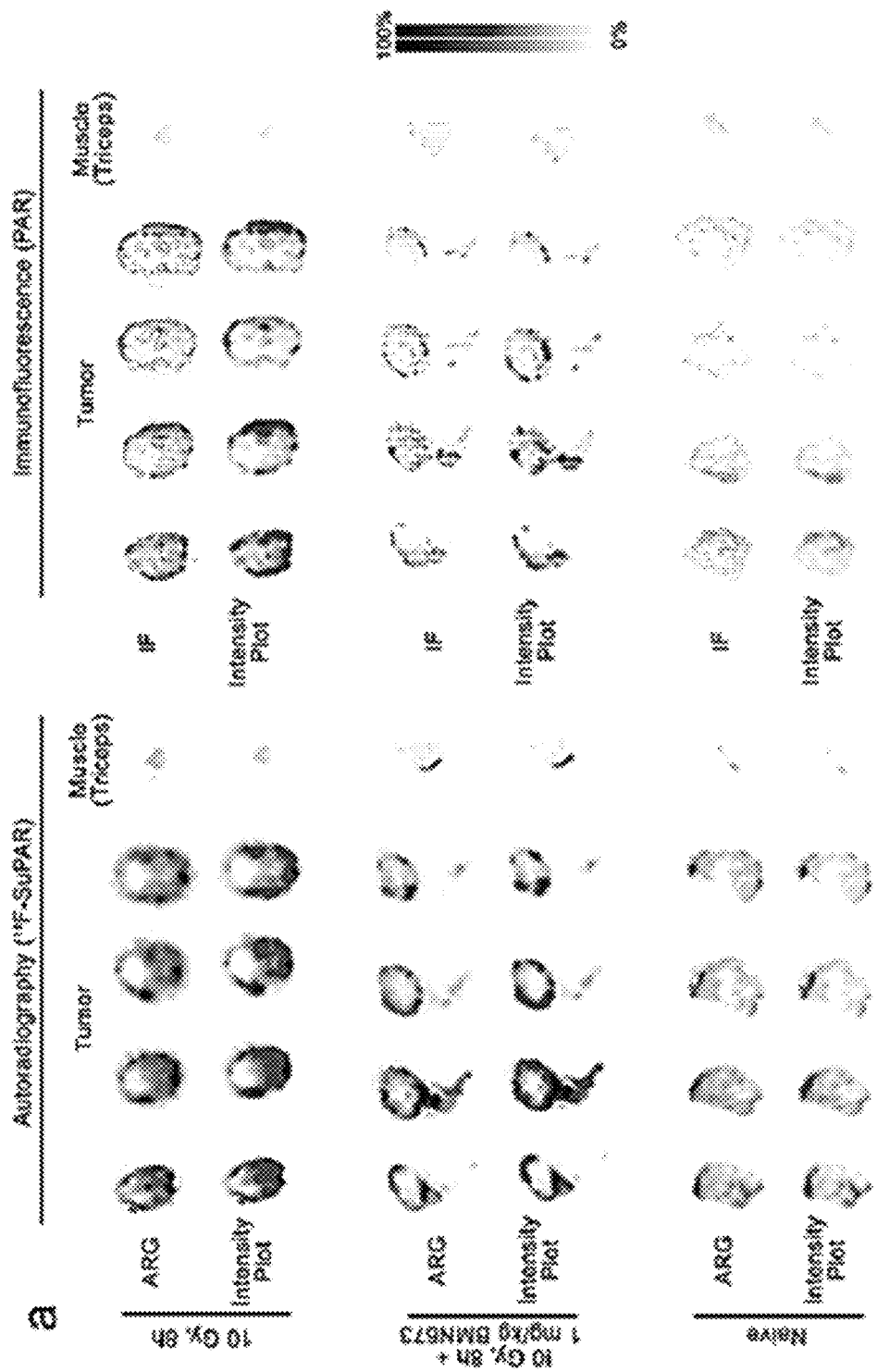
FIGS. 16A-16C illustrate autoradiographic and immunofluorescence imaging of retained 18F-SuPAR with PAR product of PARP-1 anabolism in MDA-MB-231 tumors.
Figure 16B:
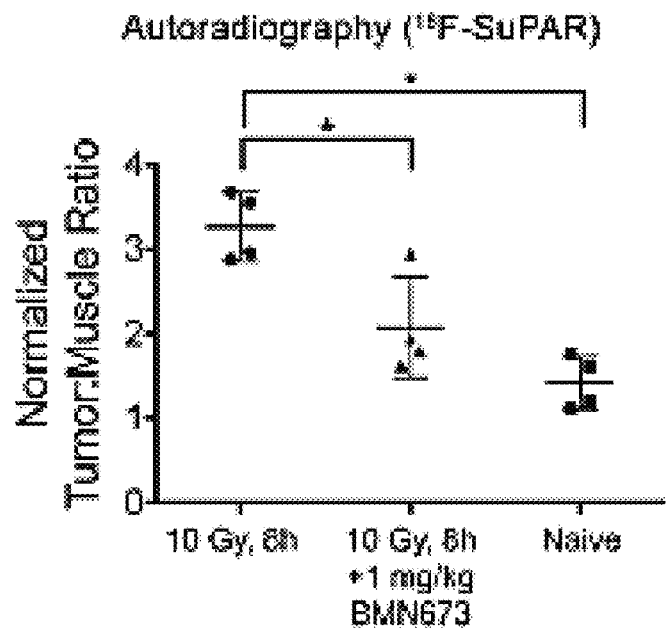
Figure 16C:
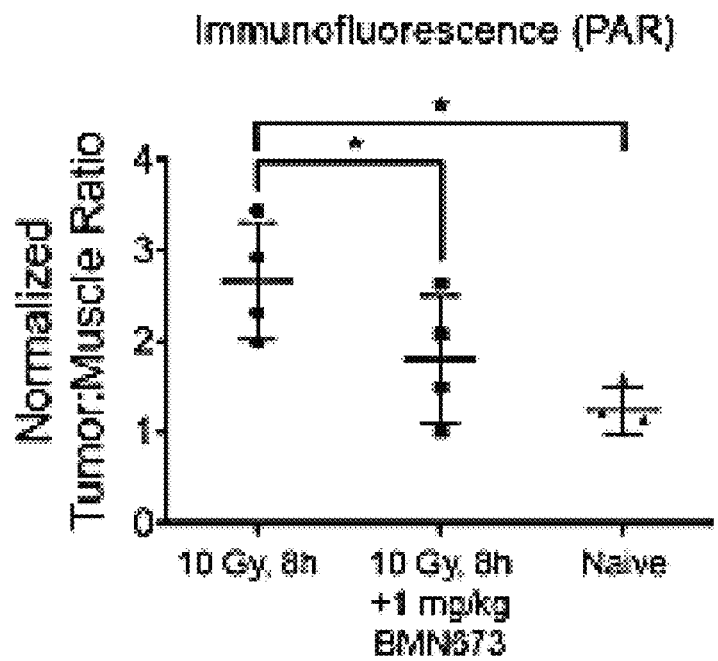
Figure 17A:
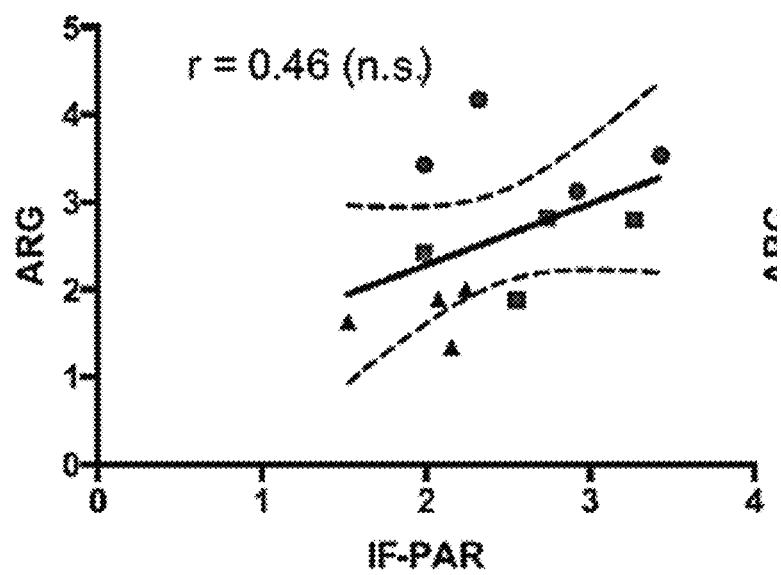
FIG. 17A is a graph illustrating the correlation of $^{18}$F-SuPAR retention (ARG) and production of PAR (IF-PAR) for HeLa tumors. Solid line=regression, dashed line=95% confidence interval.
Figure 17B:
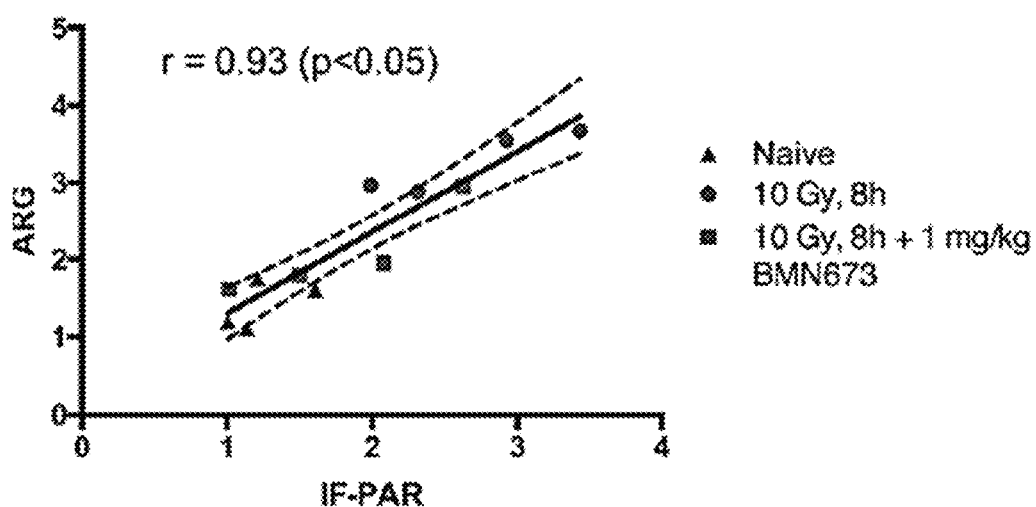
FIG. 17B is a graph illustrating the correlation of $^{18}$F-SuPAR retention (ARG) and production of PAR (IF-PAR) for MDA-MB-231 tumors. Solid line=regression, dashed line=95% confidence interval.
Figure 18A:
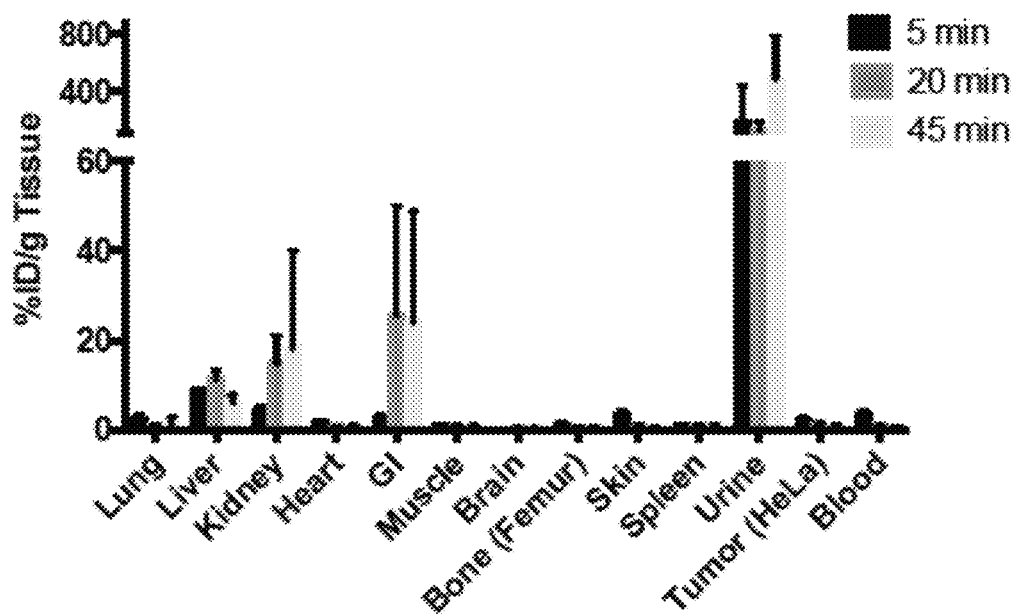
FIG. 18A illustrates the biodistribution of $^{18}$F-SuPAR in HeLa tumor-bearing nude mice in all tissues. (n=4)
Figure 18B:
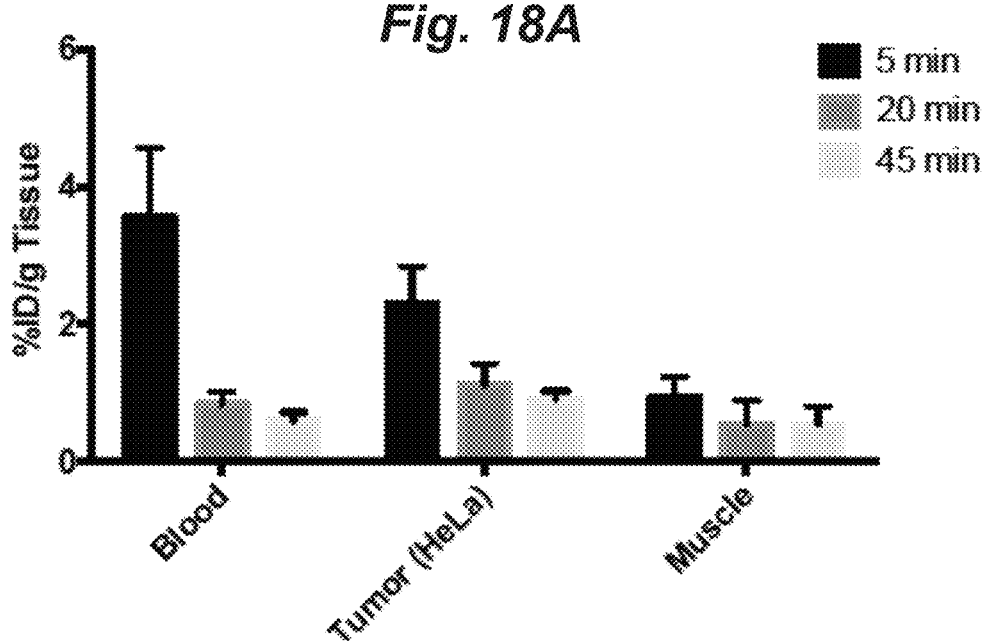
FIG. 18B illustrates the biodistribution of $^{18}$F-SuPAR in HeLa tumor-bearing nude mice in blood, tumor, and muscle alone (bottom). (n=4)
Figure 19:
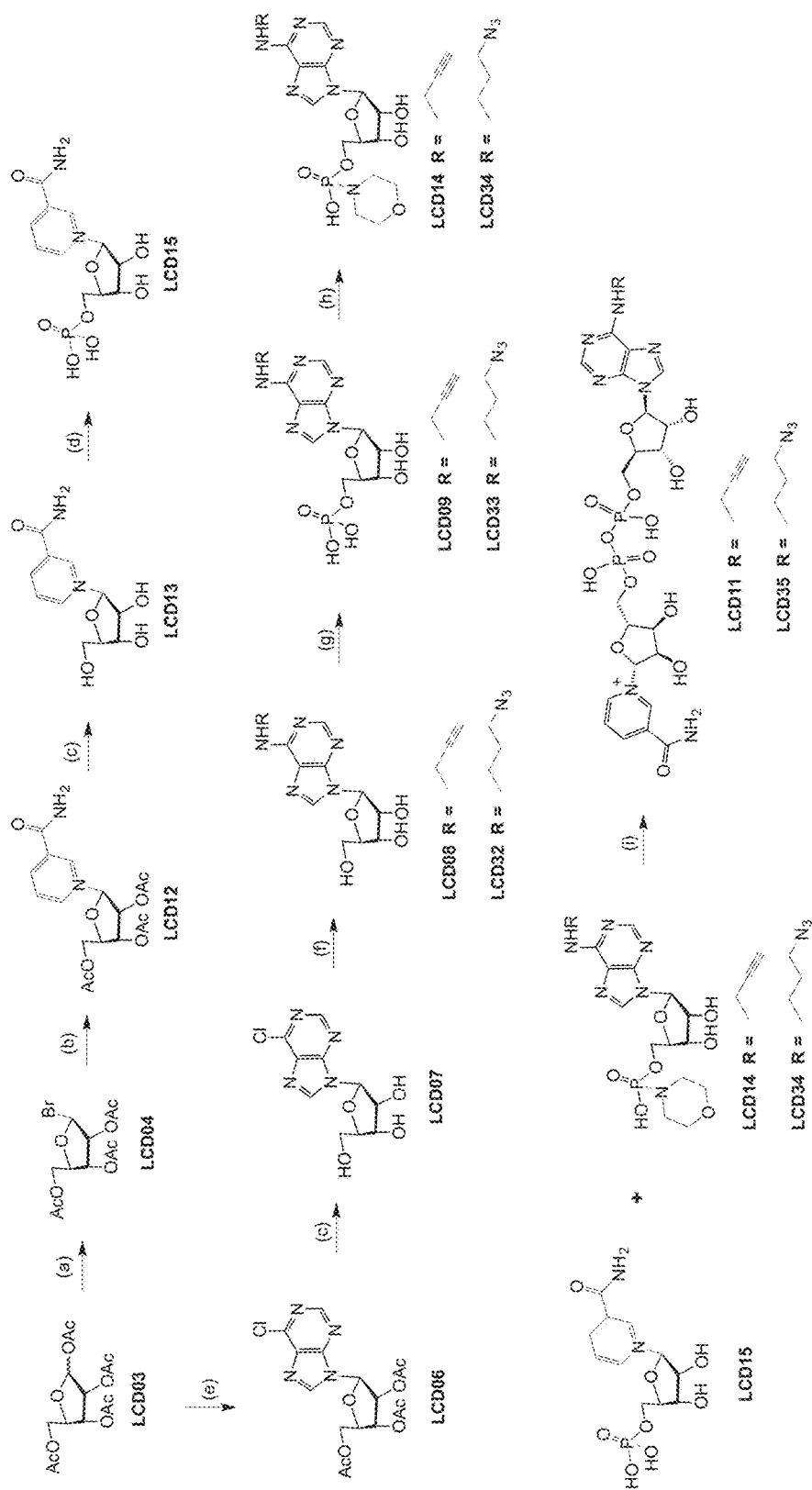
FIG. 19 illustrates Scheme 1, the synthesis of the functionalizable NAD derivatives LCD11 and LCD35.
Figure 20:
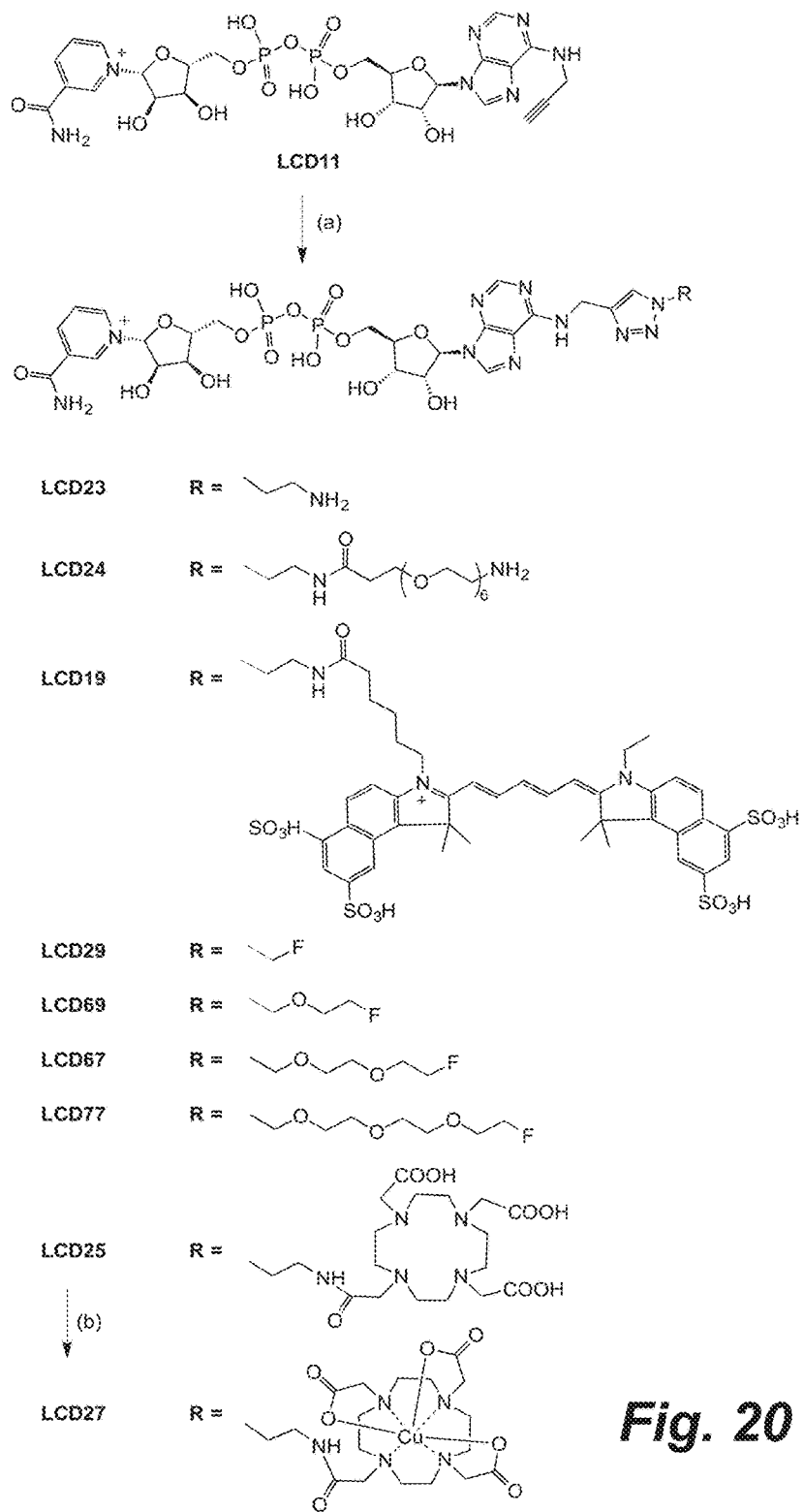
FIG. 20 illustrates Scheme 2, the synthesis of bulky linker LCD11-derived probes.
Figure 21:
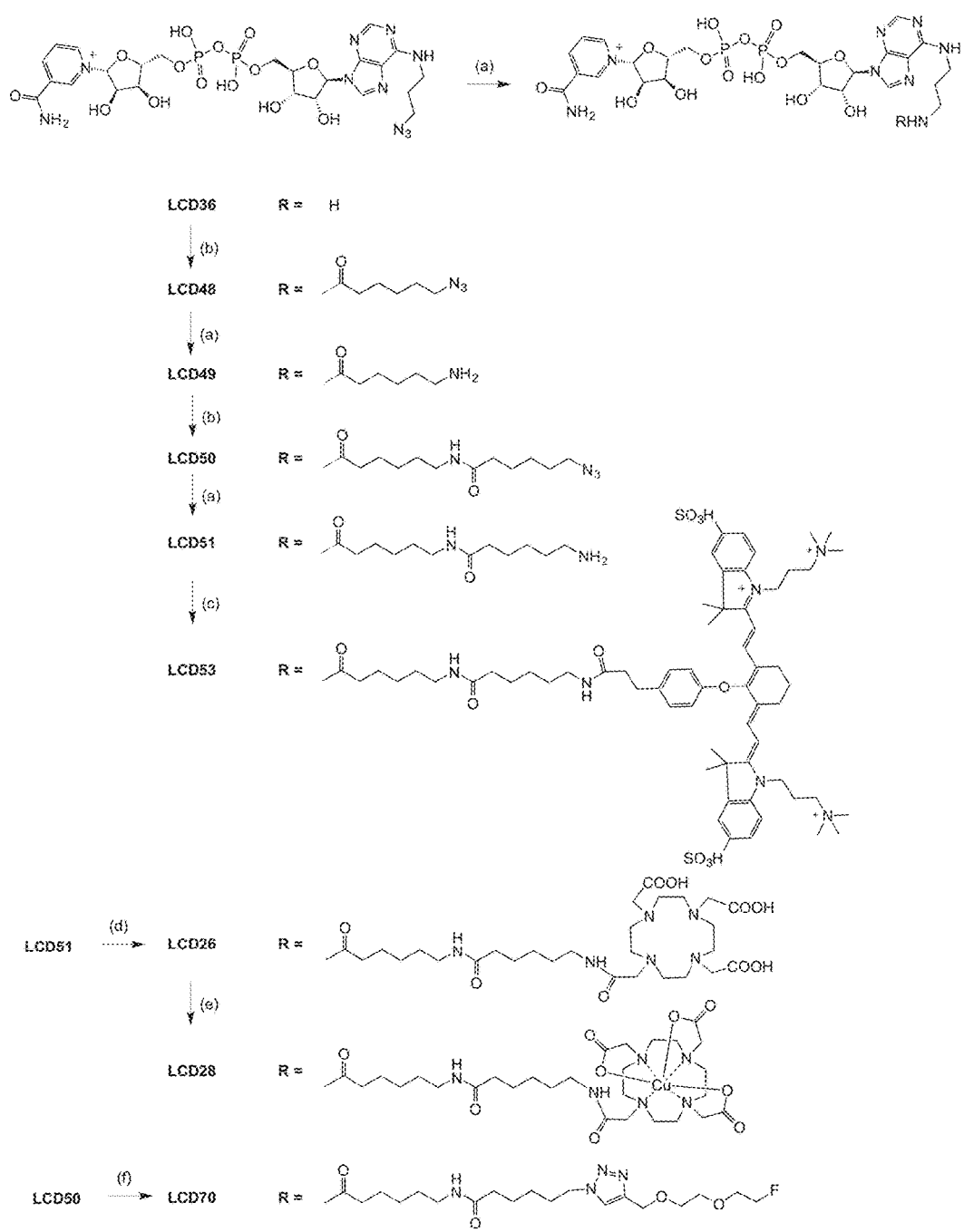
FIG. 21 illustrates Scheme 3, the synthesis of linear linker LCD35-derived probes.

The PARP-1 tracers of the disclosure are derivatives of nicotinamide adenine dinucleotide (NAD), which is the natural substrate for PARP-1. Provided are NAD derivatives that include a linker moiety attached thereto. A scheme for the synthesis thereof is shown in FIG. 19. For derivatives that may be used as precursor molecules, the linker may have a terminal reactive group for the subsequent attachment of a detectable label. In one embodiment, the terminal reactive group is an alkyne (as shown, for example in FIG. 20) and in another embodiment the reactive group is an azide moiety, as shown in FIG. 21. These precursors may be reacted with a variety of labelling moieties. For example, as shown in FIG. 7A, a polyethylene glycol or multimer thereof that has a terminal azide at one end and a PET detectable fluorine at the other, may react with an alkyne-derivatized NAD to generate a 6N-(triazo-PEG2-$^{18}$F)-NAD.

The synthesis schemes of the present disclosure may be readily adapted for the attachment of a variety of labelling moieties, including fluorescent dyes detectable by other than PET scanning. Thus, in one example, the fluorescent dye Cy5.5 may be incorporated as is shown in FIG. 20. Especially advantageous for use in PET and MRI scanning detection systems is the attachment of a chelating agent that allows for the formation of a chelator-metal ion complex.

It is further contemplated that embodiments of the NAD-based compositions of the disclosure may incorporate a chelating moiety that allows incorporation of a metal ion label. Such metal ion labels may be usefully detectable by methods such as MRI, thereby allowing alternative imaging methods to PET. One advantageous chelator, for example, is 1,4,7,10-tetraazacyclododecane-1,4,7,10-tetraacetate (DOTA) that may be complexed with a variety of metal ions or isotopes thereof, including, but not limited to, $^{64}$Cu, $^{48}$V, $^{52}$Fe, $^{55}$Co, $^{94}$mTc, $^{68}$Ga, $^{99}$mTc, $^{111}$In, $^{113}$In and $^{67}$Ga.

One advantageous tracer probe of the disclosure is an efficient analog of NAD that has been labelled by $^{18}$F-radionuclide for PET imaging. It is contemplated, however, that other radionuclides detectable by PET imaging technology can be used in place of $^{18}$F. Previously unknown relationships between NAD modification and PARP-1 substrate potential have been elucidated to synthesize the tracer, 6N-(triazo-PEG2-$^{18}$F)-NAD. This tracer was validated for PARP-1 activity in vivo in two animal models of tumor radiation therapy. A dose-dependence of tracer retention was observed with increasing doses of radiation (0, 5, 10 Gy), and a time-dependence of maximal tracer uptake was observed, which was tumor-type specific. Finally, the probe target was verified as PARP-1 using a highly potent PARP-1 inhibitor. Results were confirmed ex vivo by autoradiography and immunofluorescence analysis of tumor sections.

6N-(triazo-PEG2-$^{18}$F)-NAD and variants thereof are useful for application to basic research, clinical practice, and in the pharmaceutical industry for drug development. The current imaging agent can be applied to measure PARP-1 activity for the study of fundamental biological processes, for the clinical monitoring of radiation therapy response at early time points after radiation (less than 24 h), as the first in vivo endpoint for the assessment of investigational PARP-1 inhibitor drugs, and as a means of selecting patients who may respond to PARP-1 inhibitor therapy.

Since PARP-1 activity levels directly correlate to therapy-induced DNA damage and the efficacy outcome of inhibitor therapy, radiolabelled inhibitors cannot provide the information that 6N-(triazo-PEG2-$^{18}$F)-NAD can provide as a substrate of the enzyme. Therefore, the current probe is the first capable of activity measurements and represents a significant improvement in PARP-1 activity assays.

One aspect of the disclosure, therefore, encompasses embodiments of a composition comprising a compound having the formula:

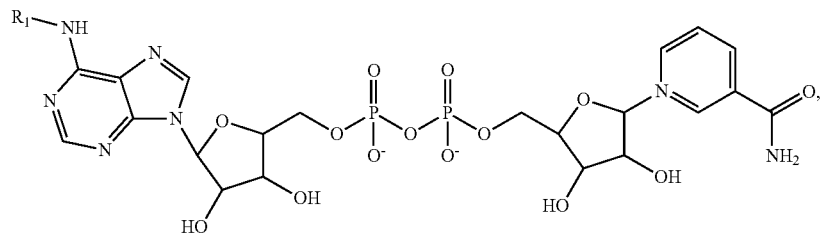
wherein: $R_1$ is
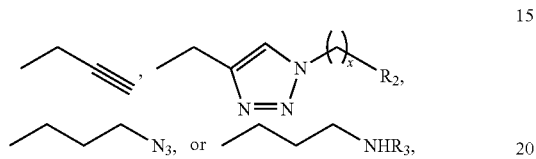
wherein x is 1 or 2; $R_2$ is a detectable label, a halogen, —(O—(CH$_2$))$_b$-halogen, —NH$_2$, or —NH—CO—(CH$_2$)$_a$—(O—(CH$_2$))$_b$—$R_4$, wherein a is any of 1-5 and b is any of 0-6; $R_4$ is —NH$_2$,
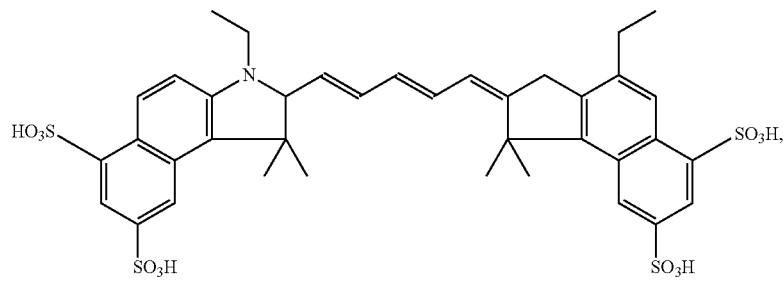 [SMILES: CCc1cc2c(S(=O)(=O)O)cc(S(=O)(=O)O)cc2c2c1C/C(=C/C=C/C=C/C1N(CC)c3ccc4c(S(=O)(=O)O)cc(S(=O)(=O)O)cc4c3C1(C)C)C2(C)C]
a chelator, or a chelator-metal ion complex; $R_3$ is H or —CO—(CH$_2$)$_5$—$R_5$; $R_5$ is —N$_3$, —NH$_2$, or —NH—CO—(CH$_2$)$_5$—$R_6$; $R_6$ is —N$_3$, —NH$_2$,
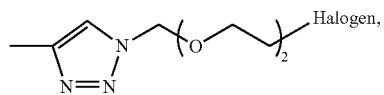
or —NH—CO—(CH$_2$)$_y$—$R_7$, wherein y is 1 or 2; and $R_7$ is
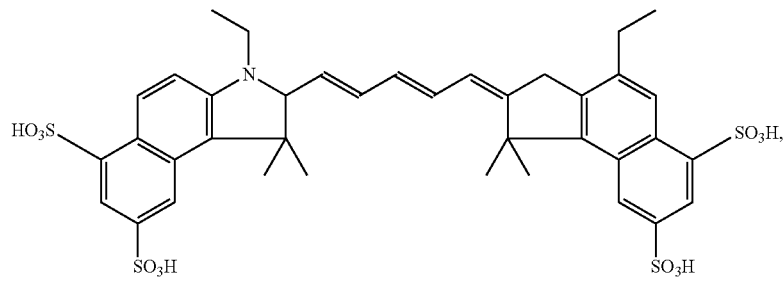 [SMILES: CCc1cc2c(S(=O)(=O)O)cc(S(=O)(=O)O)cc2c2c1C/C(=C/C=C/C=C/C1N(CC)c3ccc4c(S(=O)(=O)O)cc(S(=O)(=O)O)cc4c3C1(C)C)C2(C)C]
a chelator, or a chelator-metal complex.

In embodiments of this aspect of the disclosure, the compound can be as shown in FIG. 20 or 21.

In embodiments of this aspect of the disclosure, the halogen can be fluorine, chlorine, or iodine.

In embodiments of this aspect of the disclosure, the detectable label may be selected from the group consisting of $^{18}$F, $^{123}$I, $^{131}$I, $^{125}$I, and $^{11}$C.

In embodiments of this aspect of the disclosure, the chelator may be ethylaminediaminetetracetate (EDTA), diethylene triamine pentaacetic acid (DPTA), or 1,4,7,10-tetraazacyclododecane-1,4,7,10-tetraacetate (DOTA).

In some embodiments of this aspect of the disclosure, the chelator may have a detectable metal ion bound thereto.

In embodiments of this aspect of the disclosure, the detectable metal ion bound thereto may be selected from the group consisting of: $^{64}$Cu, $^{48}$V, $^{52}$Fe, $^{55}$Co, $^{94}$mTc, $^{68}$Ga, $^{99}$mTc, $^{111}$IN, $^{113}$In and $^{67}$Ga.

In some embodiments of this aspect of the disclosure, the compound can have the formula:

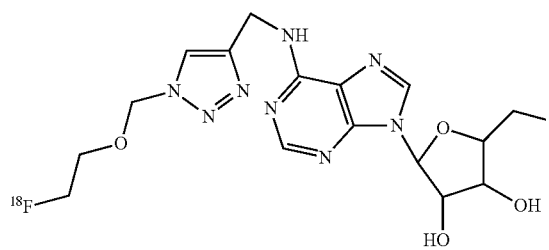

In some embodiments of this aspect of the disclosure, the composition may further comprise a pharmaceutically acceptable carrier.

Another aspect of the disclosure encompasses embodiments of a method of detecting a poly[ADP-ribose] polymerase-1(PARP-1) activity in an animal or human subject, said method comprising the steps of: (i) administering to an animal or human subject a PARP-1-specific probe composition comprising a compound having the formula:

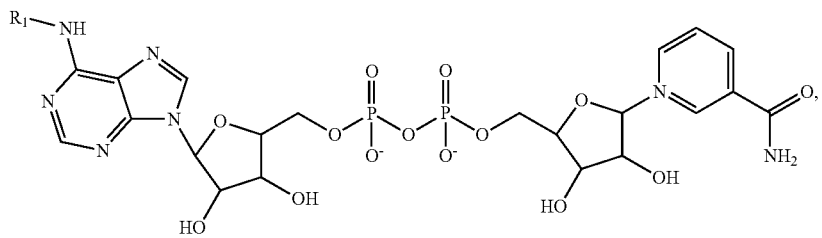

wherein: $R_1$ is

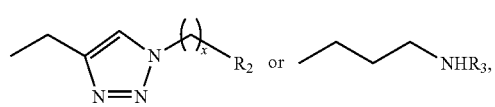

wherein x is 1 or 2; $R_2$ is a detectable label, a halogen, —(O—(CH$_2$))$_b$-halogen, or —NH—CO—(CH$_2$)$_a$—(O—(CH$_2$))$_b$—R$_4$, wherein a is any of 1-5 and b is any of 0-6; R$_4$ is a chelator, or a chelator-metal ion complex; R$_3$ is H or —CO—(CH$_2$)$_5$—R$_5$; R$_5$ is —NH—CO—(CH$_2$)$_5$—R$_6$; R$_6$ is

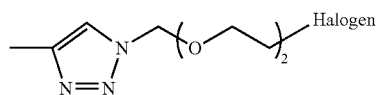

or —NH—CO—(CH$_2$)$_y$—R$_7$, wherein y=1 or 2; and R$_7$ is, a chelator, or a chelator-metal complex, and the PARP-1-specific probe composition further comprises a pharmaceutically acceptable carrier; (ii) generating a Positron Emission Tomography (PET) signal emitted by the administered probe composition in the animal or human subject; and (iii) generating an image of a localized concentration of the PET signal relative to the body of the animal or human subject, said concentration indicating a site of PARP-1 activity in the subject.

In embodiments of this aspect of the disclosure, the compound may be as shown in FIG. 20 or 21.

In embodiments of this aspect of the disclosure, the halogen may be fluorine, chlorine, or iodine.

In embodiments of this aspect of the disclosure, the detectable label may be selected from the group consisting of $^{18}$F, $^{123}$I, $^{131}$I, $^{125}$I.

In embodiments of this aspect of the disclosure, the chelator may be ethylaminediaminetetracetate (EDTA), diethylene triamine pentaacetic acid (DPTA), or 1,4,7,10-tetraazacyclododecane-1,4,7,10-tetraacetate (DOTA).

In embodiments of this aspect of the disclosure, the chelator may have a detectable metal ion bound thereto.

In embodiments of this aspect of the disclosure, the detectable metal ion bound thereto is selected from the group consisting of: $^{64}$Cu, $^{48}$V, $^{52}$Fe, $^{55}$Co, $^{94}$mTc, $^{68}$Ga, $^{99}$mTc, $^{111}$In, $^{113}$In, and $^{67}$Ga.

In embodiments of this aspect of the disclosure, the PARP-1-specific probe composition comprises a compound having the formula:

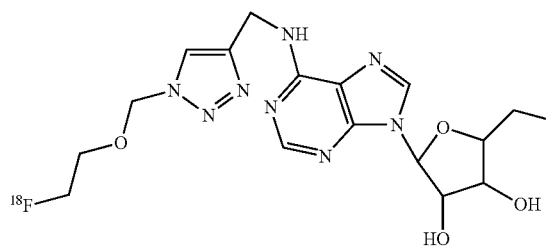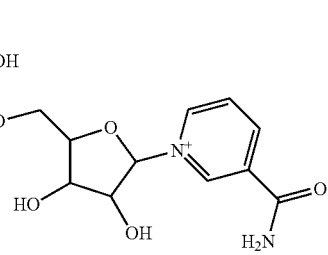

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLE

Example 1

PARP-1 Probe $^{18}$F Click Chemistry
First Step:

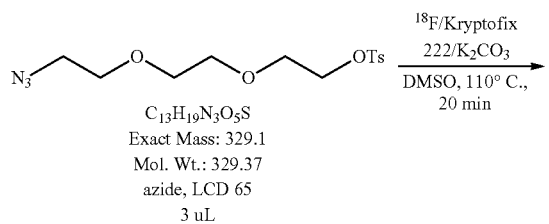

$C_{13}H_{19}N_3O_5S$
Exact Mass: 329.1
Mol. Wt.: 329.37
azide, LCD 65
3 uL

-continued

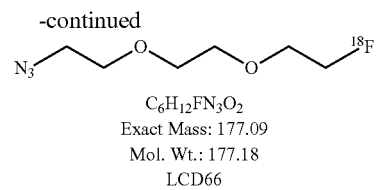

$C_6H_{12}FN_3O_2$
Exact Mass: 177.09
Mol. Wt.: 177.18
LCD66

Semi-Prep Condition HPLC: Phenomenex Gemini C18 column (250×10 mm, 5 μm) and gradient conditions (method A): A: $H_2O$+0.1% TFA, B: $CH_3CN$+0.1% TFA; 0-2 min 5% B, 2-30 min 5-65% B, 30-40 min 60-95% B; 5.0 mL/min.

$^{18}$F azide: 10-300 mCi (containing $^{19}$F Azide 5-150 nmol)

Synthesis of [18F]azide (LCD66): LCD66 was fully-automated synthesized in a Tracerlab FX-FN module (GE Healthcare, USA). Briefly, no-carrier added [$^{18}$F]-fluoride was produced via the $^{18}$O (p,n)$^{18}$F nuclear reaction by irradiation of enriched [$^{18}$O]$H_2O$ in a PETtrace cyclotron (GE Healthcare, USA). [$^{18}$F]Fluoride was trapped on an anion-exchange resin cartridge (Macherey-Nagel Chromafix 30-PS-HCO3 pre-conditioned with 1 mL of EtOH, 1 mL of $H_2O$ and then blown dry). The cartridge was eluted with a solution of Kryptofix K2.2.2™ (15 mg) and potassium carbonate (3 mg) in $H_2O$ (0.1 mL) and $CH_3CN$ (0.9 mL). Following azeotropic drying, compound LCD65 (3.0 mg in 1.0 mL dry DMSO) was added to the K[$^{18}$F]F/K2.2.2. complex and the mixture was heated for 20 min at 110° C. to yield LCD66.

After cooling to room temperature, the reaction mixture was loaded on semi-prep HPLC (method A). The fraction corresponding to the peak of the desired product (retention time approximately 21 min) was collected in a round bottom flask containing sterile water (20 mL), and then transferred to an adjacent customized module for solid phase extraction (SPE) using a C-18 Sep-Pak. LCD66 trapped on C-18 cartridge was eluted with diethyl ether (2 mL) through a $Na_2SO_4$ cartridge into a 5 mL V-vial with stirrer bar in the customized module. The diethyl ether was removed under helium stream at ambient temperature and the dried labeling agent was reconstituted with THF (50 μL) for further click chemistry.

Second Step:

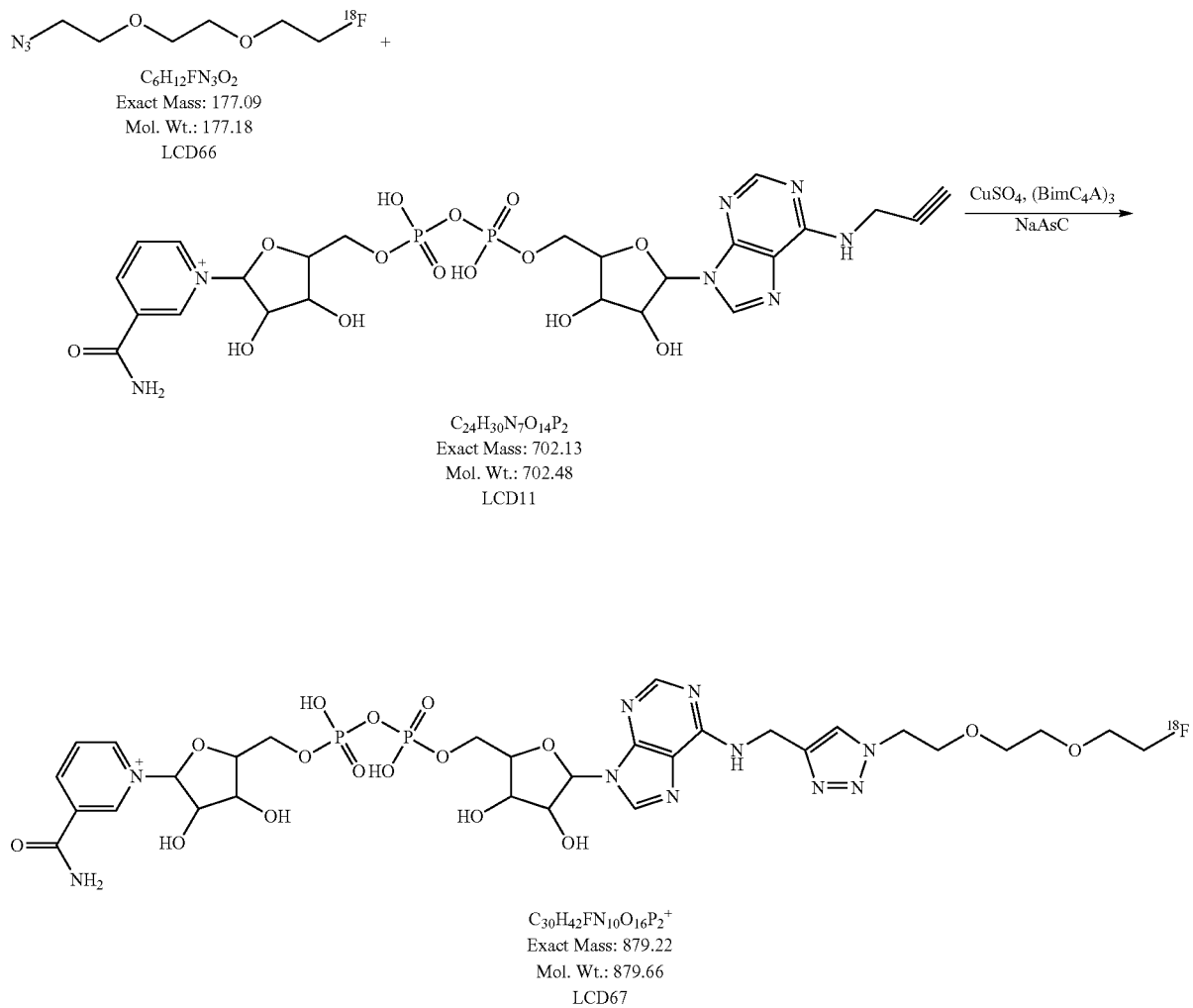

$^{18}$F azide (LCD 66): 10-300 mCi (containing $^{19}$F Azide 5-150 nmol)

To HEPES (0.2 M, 100 μL), a solution of LCD66 in THF (1 μL, 30 nmol) was added a solution of the active probe LCD11 (0.351 mg), CuSO$_4$ (100 nmol), sodium ascorbate (1010 nmol) and accelerator ligand potassium 5,5',5"-(2,2',2"-nitrilotris(methylene)tris(1H-benzimidazole-2,1-diyl)) tripentanoate (BimC$_4$A)$_3$ (30 nmol), and reaction mixture was kept at room temperature for 20 min. Crude product was diluted with 2 mL of water and injected on semi-prep for purification (method B). Final product LCD67 was formulated in saline with <10% ethanol by SPE.
Substrate (alkyne) (LCD 11): 100 μL containing 0.351 mg LCD11 (500 nmol) Solvent system: 100 μL of HEPES (0.2 M, 100 μL), water; CuSO$_4$: 1 μL of 0.1 M stock, 25 mg/1000 μL, 100 nmol; Ligand: 1 μL, house made, 30 mM stock, 30 nmol; Sodium Ascorbate: 1 μL of freshly made solution (20 mg/100 μL), 1010 nmol; Temperature: r.t.; Reaction time: 20 min.
HPLC condition: A: 0.1% TFA water/B: 0.1% TFA MeCN; Semi-Prep Condition: C-18 Gemini, 5 ml/min, B: 2-15% 0-40 min, LCD11 (precursor) Rt=13 min. LCD67 (product) Rt=19 min.

Analytical Condition: C-18 Gemini, 1 ml/min, B: 1-15% 0-15 min, LCD11 (precursor) Rt=5 min; LCD67 (product) Rt=8 min.

Example 2

All chemicals were purchased from commercial sources (Sigma-Aldrich, TCI America, etc.) and used without further purification unless otherwise noted. Analytical TLC was performed with 0.25 mm silica gel 60F plates with fluorescent indicator (254 nm). Plates were visualized by ultraviolet light and stained with sulfuric acid (5% aqueous solution, for carbohydrate molecules), or potassium permanganate solution. High-performance liquid chromatography (HPLC) was performed on a Dionex HPLC System (Dionex Corporation) equipped with a GP50 gradient pump and an in-line diode array UV-Vis detector. A reversed-phase C18 (Phenomenax, 5 μm, 4.6×250 mm or Dionex, 5 μm, 21.2×250 mm) column was used with a MeCN/H2O gradient mobile phase containing 0.1% trifluoroacetic acid (at a flow rate of 1 or 12 mL/min for analysis or purification respectively). The $^1$H and $^{13}$C NMR spectra were acquired on Varian 400 or 500 MHz magnetic resonance spectrometers (Department Example 3

Synthetic Procedure and Characterization

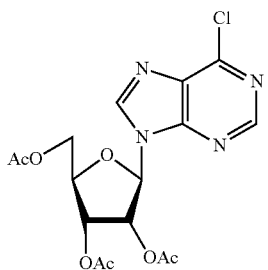

6-Chloroadenosine 2′,3′,5′-Triacetate (LCD06)

Compound LCD06 was synthesized under standard glycosylation conditions. Briefly, β-D-ribofuranose 1,2,3,5-tetraacetate (5.5 g, 17.3 mmol) and 6-chloropurine (2.7 g, 17.3 mmol) were dissolved in anhydrous MeCN (50 mL) containing molecular sieves (MS 4 Å), followed by the addition of TMSOTf (300 µL) at 0° C. under argon protection. The reaction mixture was heated at 60° C. overnight and quenched by addition of triethylamine to pH 7. The solvents were then removed and column chromatography (methanol:dichloromethane, 1:20) gave the product as a yellowish solid (4.9 g, 69%). $^1$H NMR (400 MHz, CDCl$_3$) δ 8.77 (s, 1H, H-8), 8.24 (s, 1H, H-2), 6.23 (d, 1H, J=5.4 Hz, H-1′), 5.94 (dd, 1H, J=5.4, 5.0 Hz, H-2′), 5.63 (dd, 1H, J=5.0, 4.5 Hz, H-3′), 4.35 (m, 3H, H-4′, H-5′), 2.26 (s, 3H, CH$_3$), 2.07 (s, 3H, CH$_3$), 2.01 (s, 3H, CH$_3$).

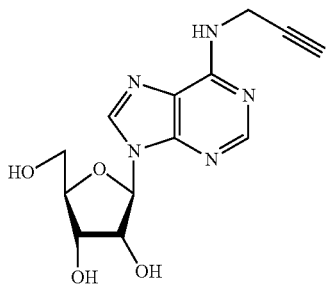

6-N-Propargyladenosine (LCD08)

To a solution of LCD06 (1.0 g, 2.42 mmol) in methanol (10 mL) at 0° C. was added ammonium hydroxide (30% in water, 400 µL). The reaction mixture was then stirred for 24 hours at r.t. and the reaction was quenched by addition of DOWEX-5×8-200. The reaction mixture was then filtered and solvents were removed to give a yellowish solid (LCD07), which was then dissolved/suspended in acetonitrile (5 mL), followed by the addition of propargyl amine (1.5 mL, 24.2 mmol) and potassium carbonate (1.0 g, 7.26 mmol). The suspension was stirred at r.t. for 2 days, and solvents were removed. The compound was purified by column chromatography (methanol:dichloromethane, 1:20) to give the product as a yellowish white solid (517 mg, 70%, two steps). $^1$H NMR (500 MHz, DMSO-d6): δ 8.42 (s, 1H, H-8), 8.30 (s, 1H, H-2), 5.92 (d, 1H, J=6.4 Hz, H-1′), 5.50 (d, 1H, J=6.7 Hz, NH), 5.37 (dd, 1H, J=4.5, 1.5 Hz), 5.17 (d, 1H, J=4.5 Hz, OH), 4.60 (dd, 1H, J=6.0, 5.5 Hz, H-2′), 4.20 (br, 2H, NHCH$_2$), 4.16 (dd, 1H, J=4.0, 3.5 Hz, H-4′), 4.00 (dd, 1H, J=5.5, 3.0 Hz, H-3′), 3.70 (m, 1H, H-5a′), 3.57 (m, 1H, H-5b′), 3.04 (s, 1H, propargyl-CH). $^{13}$C NMR (125 MHz, DMSO-d6): 155.1 (Ar), 152.6 (Ar), 148.0 (Ar), 139.8 (Ar), 121.0 (Ar), 88.2 (C-1′), 85.8, 82.1, 73.5, 72.4, 70.1, 61.3, 28.8 (NHCH$_2$). HRMS (ESI) calcd for C$_{13}$H$_{16}$N$_5$O$_4$ (M+H$^+$) 306.1201. found: 306.1258.

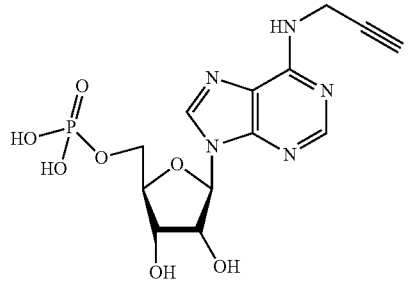

6-N-Propargyladenosine 5′-monophosphate (LCD09, 6-N-Propargyl AMP)

To a solution of LCD08 (200 mg, 0.66 mmol) in trimethyl phosphite (4.0 mL) was added phosphoryl chloride (247 µL, 2.62 mmol) at 0° C. The reaction mixture was stirred at 0° C. for 10 hours, and the reaction was quenched by addition of a mixture of water (30 mL) and ethyl acetate (30 mL). The water layer was subjected to HPLC purification immediately, and lyophilization gave product LCD09 as a white fluffy powder (244 mg, 96%). $^1$H NMR (500 MHz, D$_2$O): δ 8.48 (s, 1H, H-8), 8.32 (s, 1H, H-2), 6.00 (d, 1H, J=5.1 Hz, H-1′), 4.57 (t, 1H, J=5.1 Hz, H-2′), 4.33 (t, 1H, J=4.5 Hz, H-3′), 4.28 (br, 2H, NHCH$_2$), 4.21 (m, 1H, H-4′), 4.04 (m, 1H, H-5a′), 3.99 (m, 1H, H-5b′), 2.61 (s, 1H, propargyl-CH). $^{13}$C NMR (125 MHz, D$_2$O) δ149.0 (Ar), 147.0 (Ar), 145.2 (Ar), 142.2 (Ar), 118.9 (Ar), 88.4 (C-1′), 84.2, 84.1, 74.7, 70.3, 64.7, 64.7, 31.6 (NHCH$_2$). HRMS (ESI) calcd for C$_{13}$H$_{17}$N$_5$O$_7$P (M+H$^+$) 386.0866. found: 386.0883.

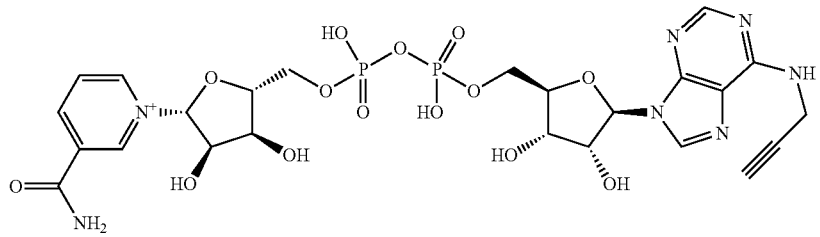 [SMILES: C#CCNc1ncnc2c1ncn2[C@@H]1O[C@H](COP(=O)(O)OP(=O)(O)OC[C@H]2O[C@@H]([n+]3cccc(C(N)=O)c3)[C@H](O)[C@@H]2O)[C@@H](O)[C@H]1O]

Nicotinamide 6-N-propargyladenine dinucleotide (LCD11, 6-N-Propargyl NAD)

LCD09 (30 mg, 0.078 mmol) was dissolved in dry DMF (1 mL) containing triphenylphosphine (170 mg, 0.39 mmol), 2,2'-dipyridinyl disulfide (86 mg, 0.39 mmol) and morpholine (54 µL, 0.62 mmol). The reaction mixture was stirred at r.t. for 4 hours and ether was added to give white precipitate LCD14, which was collected, washed with ether and dried under vacuum. HRMS (ESI) calcd for $C_{17}H_{24}N_6O_7P$ (M+H$^+$): 455.1444. found: 455.1467. The crude LCD14 and LCD15 (31 mg 0.094 mmol) were dissolved together in dry DMF (3.5 mL) containing manganese (II) chloride (88 mg, 0.70 mmol), and the mixture was stirred for 1 day at r.t. and was quenched with water. Preparative HPLC separation followed by lyophilization gave the product as a white solid (85%). $^1$H NMR (500 MHz, D$_2$O): δ 9.40 (s, 1H, H—N2), 9.29 (s, 1H, H—N6), 8.93 (s, 1H, H—N4), 8.60 (s, 1H, H-8), 8.45 (s, 1H, H-2), 8.31 (t, 1H, J=7.1 Hz, H—N5), 6.21 (dd, 1H, J=4.9 Hz, H—N1'), 6.18 (d, 1H, J=5.6 Hz, H-1'), 4.75 (dd, 1H, J=4.6, 4.5 Hz, H—N2'), 4.73 (t, 1H, J=5.6 Hz, H-2'), 4.65 (dd, 1H, J=5.1, 4.6 Hz, H—N3'), 4.52 (t, 1H, J=4.5 Hz, H-3'), 4.40 (m, 4H), 4.38 (d, 1H, J=3.0 Hz), 4.25 (m, 3H), 2.71 (s, 1H, propargyl-CH). $^{13}$C NMR (125 MHz, D$_2$O): 165.7 (C=O), 150.2 (Ar), 148.3 (Ar), 147.5 (Ar), 147.6 (Ar), 144.96 (Ar), 143.7 (Ar), 142.2 (Ar), 134.0 (Ar), 129.4 (Ar), 119.5 (Ar), 90.8 (C—N1'), 89.2 (C-1'), 85.4, 84.1, 77.2, 76.2, 75.9, 75.3, 71.5, 71.1, 66.2, 64.3, 32.4 (NHCH$_2$). HRMS (ESI) calcd for $C_{24}H_{30}N_7O_{14}P_2$ (M$^+$): 702.1320. found: 702.1360.

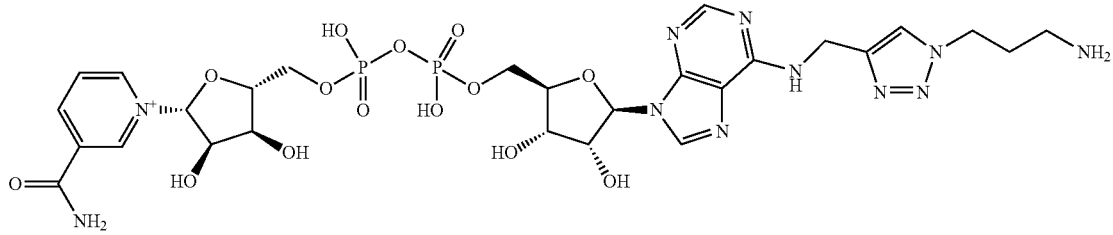 [SMILES: NCCCn1cc(CNc2ncnc3c2ncn3[C@@H]2O[C@H](COP(=O)(O)OP(=O)(O)OC[C@H]3O[C@@H]([n+]4cccc(C(N)=O)c4)[C@H](O)[C@@H]3O)[C@@H](O)[C@H]2O)nn1]

LCD23

3-Chloropropylamine hydrochloride (2.0 g, 15.4 mmol) was dissolved in water (10 mL) containing sodium azide (3.0 g, 46.1 mmol), and the reaction mixture was heated for 24 hours at 80° C. The solution was then cooled to r.t. and was used directly in the reaction with LCD11. Briefly, LCD11 (5.0 mg, 0.007 mmol) and 3-azidopropylamine (1.1 mg, 0.011 mmol) was dissolved in HEPES buffer (0.1 M, 1 mL final volume) containing copper sulfate (0.1 M final concentration), tripotassium 5,5',5''-[2,2',2''-nitrilotris(methylene) tris(1H-benzimidazole-2,1-diyl)]tripentanoate (Bim-C$_4$A)$_3$ (1 µL, 30 mM stock). The mixture was degassed and sodium ascorbate (0.2 mg, 1.0 µmol) was added at an Ar atmosphere. The reaction was monitored by HPLC and reached completion after 5 min. The product mixture was purified by HPLC and lyophilized to give LCD23 as a white fluffy solid (5.4 mg, 96%). HRMS (ESI) calcd for $C_{27}H_{38}N_{11}O_{14}P_2$ (M$^+$): 802.2069. found: 802.2120.

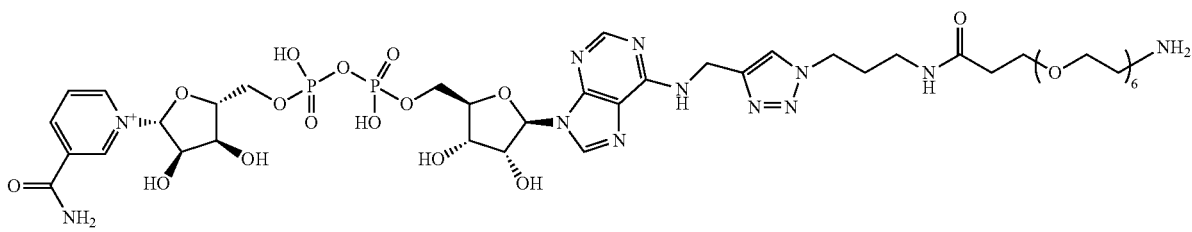

LCD24

Fmoc-N-amido-dPEG$_6$-acid (Quanta Biodesign, #10063, 100 mg, 0.17 mmol) and 3-azidopropylamine (17.4 mg, 0.17 mmol) were coupled in DMF (1 mL) containing HBTU (99 mg, 0.26 mmol), HOBt (40 mg, 0.26 mmol) and DIPEA (91 µL, 0.52 mmol) at r.t. The reaction mixture was stirred overnight and was extracted using dichloromethane and water. The organic layer was collected and dried under MgSO$_4$. Solvents were then removed to give the product as a clear oil (LCD21). The crude LCD21 (0.174 mmol) was then dissolved in DMF (1 mL) containing piperidine (50 µL), and the solution was kept at r.t. overnight. Ether (50 mL) was added to quench the reaction and to precipitate out the product LCD22. The white solid was collected, washed with ether, dried under vacuum, and used directly in the next step reaction. LCD22 dissolved in water together with LCD11 (5.0 mg, 0.007 mmol) following similar procedure as that for LCD23. HPLC purification and lyophilization gave the product as a white fluffy powder (8.0 mg, 100%). HRMS (ESI) calcd for $C_{27}H_{38}H_{11}O_{14}P_2$ (M$^+$): 1137.4013. found: 1137.4076.

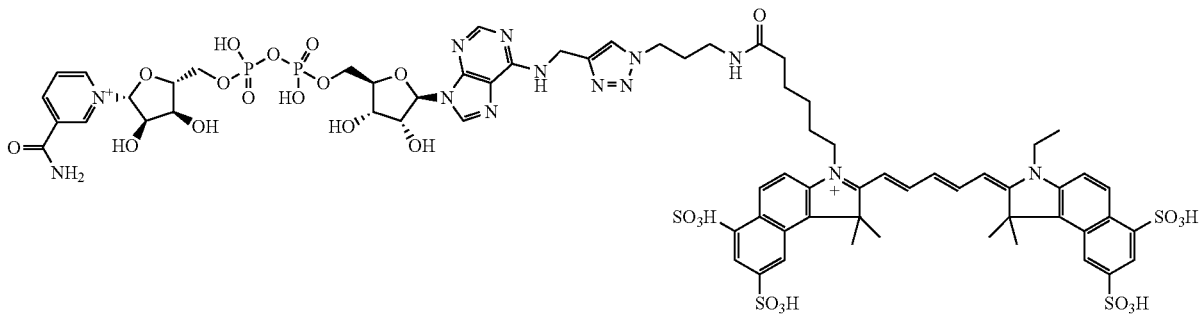

LCD19

Cy5.5-NHS ester (4.0 mg, 3.5 µmol) and 3-azidopropylamine (1.8 mg, 17.7 µmol) were incubated in DMF (100 µL) containing DIPEA (1.9 µL, 10.5 µmol) at r.t. for 1 h, and ether was added to quench the reaction, dark blue precipitate LCD18 was obtained after drying the sample under vacuum (3.4 mg). LCD18 and LCD11 (0.5 mg, 0.7 µmol) were then treated according to a similar procedure as that for LCD23 to give compound LCD19. HRMS (ESI) calcd for $C_{68}H_{81}N_{13}O_{27}P_2S_4^{2+}$ (M$^{2+}$): 1701.3712.

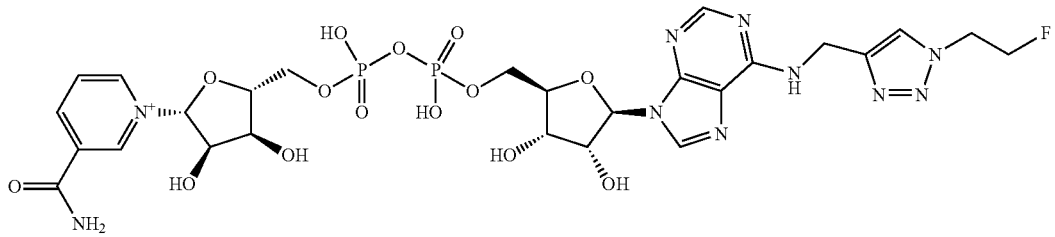 [SMILES: NC(=O)c1ccc[n+]([C@@H]2O[C@H](COP(=O)(O)OP(=O)(O)OC[C@H]3O[C@@H](n4cnc5c(NCc6cn(CCF)nn6)ncnc54)[C@H](O)[C@@H]3O)[C@@H](O)[C@H]2O)c1]

LCD29

2-Fluoroethyl azide (1.0 mg, 11.2 µmol) and LCD11 (1.0 mg, 1.4 µmol) were treated according to a similar procedure as that for LCD23 to give compound LCD29 (1.1 mg, 99%). HRMS (ESI) calcd for $C_{26}H_{34}FN_{10}O_{14}P_2^+$ (M$^+$): 791.1710. found: 791.1752.

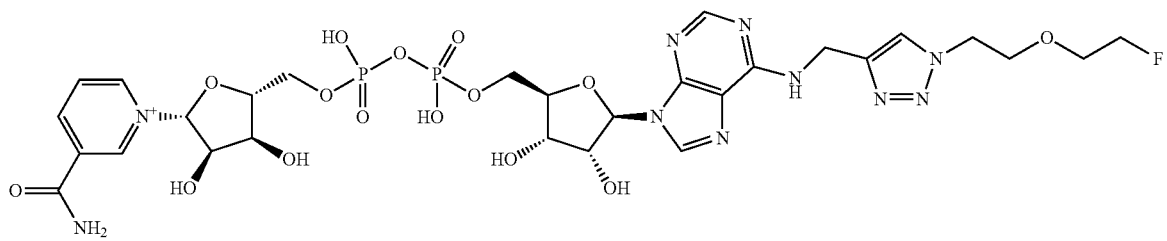 [SMILES: NC(=O)c1ccc[n+]([C@@H]2O[C@H](COP(=O)(O)OP(=O)(O)OC[C@H]3O[C@@H](n4cnc5c(NCc6cn(CCOCCF)nn6)ncnc54)[C@H](O)[C@@H]3O)[C@@H](O)[C@H]2O)c1]

LCD69

2-(2-Fluoroethoxy)ethyl azide (1.0 mg, 7.5 µmol) and LCD11 (1.0 mg, 1.4 µmol) were treated according to a similar procedure as that for LCD23 to give compound LCD69 (1.1 mg, 94%). HRMS (ESI) calcd for $C_{28}H_{38}FN_{10}O_{15}P_2^+$ (M⁺): 835.1972. found: 835.2020.

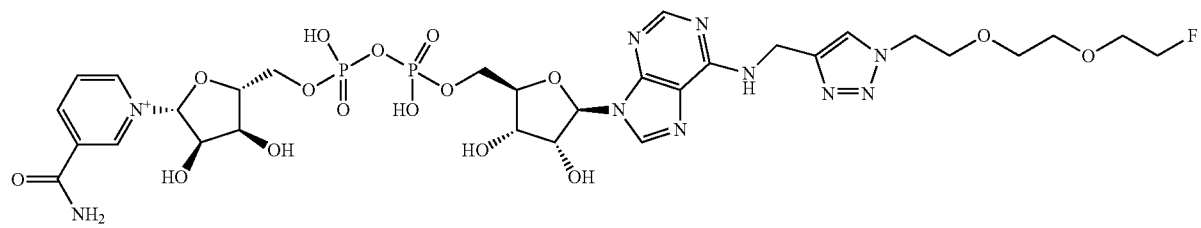 [SMILES: NC(=O)c1ccc[n+]([C@@H]2O[C@H](COP(=O)(O)OP(=O)(O)OC[C@H]3O[C@@H](n4cnc5c(NCc6cn(CCOCCOCCF)nn6)ncnc54)[C@H](O)[C@@H]3O)[C@@H](O)[C@H]2O)c1]

LCD67

2-((2-Fluoroethoxy)ethoxy)ethyl azide (0.5 mg, 2.8 µmol) and LCD11 (1.0 mg, 1.4 µmol) were treated according to a similar procedure as that for LCD23 to give compound LCD67 (1.2 mg, 96%). HRMS (ESI) calcd for $C_{30}H_{42}FN_{10}O_{16}P_2^+$ (M⁺): 879.2234. found: 879.2291.

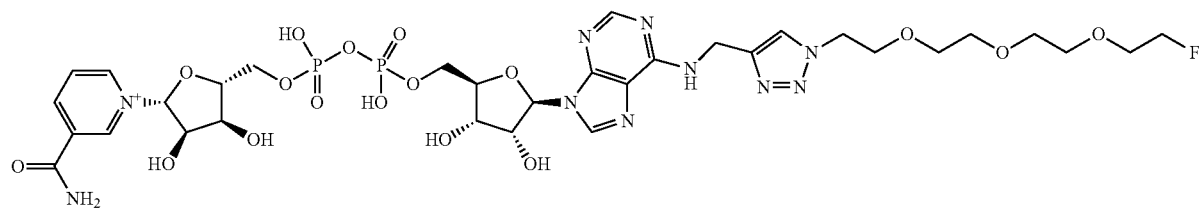 [SMILES: NC(=O)c1ccc[n+]([C@@H]2O[C@H](COP(=O)(O)OP(=O)(O)OC[C@H]3O[C@@H](n4cnc5c(NCc6cn(CCOCCOCCOCCF)nn6)ncnc54)[C@H](O)[C@@H]3O)[C@@H](O)[C@H]2O)c1]

LCD77

2-(((2-Fluoroethoxy)ethoxy)ethoxy)ethyl azide (1.0 mg, 4.5 µmol) and LCD11 (1.0 mg, 1.4 µmol) were treated according to a similar procedure as that for LCD23 to give compound LCD77 (1.2 mg, 93%). HRMS (ESI) calcd for $C_{32}H_{46}FN_{10}O_{17}P_2^+$ (M⁺): 923.2496. found: 923.2532.

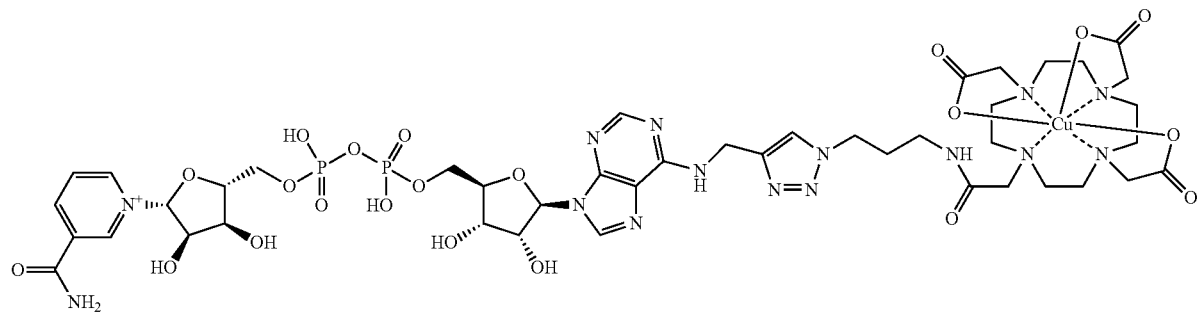

LCD27

LCD23 (1.0 mg, 1.2 µmol) and 2,2',2''-(10-(2-((2,5-dioxopyrrolidin-1-yl)oxy)-2-oxoethyl)-1,4,7,10-tetraazacyclododecane-1,4,7-triyl)triacetic acid (DOTA-NHS ester) (1.0 mg, 1.3 µmol, Macrocyclics) were dissolved in dry DMF (0.2 mL) containing DIPEA (1 µL). The mixture was stirred at r.t. for 1 hour and purified via HPLC to give the product LCD25 as a white fluffy solid. LCD25 (1.2 µmol) was dissolved in sodium acetate buffer (500 µL, 0.1 M), and copper chloride (1.7 mg, 12.5 µmol) was added. The reaction mixture was heated at 50° C. for 1 hour, and purified via HPLC to give the product as a blue-ish fluffy solid (1.3 mg, 87%, two steps). HRMS (ESI) calcd for $C_{43}H_{61}CuN_{15}O_{21}P_2^+$ (M⁺): 1248.2932. found: 1248.3040.

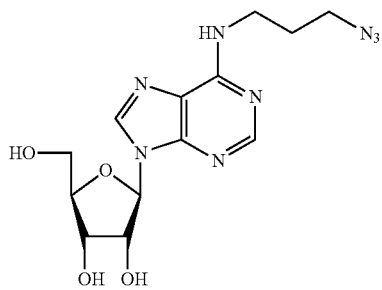

6-N-(3-Azidopropyl)adenosine (LCD32)

Compound LCD32 was prepared in a similar manner as that for compound LCD08. Briefly, to a solution of LCD07 (200 mg, 0.70 mmol) in ethanol (2 mL) was added 3-azidopropyl amine (420 mg, 4.2 mmol) and DIPEA (610 µL, 3.5 mmol). The suspension was stirred at r.t. for 4 days, and solvents were removed. The compound was purified by column chromatography (methanol:dichloromethane, 1:20) to give the product as a yellowish white solid (159 mg, 65%, two steps). HRMS (ESI) calcd for $C_{13}H_{19}N_8O_4$ (M+H$^+$): 351.1529. found: 351.1538.

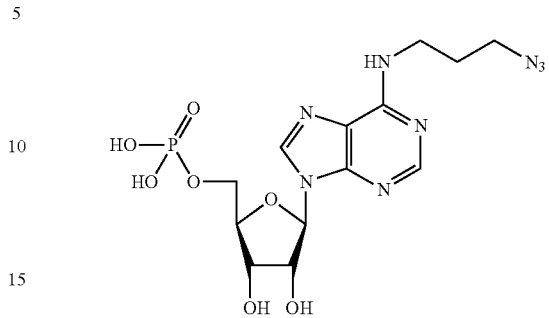

6-N-(3-Azidopropyl)adenosine 5'-monophosphate (LCD33, 6-N-(3-Azidopropyl) AMP)

Compound LCD33 was prepared in a similar manner as that for compound LCD09. The reaction with LCD32 (150 mg, 0.43 mmol) produced LCD33 as a white solid (138 mg, 75%). HRMS (ESI) calcd for: $C_{13}H_{20}N_8O_7P$ (M+H$^+$): 431.1193. found: 431.1209.

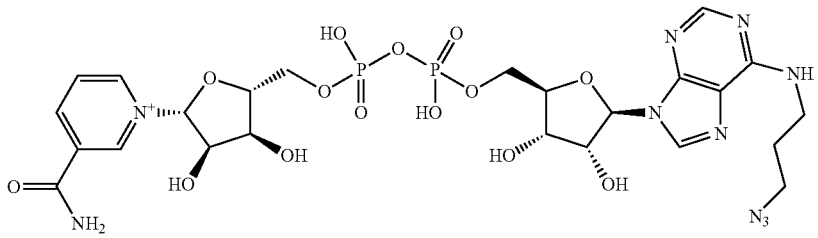 [SMILES: [N-]=[N+]=NCCCNc1ncnc2c1ncn2[C@@H]1O[C@H](COP(=O)(O)OP(=O)(O)OC[C@H]2O[C@@H]([n+]3cccc(C(N)=O)c3)[C@H](O)[C@@H]2O)[C@@H](O)[C@H]1O]

Nicotinamide 6-N-(3-Azidopropyl)adenine dinucleotide (LCD35, 6-N-(3-Azidopropyl) NAD)

Compound LCD35 was synthesized in a similar manner as LCD11. The reaction starting from LCD33 (30 mg, 70 µmol) and LCD15 (35 mg, 0.10 µmol) gave product LCD35 as a white fluffy solid (31 mg, 62%). HRMS (ESI) calcd for: $C_{24}H_{33}N_{10}O_{14}P_2^+$ (M$^+$): 747.1647. found: 747.1693.

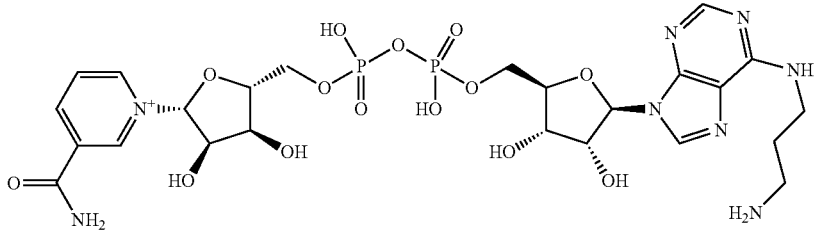 [SMILES: NCCCNc1ncnc2c1ncn2[C@@H]1O[C@H](COP(=O)(O)OP(=O)(O)OC[C@H]2O[C@@H]([n+]3cccc(C(N)=O)c3)[C@H](O)[C@@H]2O)[C@@H](O)[C@H]1O]

Nicotinamide 6-N-(3-Aminopropyl)adenine dinucleotide (LCD36, 6-N-(3-Aminopropyl) NAD)

Compound LCD35 (20 mg, 26 µmol) was dissolved in aqueous solution (0.5 mL) containing sodium bicarbonate solution (80 mM) and tris(2-carboxyethyl)phosphine hydrochloride (TCEP-HCl, 20 mM) at r.t. and kept for overnight. HPLC purification provided the product LCD36 as a white fluffy solid (6.0 mg, 52%). HRMS (ESI) calcd for: $C_{24}H_{35}N_8O_{14}P_2^+$ (M$^+$): 721.1742. found: 721.1785.

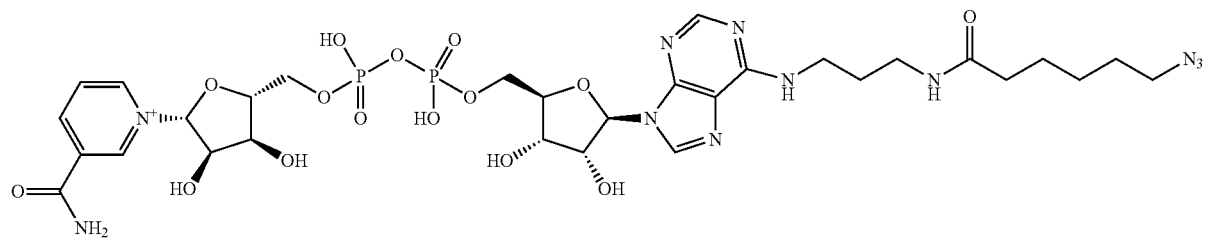 [SMILES: [N-]=[N+]=NCCCCCC(=O)NCCCNc1ncnc2c1ncn2[C@@H]1O[C@H](COP(=O)(O)OP(=O)(O)OC[C@H]2O[C@@H]([n+]3cccc(C(N)=O)c3)[C@H](O)[C@@H]2O)[C@@H](O)[C@H]1O]

LCD48

Compound LCD36 (1.0 mg, 1.4 µmol) and 6-azidohexanoic acid-NHS ester (0.7 mg, 2.8 µmol) were dissolved in DMF (0.2 mL) containing DIPEA (1 µL). The mixture was stirred at r.t. for 2 hours, and purified by HPLC to produce a white fluffy solid (1.2 mg, 99%). HRMS (ESI) calcd for: $C_{30}H_{44}N_{11}O_{15}P_2^+$ (M$^+$): 860.2488. found: 860.2460.

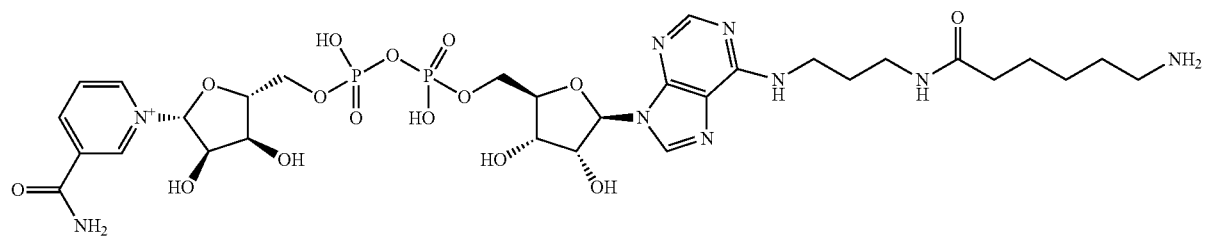 [SMILES: NCCCCCC(=O)NCCCNc1ncnc2c1ncn2[C@@H]1O[C@H](COP(=O)(O)OP(=O)(O)OC[C@H]2O[C@@H]([n+]3cccc(C(N)=O)c3)[C@H](O)[C@@H]2O)[C@@H](O)[C@H]1O]

LCD49

Compound LCD49 was synthesized in a similar manner as LCD36. The reaction starting from LCD48 (1.2 mg, 1.4 µmol) produced LCD49 as a white fluffy solid (0.5 mg, 46%). HRMS (ESI) calcd for: $C_{30}H_{46}N_9O_{15}P_2^+$ (M$^+$): 834.2583. found: 834.2610.

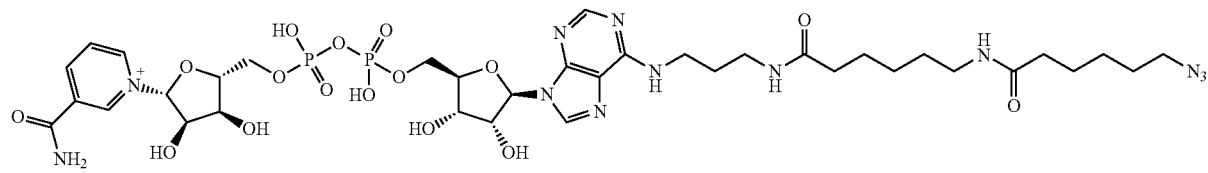

LCD50

Compound LCD50 was synthesized in a similar manner as LCD48. The reaction of LCD49 (0.5 mg, 0.6 µmol) and 6-azidohexanoic acid-NHS ester (1.0 mg, 4.0 µmol) produced LCD50 as a white fluffy powder (0.6 mg, 97%). HRMS (ESI) calcd for: $C_{36}H_{55}N_{12}O_{16}P_2^+$ (M$^+$): 973.3329. found: 973.3384.

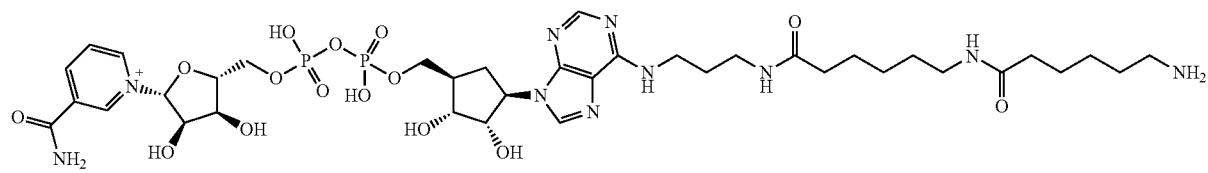

LCD51

Compound LCD51 was synthesized in a similar manner as LCD36. The reaction starting from LCD50 (0.5 mg, 0.5 µmol) produced LCD51 as a white fluffy solid (0.2 mg, 40%). HRMS (ESI) calcd for: $C_{36}H_{57}N_{10}O_{16}P_2^+$ (M+): 947.3424. found: 947.3392.

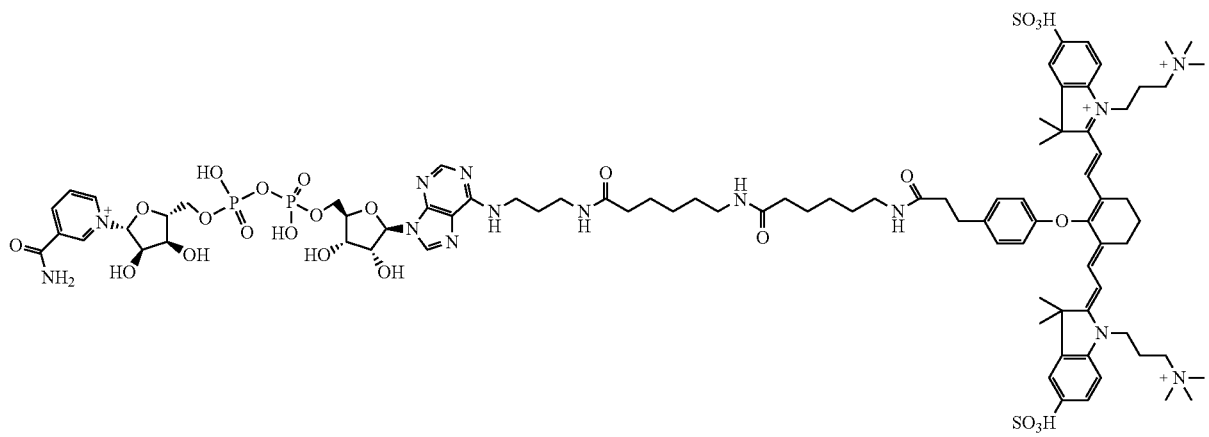

LCD53

Compound LCD51 (0.1 mg, 0.1 µmol) and ZW800-1 NHS ester (0.2 mg, The Flare Foundation) were incubated together in dry DMSO (120 µL) containing DIPEA (1 µL) for 1.5 hours at r.t. The compound was purified by HPLC to give a dark green fluffy solid (0.2 mg, 100%). HRMS (ESI) calcd for: $C_{87}H_{124}N_{14}O_{24}P_2S_2^{4+}$ (M4+): 1874.7808. found: 468.6901 (quadruple charged).

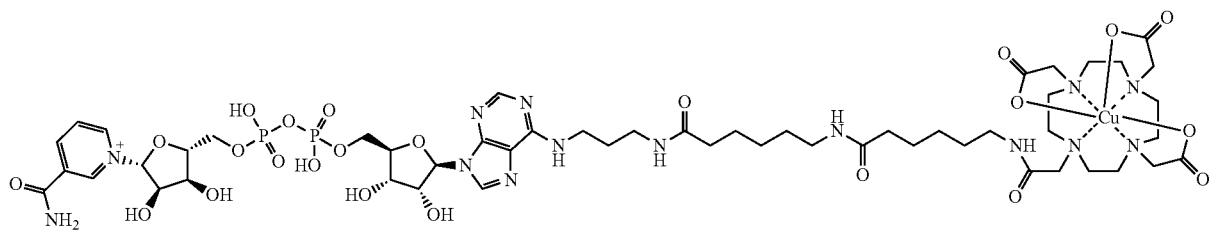

LCD28

Compound LCD28 was synthesized in a similar manner as LCD27. The reaction starting from LCD51 (1.0 mg, 1.1 µmol) and DOTA-NHS (0.8 mg, 1.2 µmol) produced LCD28 as a blue-ish fluffy solid (1.2 mg, 85%, two steps). HRMS (ESI) calcd for: $C_{52}H_{80}CuN_{14}O_{23}P_2^+$ (M+): 1393.4287. found: 1393.4429.

LCD70

Compound LCD50 (0.2 mg, 0.2 µmol) and 3-(2-(2-fluoroethoxy)ethoxy)propyne (0.5 mg, 3.4 µmol) were treated in a similar manner as the procedure for compound LCD11. The reaction yielded LCD70 as a white fluffy solid (0.2 mg, 89%). HRMS (ESI) calcd for: $C_{43}H_{66}FN_{12}O_{18}P_2^+$ (M+): 1119.4072. found: 560.2107 (double charged).

What is claimed:

1. A composition comprising a compound having the formula:

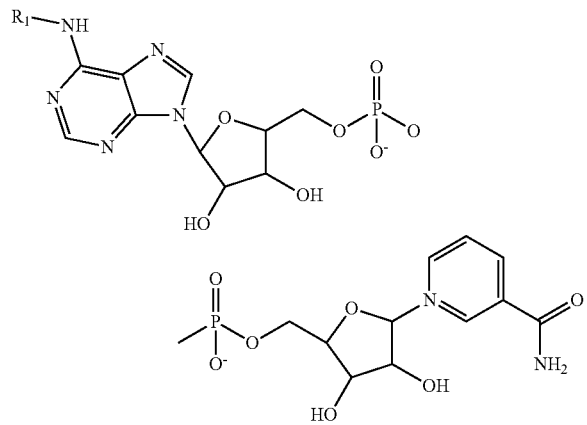

wherein:
$R_1$ is

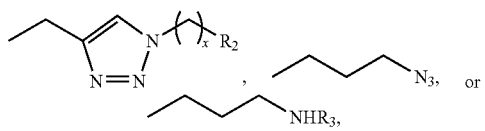

wherein x is 1 or 2,
$R_2$ is a detectable label, a halogen, —(O—(CH$_2$))$_b$-halogen, —NH$_2$, or —NH—CO—(CH$_2$)$_a$—(O—(CH$_2$))$_b$—R$_4$, wherein a is any of 1-5 and b is any of 0-6,
$R_4$ is —NH$_2$,

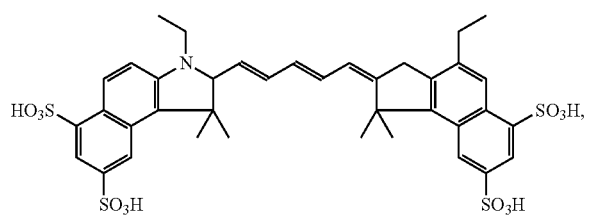 [SMILES: CCc1cc2c(S(=O)(=O)O)cc(S(=O)(=O)O)cc2c2c1C/C(=C/C=C/C=C/C1N(CC)c3ccc4c(S(=O)(=O)O)cc(S(=O)(=O)O)cc4c3C1(C)C)C2(C)C]

a chelator, or a chelator-metal ion complex,
$R_3$ is H or —CO—(CH$_2$)$_5$—R$_5$,
$R_5$ is —N$_3$, —NH$_2$, or —NH—CO—(CH$_2$)$_5$—R$_6$,
$R_6$ is —N$_3$, —NH$_2$,

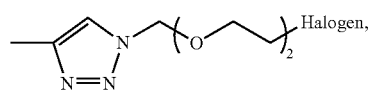

or —NH—CO—(CH$_2$)$_y$R$_7$, wherein y is 1 or 2, and
$R_7$ is

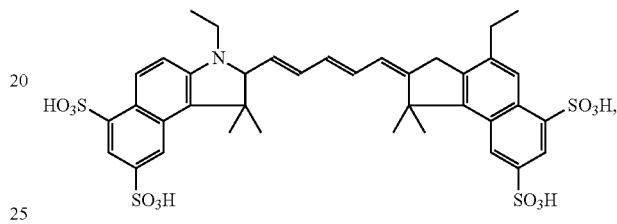

a chelator, or a chelator-metal complex.

2. The composition of claim 1, wherein the compound is selected from the group consisting of LCD23, LCD24, LCD19, LCD29, LCD69, LCD67, LCD77, LCD25, LCD27, LCD36, LCD48, LCD49, LCD50, LCD51, LCD53, LCD28, and LCD70 as shown in FIG. 20 or 21.

3. The composition of claim 1, wherein the halogen is fluorine, chlorine, or iodine.

4. The composition of claim 1, wherein the detectable label selected from the group consisting of $^{18}F$, $^{123}I$, $^{131}I$, $^{125}I$, and $^{11}C$.

5. The composition of claim 1, wherein the chelator is ethylaminediaminetetracetate (EDTA), diethylene triamine pentaacetic acid (DPTA), or 1,4,7,10-tetraazacyclododecane-1,4,7,10-tetraacetate (DOTA).

6. The composition of claim 1, wherein the chelator has a detectable metal ion bound thereto.

7. The composition of claim 6, wherein the detectable metal ion bound thereto is selected from the group consisting of: $^{64}Cu$, $^{48}V$, $^{52}Fe$, $^{55}Co$, $^{94}mTc$, $^{68}Ga$, $^{99}mTc$, $^{111}In$, $^{113}In$, and $^{67}Ga$.

8. The composition of claim 1, wherein the compound having has the formula:

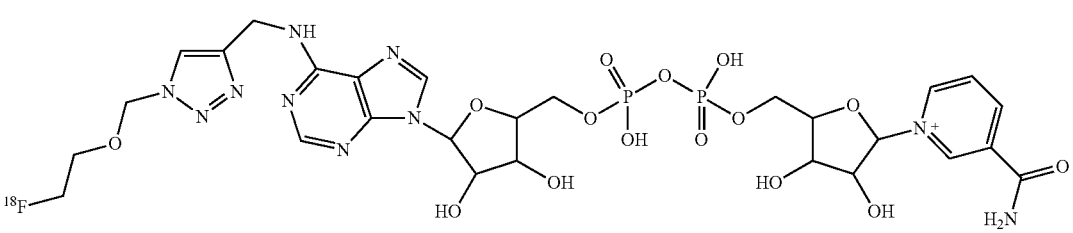

9. The composition of claim 1, further comprising a pharmaceutically acceptable carrier.

\* \* \* \* \*